US008071365B2

(12) United States Patent
Kroger et al.

(10) Patent No.: US 8,071,365 B2
(45) Date of Patent: Dec. 6, 2011

(54) PSOD EXPRESSION UNITS

(75) Inventors: Burkhard Kroger, Limburgerhof (DE); Oskar Zelder, Speyer (DE); Corinna Klopprogge, Mannheim (DE); Hartwig Schroder, Nussloch (DE); Stefan Haefner, Ludwigshafen (DE)

(73) Assignee: BASF SE (DE)

( * ) Notice: Subject to any disclaimer, the term of this patent is extended or adjusted under 35 U.S.C. 154(b) by 764 days.

(21) Appl. No.: 12/030,575

(22) Filed: Feb. 13, 2008

(65) Prior Publication Data
US 2009/0004705 A1 Jan. 1, 2009

Related U.S. Application Data

(62) Division of application No. 10/583,191, filed as application No. PCT/EP2004/014337 on Dec. 16, 2004, now abandoned.

(30) Foreign Application Priority Data

Dec. 18, 2003 (DE) .................................. 103 59 660

(51) Int. Cl.
*C12N 15/00* (2006.01)
*C12N 1/20* (2006.01)
(52) U.S. Cl. ..................... 435/320.1; 435/6.1; 435/71.2; 435/252.32
(58) Field of Classification Search ............... 435/320.1, 435/6.1, 71.1, 71.2, 252.32, 477
See application file for complete search history.

(56) References Cited

U.S. PATENT DOCUMENTS

| 4,489,160 | A | 12/1984 | Katsumata et al. |
| 5,158,891 | A | 10/1992 | Takeda et al. |
| 5,965,391 | A | 10/1999 | Reinscheid et al. |
| 6,696,561 | B1 | 2/2004 | Pompejus et al. |
| 6,822,084 | B1 | 11/2004 | Pompejus et al. |
| 7,252,972 | B2 * | 8/2007 | Kikuchi et al. ............ 435/69.8 |
| 2002/0197605 | A1 | 12/2002 | Nakagawa et al. |
| 2004/0180408 | A1 | 9/2004 | Pompejus et al. |

FOREIGN PATENT DOCUMENTS

| DE | 4440118 C1 | 11/1995 |
| EP | 1108790 A2 | 6/2001 |
| WO | WO-01/00804 A2 | 1/2001 |
| WO | WO-02/40679 A2 | 5/2002 |

OTHER PUBLICATIONS

Score search result details for U.S. Appl. No. 10/583,191, Apr. 15, 2011. Result No. 12.*
Brinkrolf K et al., J Biotechnol. Apr. 30, 2007;129(2):191-211. Epub Dec. 20, 2006.The transcriptional regulatory network of the amino acid producer *Corynebacterium glutamicum*.*
Merkamm, Muriel, et al., "Cloning of the *sodA* Gene from *Corynebacterium melassecola* and Role of Superoxide Dismutase in Cellular Viability", Journal of Bacteriology, vol. 183, No. 4, (2001), pp. 1284-1295.
Patek, Miroslav, et al., "Promoters from *Corynebacterium glutamicum*: Cloning, Molecular Analysis and Search for a Consensus Motif", Microbiology, vol. 142, (1996), pp. 1297-1309.
Reinscheid, Dieter J., et al., "Cloning, Sequence Analysis, Expression and Inactivation of the *Corynebacterium glutamicum* pta-ack Operon Encoding Phosphotransacetylase and Acetate Kinase", Microbiology, vol. 145, (1999), pp. 503-513.
Hassett, Daniel J., et al., "Cloning and Characterization of the *Pseudomonas aeruginosa sodA* and *sodB* Genes Encoding Manganese- and Iron-Cofactored Superoxide Dismutase: Demonstration of Increased Manganese Dismutase Activity in Alginate-Producing Bacteria", Journal of Bacteriology, vol. 175, No. 23, (1993), pp. 7658-7665.
Higgins, Deamond G., et al., "Fast and Sensitive Multiple Sequence Alignments on a Microcomputer", Comput. Appl. Biosci., vol. 5, No. 2, (1989), pp. 151-153.
Sambrook, J., et al., "Molecular Cloning: A Laboratory Manual. Second Edition", Cold Spring Harbor Laboratory Press, (1989), pp. 9.31-9.57.
Strauss, William M., "Section II: Hybridization with Radioactive Probes", Current Protocols in Molecular Biology, John Wiley & Sons, N.Y., (1989), pp. 6.3.1-6.3.6.
Voet. "Chapter 28: Nucleic Acid Structures and Manipulation. Section 7: Chemical Synthesis of Oligonucleotides", 2. ed, Viley Press New York, pp. 896-897.
Schäfer, Andreas, et al., "Small Mobilizable Multi-Purpose Cloning Vectors Derived from the *Escherichia coli* Plasmids pK18 and pK19: Selection of Defined Deletions in the Chromosome of *Corynebacterium glutamicum*", Gene, vol. 145, (1994), pp. 69-73.
Blomfield, I.C., et al., "Allelic Exchange in *Escherichia coli* using the *Bacillus subtilis sacB* Gene and a Temperature-Sensitive pSC101 Replicon", Molecular Microbiology, vol. 5, No. 6, (1991), pp. 1447-1457.
Bachmann, A., et al., "Aerobic Biomineralization of Alpha-Hexachlorocyclohexane in Contaminated Soil", Applied and Environmental Microbiology, vol. 54, No. 2, (1988), pp. 548-554.
Eikmanns, Bernhard J., et al., "A Family of *Corynebacterium glutamicum/Escherichia coli* Shuttle Vectors for Cloning, Controlled Gene Expression, and Promoter Probing", Gene, vol. 102, (1991), pp. 93-98.
Sonnen, Hans, at al., "Characterization of pGA1, a New Plasmid from *Corynebacterium glutamicum* LP-6", Gene, vol. 107, (1991), pp. 69-74.
Serwold-Davis, Theresa M., et al., "Localization of an Origin of Replication in *Corynebacterium diphtheriae* Broad Host Range Plasmid pNG2 that also Functions in *Escherichia coli*", FEMS Microbiology Letters, vol. 66, (1990), pp. 119-124.
Reinscheid, Dieter J., et al., "Stable Expression of *hom-1-thrB* in *Corynebacterium glutamicum* and its Effect on the Carbon Flux to Threonine and Related Amino Acids", Applied and Environmental Microbiology, vol. 60, No. 1, (1994), pp. 126-132.

(Continued)

*Primary Examiner* — Maria Leavitt
(74) *Attorney, Agent, or Firm* — Connolly Bove Lodge & Hutz LLP

(57) ABSTRACT

The present invention relates to the use of nucleic acid sequences for regulating the transcription and expression of genes, the novel promoters and expression units themselves, methods for altering or causing the transcription rate and/or expression rate of genes, expression cassettes comprising the expression units, genetically modified microorganisms with altered or caused transcription rate and/or expression rate, and methods for preparing biosynthetic products by cultivating the genetically modified microorganisms.

12 Claims, No Drawings

OTHER PUBLICATIONS

Simon, R., et al., "A Broad Host Range Mobilization System for In Vivo Genetic Engineering: Transposon Mutagenesis in Gram Negative Bacteria", Bio/Technology, vol. 1, (1983), pp. 784-791.

Bernard, Philippe, et al., "The F Plasmid CcdB Protein Induces Efficient ATP-dependent DNA Cleavage by Gyrase", Journal of Molecular Biology, vol. 234, (1993), pp. 534-541.

Schrumpf. B., et al., "A Functionally Split Pathway for Lysine Synthesis in *Corynebacterium glutamicum*", Journal of Bacteriology, vol. 173, No. 14, (1991), pp. 4510-4516.

Spratt, Brian G., et al., "Kanamycin-Resistant Vectors that are Analogues of Plasmids pUC8, pUC9, pEMBL8 and pEMBD9", Gene, vol. 41, (1986), pp. 337-342.

Thierbach, Goorg, et al., "Transformation of Spheroplasts and Protoplasts of *Corynebacterium glutamicum*", Appl. Microbiol. Biotechnol., vol. 29, (1988), pp. 356-362.

Dunican, L. Kieran, et al., "High Frequency Transformation of Whole Cells of Amino Acid Producing Coryneform Bacteria Using High Voltage Electroporation", Bio/Technology, vol. 7, (1989), pp. 1067-1070.

Tauch, Andreas, et al., "*Corynebacterium glutamicum* DNA is Subjected to Methylation-Restriction in *Escherichia coli*", FEMS Microbiology Letters, vol. 123, (1994), pp. 343-348.

Kuninaka, Akira, "15 Nucleotides and Related Compounds", Choshi, Chiba-ken 288, pp. 561-612.

Eggersdorfer, Manfred, et al., "Vitamins", Ullmann's Encyclopedia of Industrial Chemistry, vol. A 27, (1996), pp. 443-613.

"*Corynebacterium melassecola* Peptide Methionine Sulfoxide Reductase A (msrA) and Manganese Superoxide Dismutase (sodA) Genes, Complete Cds.", EBI Database, Accession No. AF236111, Feb. 7, 2001.

"*C. glutamicum* SRT Protein Nucleotide Sequence SEQ ID No. 15", EBI Database, Accession No. AAF70991, Apr. 30, 2001.

"*Corynebacterium glutamicum* Gene for Superoxide Dismutase, Complete Cds.", EBI Database, Accession No. AB055218, Aug. 2, 2001.

"*Corynebacterium glutamicum* ATCC 13032 DNA, Complete Genome", EMBL-EBI Database, Accession No. AP005283, Oct. 26, 2004.

"*C. glutamicum* coding sequence fragment SEQ ID No. 7069", EBI Database, Accession No. AAH68534. Sep. 26. 2001.

Patek, et al., "Promoters from *Corynebacterium glutamicum*," Journal of Biotechnology, vol. 104, Issues 1-3, (2003), pp. 311-323.

Vasicová, et al., "Analysis of the *Corynebacterium glutamicum* dapA promoter," J. Bacteriology, vol. 181, (1999), pp. 6188-6191.

Kennell, Progr Nucleic Acid Res. Mol. Biol., vol. 11, (1971), pp. 259-301.

Menke, E., et al., "Influence of increased aspartate availability on lysine formation by a recombinant strain of *Corynebacterium glutamicum* and utilization of fumarate," Applied and Environmental Microbiology, vol. 55(3), (1989), pp. 684-688.

Tauch, A., et al., "The erythromycin resistance gene of the *Corynebacterium xerosis* R-plasmid pTP10 also carrying chloramphenicol, kanamycin, and tetracycline resistances is capable of transposition in *Corynebacterium glutamicum*," Plasmid, vol. 33, (1995), pp. 168-179.

Patek, et al., "Function of *Corynebacterium glutamicum* promoters in *Escherichia coli, Streptomyces lividans*, and *Bacillus subtilis*," Journal of Biotechnology, vol. 104, (2003), pp. 325-334.

\* cited by examiner

SEQUENCE LISTING

<160> NUMBER OF SEQ ID NOS: 44

<210> SEQ ID NO 1
<211> LENGTH: 173
<212> TYPE: DNA
<213> ORGANISM: Corynebacterium glutamicum
<220> FEATURE:
<223> OTHER INFORMATION: SUPEROXID\DISMUTASE\RXA03119\

<400> SEQUENCE: 1

```
gctgccaatt attccgggct tgtgacccgc tacccgataa ataggtcggc tgaaaaattt      60
cgttgcaata tcaacaaaaa ggcctatcat tgggaggtgt cgcaccaagt acttttgcga     120
agcgccatct gacggatttt caaaagatgt atatgctcgg tgcggaaacc tac            173
```

<210> SEQ ID NO 2
<211> LENGTH: 191
<212> TYPE: DNA
<213> ORGANISM: Corynebacterium glutamicum
<220> FEATURE:
<223> OTHER INFORMATION: SUPEROXID\DISMUTASE\RXA03119\

<400> SEQUENCE: 2

```
agctgccaat tattccgggc ttgtgacccg ctacccgata aataggtcgg ctgaaaaatt      60
tcgttgcaat atcaacaaaa aggcctatca ttgggaggtg tcgcaccaag tacttttgcg     120
aagcgccatc tgacggattt tcaaaagatg tatatgctcg gtgcggaaac ctacgaaagg     180 atttttacc c                                                            191
```

<210> SEQ ID NO 3
<211> LENGTH: 1365
<212> TYPE: DNA
<213> ORGANISM: Corynebacterium glutamicum
<220> FEATURE:
<223> OTHER INFORMATION: RXA00077

<400> SEQUENCE: 3

```
atgaatgatg agaatattca aagctccaac tatcagccat tcccgagttt tgacgattgg      60
aaacagatcg aggtgtcgct cttagatgtc atcgaatcct cacgccattt ttctgatttg     120
```

```
aaagatagca ctgatcgttc tgcgttagat gctgcgctag agagagcaaa aagagctgcc    180
gcagttgata ccaatgccat agaaggaatc ttccaaactg atcgcggttt tacccataca    240
gttgcaacgc aggtaggggc ttgggagcaa caaatggcga tgaaaggcaa acatgttaag    300
cctgcgtttg acgatactct agaaggcttt gagtatgttc tcgatgcagt aactggtaga    360
actccaatct ctcagcaatg gattagaaat ttgcacgccg tcattctgcg gagccaagaa    420
agccacgagg tttttacagc cgttggagtc caaaatcagg cgcttcagaa aggcgagtat    480
aaaactcagc caaatagtcc acagcgctca gatggatctg tacatgcata cgccccagtt    540
gaagatactc ctgctgaaat ggctagattt atttcagaac ttgaatctaa ggaattctta    600
gcagccgaga aggttattca agctgcctat gcccactatg ctttcgtatg tattcatcct    660
tttgcagatg ggaatggacg agttgcacga gccttggcta tgttttttct atacaaagat    720
cctggtgtcc ctctcgtaat ctaccaagat caacgcagag attacatcca tgctctagaa    780
gcagcggaca gaataaaccc gctcctgctg attagattct ttgctgaacg agtgaccgat    840
actattaact ctattatcgt tgatctcact accccgatcg cgggtaaatc tggttcggct    900
aagctttcgg atgcgctacg ccccactcgc gtattaccag aattacatga tgctgcacat    960
aggctccaag aaagtttatt tacagaaatc cgatctcgat tggatgaaga aggaaaaagg    1020
aatgggttgg agtttctact tcaacggatt tttatcggtt ccccattcaa tctgccagag    1080
ggctataacg ctttccctga tagctattgt ctgaccttag ctttcaatag caactctcca    1140
aaacaaatct tccacccgct atccatagta atagcagctc gagatgggaa aagagcgagc    1200
agcgacctcg tggcagctac ttctattgga tacaactttc acgcttacgg acgtgaagtc    1260
gagcctgttg ttactgaaag ctttcgagaa cgtgtgaaaa tttacgccga cgggattgta    1320
gatcacttct taaccgaact ggctaaaaag tttcaacaga attaa                    1365
```

<210> SEQ ID NO 4
<211> LENGTH: 454
<212> TYPE: PRT
<213> ORGANISM: Corynebacterium glutamicum

<400> SEQUENCE: 4

```
Met Asn Asp Glu Asn Ile Gln Ser Ser Asn Tyr Gln Pro Phe Pro Ser
 1               5                  10                  15

Phe Asp Asp Trp Lys Gln Ile Glu Val Ser Leu Leu Asp Val Ile Glu
             20                  25                  30

Ser Ser Arg His Phe Ser Asp Leu Lys Asp Ser Thr Asp Arg Ser Ala
         35                  40                  45

Leu Asp Ala Ala Leu Glu Arg Ala Lys Arg Ala Ala Ala Val Asp Thr
     50                  55                  60

Asn Ala Ile Glu Gly Ile Phe Gln Thr Asp Arg Gly Phe Thr His Thr
 65                  70                  75                  80

Val Ala Thr Gln Val Gly Ala Trp Glu Gln Gln Met Ala Met Lys Gly
                 85                  90                  95

Lys His Val Lys Pro Ala Phe Asp Asp Thr Leu Glu Gly Phe Glu Tyr
            100                 105                 110

Val Leu Asp Ala Val Thr Gly Arg Thr Pro Ile Ser Gln Gln Trp Ile
        115                 120                 125

Arg Asn Leu His Ala Val Ile Leu Arg Ser Gln Glu Ser His Glu Val
    130                 135                 140

Phe Thr Ala Val Gly Val Gln Asn Gln Ala Leu Gln Lys Gly Glu Tyr
145                 150                 155                 160
```

```
Lys Thr Gln Pro Asn Ser Pro Gln Arg Ser Asp Gly Ser Val His Ala
            165                 170                 175

Tyr Ala Pro Val Glu Asp Thr Pro Ala Glu Met Ala Arg Phe Ile Ser
        180                 185                 190

Glu Leu Glu Ser Lys Glu Phe Leu Ala Ala Glu Lys Val Ile Gln Ala
    195                 200                 205

Ala Tyr Ala His Tyr Ala Phe Val Cys Ile His Pro Phe Ala Asp Gly
210                 215                 220

Asn Gly Arg Val Ala Arg Ala Leu Ala Ser Val Phe Leu Tyr Lys Asp
225                 230                 235                 240

Pro Gly Val Pro Leu Val Ile Tyr Gln Asp Gln Arg Arg Asp Tyr Ile
            245                 250                 255

His Ala Leu Glu Ala Ala Asp Lys Asn Asn Pro Leu Leu Leu Ile Arg
        260                 265                 270

Phe Phe Ala Glu Arg Val Thr Asp Thr Ile Asn Ser Ile Ile Val Asp
    275                 280                 285

Leu Thr Thr Pro Ile Ala Gly Lys Ser Gly Ser Ala Lys Leu Ser Asp
    290                 295                 300

Ala Leu Arg Pro Thr Arg Val Leu Pro Glu Leu His Asp Ala Ala His
305                 310                 315                 320

Arg Leu Gln Glu Ser Leu Phe Thr Glu Ile Arg Ser Arg Leu Asp Glu
            325                 330                 335

Glu Gly Lys Arg Asn Gly Leu Glu Phe Leu Leu Gln Arg Ile Phe Ile
        340                 345                 350

Gly Ser Pro Phe Asn Leu Pro Glu Gly Tyr Asn Ala Phe Pro Asp Ser
    355                 360                 365

Tyr Cys Leu Thr Leu Ala Phe Asn Ser Asn Ser Pro Lys Gln Ile Phe
370                 375                 380

His Pro Leu Ser Ile Val Ile Ala Ala Arg Asp Gly Lys Arg Ala Ser
385                 390                 395                 400

Ser Asp Leu Val Ala Ala Thr Ser Ile Gly Tyr Asn Phe His Ala Tyr
            405                 410                 415

Gly Arg Glu Val Glu Pro Val Val Thr Glu Ser Phe Arg Glu Arg Val
        420                 425                 430

Lys Ile Tyr Ala Asp Gly Ile Val Asp His Phe Leu Thr Glu Leu Ala
    435                 440                 445

Lys Lys Phe Gln Gln Asn
    450

<210> SEQ ID NO 5
<211> LENGTH: 35
<212> TYPE: DNA
<213> ORGANISM: Corynebacterium glutamicum
<220> FEATURE:
<223> OTHER INFORMATION: SEQ_ID5

<400> SEQUENCE: 5
gagagagaga cgcgtcccag tggctgagac gcatc                               35

<210> SEQ ID NO 6
<211> LENGTH: 34
<212> TYPE: DNA
<213> ORGANISM: Corynebacterium glutamicum
<220> FEATURE:
<223> OTHER INFORMATION: SEQ_ID_6

<400> SEQUENCE: 6
ctctctctgt cgacgaattc aatcttacgg cctg                                34
```

<210> SEQ ID NO 7
<211> LENGTH: 4323
<212> TYPE: DNA
<213> ORGANISM: Corynebacterium glutamicum
<220> FEATURE:
<223> OTHER INFORMATION: SEQ_ID_7
<220> FEATURE:
<221> NAME/KEY: misc_feature
<222> LOCATION: (457)..(1248)
<223> OTHER INFORMATION: KanR
<220> FEATURE:
<221> NAME/KEY: misc_feature
<222> LOCATION: (1515)..(2375)
<223> OTHER INFORMATION: Ori-EC  (pMB)
<220> FEATURE:
<221> NAME/KEY: misc_feature
<222> LOCATION: (1515)..(2375)
<223> OTHER INFORMATION: Ori-EC  (pMB)  complement
<220> FEATURE:
<221> NAME/KEY: misc_feature
<222> LOCATION: (2418)..(3839)
<223> OTHER INFORMATION: SacB  complement
<220> FEATURE:
<221> NAME/KEY: misc_feature
<222> LOCATION: (3840)..(4302)
<223> OTHER INFORMATION: PsacB  complement

<400> SEQUENCE: 7

```
tcgagaggcc tgacgtcggg cccggtacca cgcgtcatat gactagttcg gacctaggga      60
tatcgtcgac atcgatgctc ttctgcgtta attaacaatt gggatcctct agacccggga     120
tttaaatcgc tagcgggctg ctaaaggaag cggaacacgt agaaagccag tccgcagaaa     180
cggtgctgac cccggatgaa tgtcagctac tgggctatct ggacaaggga aaacgcaagc     240
gcaaagagaa agcaggtagc ttgcagtggg cttacatggc gatagctaga ctgggcggtt     300
ttatggacag caagcgaacc ggaattgcca gctggggcgc cctctggtaa ggttgggaag     360
ccctgcaaag taaactggat ggctttcttg ccgccaagga tctgatgcg caggggatca      420
agatctgatc aagagacagg atgaggatcg tttcgcatga ttgaacaaga tggattgcac     480
gcaggttctc cggccgcttg ggtggagagg ctattcggct atgactgggc acaacagaca     540
atcggctgct ctgatgccgc cgtgttccgg ctgtcagcgc agggggcgccc ggttcttttt    600
gtcaagaccg acctgtccgg tgccctgaat gaactgcagg acgaggcagc gcggctatcg     660
tggctggcca cgacgggcgt tccttgcgca gctgtgctcg acgttgtcac tgaagcggga     720
agggactggc tgctattggg cgaagtgccg gggcaggatc tcctgtcatc tcaccttgct     780
cctgccgaga aagtatccat catggctgat gcaatgcggc ggctgcatac gcttgatccg     840
gctacctgcc cattcgacca ccaagcgaaa catcgcatcg agcgagcacg tactcggatg     900
gaagccggtc ttgtcgatca ggatgatctg gacgaagagc atcaggggct cgcgccagcc     960
gaactgttcg ccaggctcaa ggcgcgcatg cccgacggcg aggatctcgt cgtgacccat    1020
ggcgatgcct gcttgccgaa tatcatggtg gaaaatggcc gcttttctgg attcatcgac    1080
tgtggccggc tgggtgtggc ggaccgctat caggacatag cgttggctac ccgtgatatt    1140
gctgaagagc ttggcggcga atgggctgac cgcttcctcg tgctttacgg tatcgccgct    1200
cccgattcgc agcgcatcgc cttctatcgc cttcttgacg agttcttctg agcgggactc    1260
tggggttcga aatgaccgac caagcgacgc ccaacctgcc atcacgagat ttcgattcca    1320
ccgccgcctt ctatgaaagg ttgggcttcg gaatcgtttt ccgggacgcc ggctggatga    1380
tcctccagcg cggggatctc atgctggagt tcttcgccca cgctagcggc gcgccggcc     1440
gcccggtgtg aaataccgca cagatgcgta aggagaaaat accgcatcag gcgctcttcc    1500
```

```
gcttcctcgc tcactgactc gctgcgctcg gtcgttcggc tgcggcgagc ggtatcagct    1560
cactcaaagg cggtaatacg gttatccaca gaatcagggg ataacgcagg aaagaacatg    1620
tgagcaaaag gccagcaaaa ggccaggaac cgtaaaaagg ccgcgttgct ggcgttttc     1680 cataggctcc gcccccctga cgagcatcac aaaaatcgac gctcaagtca gaggtggcga    1740
aacccgacag gactataaag ataccaggcg tttccccctg gaagctccct cgtgcgctct    1800
cctgttccga ccctgccgct taccggatac ctgtccgcct ttctcccttc gggaagcgtg    1860
gcgctttctc atagctcacg ctgtaggtat ctcagttcgg tgtaggtcgt tcgctccaag    1920
ctgggctgtg tgcacgaacc ccccgttcag cccgaccgct gcgccttatc cggtaactat    1980
cgtcttgagt ccaacccggt aagacacgac ttatcgccac tggcagcagc cactggtaac    2040
aggattagca gagcgaggta tgtaggcggt gctacagagt tcttgaagtg gtggcctaac    2100
tacggctaca ctagaaggac agtatttggt atctgcgctc tgctgaagcc agttaccttc    2160
ggaaaaagag ttggtagctc ttgatccggc aaacaaacca ccgctggtag cggtggtttt    2220
tttgtttgca agcagcagat tacgcgcaga aaaaaggat ctcaagaaga tcctttgatc     2280
ttttctacgg ggtctgacgc tcagtggaac gaaaactcac gttaagggat tttggtcatg    2340
agattatcaa aaaggatctt cacctagatc cttttaaagg ccggccgcgg ccgccatcgg    2400 catttctt tgcgttttta tttgttaact gttaattgtc cttgttcaag gatgctgtct       2460
ttgacaacag atgttttctt gcctttgatg ttcagcagga agctcggcgc aaacgttgat    2520
tgtttgtctg cgtagaatcc tctgtttgtc atatagcttg taatcacgac attgtttcct    2580
ttcgcttgag gtacagcgaa gtgtgagtaa gtaaggtta catcgttagg atcaagatcc     2640 attttaaca caaggccagt tttgttcagc ggcttgtatg ggccagttaa gaattagaa       2700 acataaccaa gcatgtaaat atcgttagac gtaatgccgt caatcgtcat ttttgatccg    2760
cgggagtcag tgaacaggta ccatttgccg ttcattttaa agacgttcgc gcgttcaatt    2820
tcatctgtta ctgtgttaga tgcaatcagc ggtttcatca ctttttcag tgtgtaatca     2880 tcgtttagct caatcatacc gagagcgccg tttgctaact cagccgtgcg ttttttatcg    2940
ctttgcagaa gttttttgact tcttgacgg aagaatgatg tgcttttgcc atagtatgct    3000
ttgttaaata aagattcttc gccttggtag ccatcttcag ttccagtgtt tgcttcaaat    3060
actaagtatt tgtggccttt atcttctacg tagtgaggat ctctcagcgt atggttgtcg    3120
cctgagctgt agttgccttc atcgatgaac tgctgtacat tttgatacgt ttttccgtca    3180
ccgtcaaaga ttgatttata atcctctaca ccgttgatgt tcaaagagct gtctgatgct    3240
gatacgttaa cttgtgcagt tgtcagtgtt tgtttgccgt aatgtttacc ggagaaatca    3300
gtgtagaata aacggatttt tccgtcagat gtaaatgtgg ctgaacctga ccattcttgt    3360
gtttggtctt ttaggataga atcatttgca tcgaatttgt cgctgtcttt aaagacgcgg    3420
ccagcgtttt tccagctgtc aatagaagtt tcgccgactt tttgatagaa catgtaaatc    3480
gatgtgtcat ccgcattttt aggatctccg gctaatgcaa agacgatgtg gtagccgtga    3540
tagtttgcga cagtgccgtc agcgttttgt aatggccagc tgtcccaaac gtccaggcct    3600
tttgcagaag agatattttt aattgtggac gaatcaaatt cagaaacttg atatttttca    3660
tttttttgct gttcagggat ttgcagcata tcatggcgtg taatatggga aatgccgtat    3720
gtttccttat atggctttg gttcgtttct ttcgcaaacg cttgagttgc gcctcctgcc      3780
agcagtgcgg tagtaaaggt taatactgtt gcttgttttg caaacttttt gatgttcatc    3840
gttcatgtct ccttttttat gtactgtgtt agcggtctgc ttcttccagc cctcctgttt    3900
```

```
gaagatggca agttagttac gcacaataaa aaaagaccta aaatatgtaa ggggtgacgc    3960
caaagtatac actttgccct ttacacattt taggtcttgc ctgctttatc agtaacaaac    4020
ccgcgcgatt tacttttcga cctcattcta ttagactctc gtttggattg caactggtct    4080
attttcctct tttgtttgat agaaaatcat aaaaggattt gcagactacg ggcctaaaga    4140
actaaaaaat ctatctgttt cttttcattc tctgtatttt ttatagtttc tgttgcatgg    4200
gcataaagtt gccttttttaa tcacaattca gaaaatatca taatatctca tttcactaaa    4260
taatagtgaa cggcaggtat atgtgatggg ttaaaaagga tcggcggccg ctcgatttaa    4320
atc                                                                  4323

<210> SEQ ID NO 8
<211> LENGTH: 5860
<212> TYPE: DNA
<213> ORGANISM: Corynebacterium glutamicum
<220> FEATURE:
<223> OTHER INFORMATION: PCIS\LYSC
<220> FEATURE:
<221> NAME/KEY: misc_feature
<222> LOCATION: (155)..(1420)
<223> OTHER INFORMATION: lysC
<220> FEATURE:
<221> NAME/KEY: misc_feature
<222> LOCATION: (1974)..(2765)
<223> OTHER INFORMATION: KanR
<220> FEATURE:
<221> NAME/KEY: misc_feature
<222> LOCATION: (3032)..(3892)
<223> OTHER INFORMATION: Ori-EC   complement
<220> FEATURE:
<221> NAME/KEY: misc_feature
<222> LOCATION: (3913)..(3934)
<223> OTHER INFORMATION: sacB downstream complement
<220> FEATURE:
<221> NAME/KEY: misc_feature
<222> LOCATION: (3935)..(5356)
<223> OTHER INFORMATION: sacB  (Bacillus Subtilis) complement
<220> FEATURE:
<221> NAME/KEY: misc_feature
<222> LOCATION: (5357)..(5819)
<223> OTHER INFORMATION: Promotor sacB  complement

<400> SEQUENCE: 8
cccggtacca cgcgtcccag tggctgagac gcatccgcta aagccccagg aaccctgtgc     60
agaaagaaaa cactcctctg gctaggtaga cacagtttat aaaggtagag ttgagcgggt    120
aactgtcagc acgtagatcg aaaggtgcac aaaggtggcc ctggtcgtac agaaatatgg    180
cggttcctcg cttgagagtg cggaacgcat tagaaacgtc gctgaacgga tcgttgccac    240
caagaaggct ggaaatgatg tcgtggttgt ctgctccgca atgggagaca ccacggatga    300
acttctagaa cttgcagcgg cagtgaatcc cgttccgcca gctcgtgaaa tggatatgct    360
cctgactgct ggtgagcgta tttctaacgc tctcgtcgcc atggctattg agtcccttgg    420
cgcagaagcc caatctttca cgggctctca ggctggtgtg ctcaccaccg agcgccacgg    480
aaacgcacgc attgttgatg tcactccagg tcgtgtgcgt gaagcactcg atgagggcaa    540
gatctgcatt gttgctggtt tccagggtgt taataaagaa accgcgatg tcaccacgtt    600 gggtcgtggt ggttctgaca ccactgcagt tgcgttggca gctgctttga acgctgatgt    660
gtgtgagatt tactcggacg ttgacggtgt gtataccgct gacccgcgca tcgttcctaa    720
tgcacagaag ctggaaaagc tcagcttcga gaaaatgctg gaacttgctg ctgttggctc    780 caagatttttg gtgctgcgca gtgttgaata cgctcgtgca ttcaatgtgc acttcgcgt    840 acgctcgtct tatagtaatg atcccggcac tttgattgcc ggctctatgg aggatattcc    900
```

```
tgtggaagaa gcagtcctta ccggtgtcgc aaccgacaag tccgaagcca aagtaaccgt    960
tctgggtatt tccgataagc caggcgaggc tgcgaaggtt ttccgtgcgt tggctgatgc   1020
agaaatcaac attgacatgg ttctgcagaa cgtctcttct gtagaagacg caccaccga   1080 catcaccttc acctgccctc gttccgacgg ccgccgcgcg atggagatct tgaagaagct   1140
tcaggttcag ggcaactgga ccaatgtgct tacgacgac caggtcggca aagtctccct    1200
cgtgggtgct ggcatgaagt ctcacccagg tgttaccgca gagttcatgg aagctctgcg   1260
cgatgtcaac gtgaacatcg aattgatttc cacctctgag attcgtattt ccgtgctgat   1320
ccgtgaagat gatctggatg ctgctgcacg tgcattgcat gagcagttcc agctgggcgg   1380
cgaagacgaa gccgtcgttt atgcaggcac cggacgctaa agttttaaag gagtagtttt   1440
acaatgacca ccatcgcagt tgttggtgca accggccagg tcggccaggt tatgcgcacc   1500
cttttggaag agcgcaattt cccagctgac actgttcgtt tctttgcttc cccacgttcc   1560
gcaggccgta agattgaatt cgtcgacatc gatgctcttc tgcgttaatt aacaattggg   1620
atcctctaga cccgggattt aaatcgctag cgggctgcta aaggaagcgg aacacgtaga   1680
aagccagtcc gcagaaacgg tgctgacccc ggatgaatgt cagctactgg gctatctgga   1740
caagggaaaa cgcaagcgca aagagaaagc aggtagcttg cagtgggctt acatggcgat   1800
agctagactg ggcggtttta tggacagcaa gcgaaccgga attgccagct ggggcgccct   1860
ctggtaaggt tgggaagccc tgcaaagtaa actggatggc tttcttgccg ccaaggatct   1920
gatggcgcag gggatcaaga tctgatcaag agacaggatg aggatcgttt cgcatgattg   1980
aacaagatgg attgcacgca ggttctccgg ccgcttgggt ggagaggcta ttcggctatg   2040
actgggcaca acagacaatc ggctgctctg atgccgccgt gttccggctg tcagcgcagg   2100
ggcgcccggt tctttttgtc aagaccgacc tgtccggtgc cctgaatgaa ctgcaggacg   2160
aggcagcgcg gctatcgtgg ctggccacga cgggcgttcc ttgcgcagct gtgctcgacg   2220
ttgtcactga agcgggaagg gactggctgc tattgggcga agtgccgggg caggatctcc   2280
tgtcatctca ccttgctcct gccgagaaag tatccatcat ggctgatgca atgcggcggc   2340
tgcatacgct tgatccggct acctgcccat tcgaccacca agcgaaacat cgcatcgagc   2400
gagcacgtac tcggatggaa gccggtcttg tcgatcagga tgatctggac gaagagcatc   2460
aggggctcgc gccagccgaa ctgttcgcca ggctcaaggc gcgcatgccc gacggcgagg   2520
atctcgtcgt gacccatggc gatgcctgct tgccgaatat catggtggaa aatggccgct   2580
tttctggatt catcgactgt ggccggctgg gtgtggcgga ccgctatcag gacatagcgt   2640
tggctacccg tgatattgct gaagagcttg gcggcgaatg ggctgaccgc ttcctcgtgc   2700
tttacggtat cgccgctccc gattcgcagc gcatcgcctt ctatcgcctt cttgacgagt   2760
tcttctgagc gggactctgg ggttcgaaat gaccgaccaa gcgacgccca acctgccatc   2820
acgagatttc gattccaccg ccgccttcta tgaaaggttg gcttcggaa tcgttttccg   2880 ggacgccggc tggatgatcc tccagcgcgg ggatctcatg ctggagttct cgcccacgc   2940 tagcggcgcg ccgccggcc cggtgtgaaa taccgcacag atgcgtaagg agaaaatacc   3000
gcatcaggcg ctcttccgct tcctcgctca ctgactcgct gcgctcggtc gttcggctgc   3060
ggcgagcggt atcagctcac tcaaaggcgg taatacggtt atccacagaa tcaggggata   3120
acgcaggaaa gaacatgtga gcaaaaggcc agcaaaaggc caggaaccgt aaaaaggccg   3180
cgttgctggc gtttttccat aggctccgcc ccctgacga gcatcacaaa aatcgacgct   3240
caagtcagag gtggcgaaac ccgacaggac tataaagata ccaggcgttt ccccctggaa   3300
```

```
gctccctcgt gcgctctcct gttccgaccc tgccgcttac cggatacctg tccgcctttc    3360
tcccttcggg aagcgtggcg ctttctcata gctcacgctg taggtatctc agttcggtgt    3420
aggtcgttcg ctccaagctg ggctgtgtgc acgaacccc cgttcagccc gaccgctgcg      3480
ccttatccgg taactatcgt cttgagtcca acccggtaag acacgactta tcgccactgg    3540
cagcagccac tggtaacagg attagcagag cgaggtatgt aggcggtgct acagagttct    3600
tgaagtggtg gcctaactac ggctacacta gaaggacagt atttggtatc tgcgctctgc    3660
tgaagccagt taccttcgga aaagagttg gtagctcttg atccggcaaa caaaccaccg     3720
ctggtagcgg tggttttttt gtttgcaagc agcagattac gcgcagaaaa aaaggatctc    3780
aagaagatcc tttgatcttt tctacggggt ctgacgctca gtggaacgaa aactcacgtt    3840
aagggatttt ggtcatgaga ttatcaaaaa ggatcttcac ctagatcctt ttaaaggccg    3900
gccgcggccg ccatcggcat tttcttttgc gttttatttt gttaactgtt aattgtcctt    3960
gttcaaggat gctgtctttg acaacagatg ttttcttgcc tttgatgttc agcaggaagc    4020
tcggcgcaaa cgttgattgt tgtctgcgt agaatcctct gtttgtcata tagcttgtaa     4080
tcacgacatt gtttccttc gcttgaggta cagcgaagtg tgagtaagta aaggttacat      4140
cgttaggatc aagatccatt tttaacacaa ggccagtttt gttcagcggc ttgtatgggc    4200
cagttaaaga attagaaaca taaccaagca tgtaaatatc gttagacgta atgccgtcaa    4260
tcgtcatttt tgatccgcgg gagtcagtga acaggtacca tttgccgttc attttaaaga    4320
cgttcgcgcg ttcaatttca tctgttactg tgttagatgc aatcagcggt ttcatcactt    4380
ttttcagtgt gtaatcatcg tttagctcaa tcataccgag agcgccgttt gctaactcag    4440
ccgtgcgttt tttatcgctt tgcagaagtt tttgactttc ttgacggaag aatgatgtgc    4500
ttttgccata gtatgctttg ttaaataaag attcttcgcc ttggtagcca tcttcagttc    4560
cagtgtttgc ttcaaatact aagtatttgt ggcctttatc ttctacgtag tgaggatctc    4620
tcagcgtatg gttgtcgcct gagctgtagt tgccttcatc gatgaactgc tgtacatttt    4680
gatacgtttt tccgtcaccg tcaaagattg atttataatc ctctacaccg ttgatgttca    4740
aagagctgtc tgatgctgat acgttaactt gtgcagttgt cagtgtttgt ttgccgtaat    4800
gtttaccgga gaaatcagtg tagaataaac ggattttccc gtcagatgta aatgtggctg    4860
aacctgacca ttcttgtgtt tggtctttta ggatagaatc atttgcatcg aatttgtcgc    4920
tgtctttaaa gacgcggcca gcgttttcc agctgtcaat agaagtttcg ccgacttttt     4980
gatagaacat gtaaatcgat gtgtcatccg cattttagg atctccggct aatgcaaaga     5040
cgatgtggta gccgtgatag tttgcgacag tgccgtcagc gttttgtaat ggccagctgt    5100
cccaaacgtc caggcctttt gcagaagaga tatttttaat tgtggacgaa tcaaattcag    5160
aaacttgata ttttttcattt ttttgctgtt cagggatttg cagcatatca tggcgtgtaa    5220
tatgggaaat gccgtatgtt tccttatatg gcttttggtt cgtttctttc gcaaacgctt    5280
gagttgcgcc tcctgccagc agtgcggtag taaaggttaa tactgttgct tgttttgcaa    5340
actttttgat gttcatcgtt catgtctcct ttttttatgta ctgtgttagc ggtctgcttc   5400
ttccagccct cctgtttgaa gatggcaagt tagttacgca caataaaaaa agacctaaaa    5460
tatgtaaggg gtgacgccaa agtatacact ttgccctta cacattttag gtcttgcctg    5520
ctttatcagt aacaaacccg cgcgatttac ttttcgacct cattctatta gactctcgtt    5580
tggattgcaa ctggtctatt ttcctctttt gtttgataga aaatcataaa aggatttgca    5640
gactacgggc ctaaagaact aaaaaatcta tctgtttctt ttcattctct gtatttttta    5700
```

```
tagtttctgt tgcatgggca taaagttgcc tttttaatca caattcagaa aatatcataa      5760
tatctcattt cactaaataa tagtgaacgg caggtatatg tgatgggtta aaaaggatcg      5820
gcggccgctc gatttaaatc tcgagaggcc tgacgtcggg                            5860

<210> SEQ ID NO 9
<211> LENGTH: 38
<212> TYPE: DNA
<213> ORGANISM: Corynebacterium glutamicum
<220> FEATURE:
<223> OTHER INFORMATION: SEQ_ID_9

<400> SEQUENCE: 9
cggcaccacc gacatcatct tcacctgccc tcgttccg                                38

<210> SEQ ID NO 10
<211> LENGTH: 38
<212> TYPE: DNA
<213> ORGANISM: Corynebacterium glutamicum
<220> FEATURE:
<223> OTHER INFORMATION: SEQ_ID_10

<400> SEQUENCE: 10
cggaacgagg gcaggtgaag atgatgtcgg tggtgccg                                38

<210> SEQ ID NO 11
<211> LENGTH: 1263
<212> TYPE: DNA
<213> ORGANISM: Corynebacterium glutamicum
<220> FEATURE:
<223> OTHER INFORMATION: LYSC-GEN

<400> SEQUENCE: 11
gtggccctgg tcgtacagaa atatggcggt tcctcgcttg agagtgcgga acgcattaga        60
aacgtcgctg aacggatcgt tgccaccaag aaggctggaa atgatgtcgt ggttgtctgc       120
tccgcaatgg gagacaccac ggatgaactt ctagaacttg cagcggcagt gaatcccgtt       180
ccgccagctc gtgaaatgga tatgctcctg actgctggtg agcgtatttc taacgctctc       240
gtcgccatgg ctattgagtc ccttggcgca gaagcccaat cttcacggg ctctcaggct       300 ggtgtgctca ccaccgagcg ccacggaaac gcacgcattg ttgatgtcac tccaggtcgt       360
gtgcgtgaag cactcgatga gggcaagatc tgcattgttg ctggtttcca gggtgttaat       420
aaagaaaccc gcgatgtcac cacgttgggt cgtggtggtt ctgacaccac tgcagttgcg       480
ttggcagctg ctttgaacgc tgatgtgtgt gagatttact cggacgttga cggtgtgtat       540
accgctgacc cgcgcatcgt tcctaatgca cagaagctgg aaaagctcag cttcgaagaa       600
atgctggaac ttgctgctgt tggctccaag atttttggtg cgcgcagtgt tgaatacgct       660
cgtgcattca atgtgccact tcgcgtacgc tcgtcttata gtaatgatcc cggcactttg       720
attgccggct ctatggagga tattcctgtg aagaagcag tccttaccgg tgtcgcaacc       780
gacaagtccg aagccaaagt aaccgttctg ggtatttccg ataagccagg cgaggctgcg       840
aaggttttcc gtgcgttggc tgatgcagaa atcaacattg acatggttct gcagaacgtc       900
tcttctgtag aagacggcac caccgacatc accttcacct gccctcgttc gacggccgc       960 cgcgcgatgg agatcttgaa gaagcttcag gttcagggca actggaccaa tgtgctttac      1020
gacgaccagg tcggcaaagt ctccctcgtg ggtgctggca tgaagtctca cccaggtgtt      1080
accgcagagt tcatgaaagc tctgcgcgat gtcaacgtga acatcgaatt gatttccacc      1140
tctgagattc gtatttccgt gctgatccgt gaagatgatc tggatgctgc tgcacgtgca      1200
```
ttgcatgagc agttccagct gggcggcgaa gacgaagccg tcgtttatgc aggcaccgga    1260
cgc                                                                 1263

<210> SEQ ID NO 12
<211> LENGTH: 5860
<212> TYPE: DNA
<213> ORGANISM: Corynebacterium glutamicum
<220> FEATURE:
<223> OTHER INFORMATION: PCIS\LYSC\THR311ILE
<220> FEATURE:
<221> NAME/KEY: misc_feature
<222> LOCATION: (155)..(1420)
<223> OTHER INFORMATION: LysC
<220> FEATURE:
<221> NAME/KEY: misc_feature
<222> LOCATION: (1974)..(2765)
<223> OTHER INFORMATION: KanR
<220> FEATURE:
<221> NAME/KEY: misc_feature
<222> LOCATION: (3032)..(3892)
<223> OTHER INFORMATION: Ori-EC (pMB)
<220> FEATURE:
<221> NAME/KEY: misc_feature
<222> LOCATION: (3913)..(3934)
<223> OTHER INFORMATION: C_region : sacB downstream   (complement)
<220> FEATURE:
<221> NAME/KEY: misc_feature
<222> LOCATION: (3935)..(5356)
<223> OTHER INFORMATION: sacB  Bacillus Subtilis    (complement)
<220> FEATURE:
<221> NAME/KEY: misc_feature
<222> LOCATION: (5357)..(5819)
<223> OTHER INFORMATION: Promotor sacB   (complement)

<400> SEQUENCE: 12
cccggtacca cgcgtcccag tggctgagac gcatccgcta aagccccagg aaccctgtgc      60
agaaagaaaa cactcctctg gctaggtaga cacagtttat aaaggtagag ttgagcgggt     120
aactgtcagc acgtagatcg aaaggtgcac aaaggtggcc ctggtcgtac agaaatatgg     180
cggttcctcg cttgagagtg cggaacgcat tagaaacgtc gctgaacgga tcgttgccac     240
caagaaggct ggaaatgatg tcgtggttgt ctgctccgca atgggagaca ccacggatga     300
acttctagaa cttgcagcgg cagtgaatcc cgttccgcca gctcgtgaaa tggatatgct     360
cctgactgct ggtgagcgta tttctaacgc tctcgtcgcc atggctattg agtcccttgg     420
cgcagaagcc caatctttca cgggctctca ggctggtgtg ctcaccaccg agcgccacgg     480
aaacgcacgc attgttgatg tcactccagg tcgtgtgcgt gaagcactcg atgagggcaa     540
gatctgcatt gttgctggtt tccagggtgt taataaagaa accgcgatgt caccacgtt      600 gggtcgtggt ggttctgaca ccactgcagt tgcgttggca gctgctttga acgctgatgt     660
gtgtgagatt tactcggacg ttgacggtgt gtataccgct gacccgcgca tcgttcctaa     720
tgcacagaag ctggaaaagc tcagcttcga agaaatgctg gaacttgctg ctgttggctc     780 caagatttg gtgctgcgca gtgttgaata cgctcgtgca ttcaatgtgc cacttcgcgt     840
acgctcgtct tatagtaatg atcccggcac tttgattgcc ggctctatgg aggatattcc     900
tgtggaagaa gcagtcctta ccggtgtcgc aaccgacaag tccgaagcca agtaaaccgt     960
tctgggtatt ccgataagc caggcgaggc tgcgaaggtt ttccgtgcgt ggctgatgc     1020 agaaatcaac attgacatgg ttctgcagaa cgtctcttct gtagaagacg gcaccaccga    1080
catcatcttc acctgccctc gttccgacgg ccgccgcgcg atggagatct gaagaagct     1140 tcaggttcag ggcaactgga ccaatgtgct ttacgacgac caggtcggca agtctccct    1200 cgtgggtgct ggcatgaagt ctcacccagg tgttaccgca gagttcatgg aagctctgcg    1260

```
cgatgtcaac gtgaacatcg aattgatttc cacctctgag attcgtattt ccgtgctgat    1320
ccgtgaagat gatctggatg ctgctgcacg tgcattgcat gagcagttcc agctgggcgg    1380
cgaagacgaa gccgtcgttt atgcaggcac cggacgctaa agttttaaag gagtagtttt    1440
acaatgacca ccatcgcagt tgttggtgca accggccagg tcggccaggt tatgcgcacc    1500
cttttggaag agcgcaattt cccagctgac actgttcgtt tctttgcttc cccacgttcc    1560
gcaggccgta agattgaatt cgtcgacatc gatgctcttc tgcgttaatt aacaattggg    1620
atcctctaga cccgggattt aaatcgctag cgggctgcta aaggaagcgg aacacgtaga    1680
aagccagtcc gcagaaacgg tgctgacccc ggatgaatgt cagctactgg gctatctgga    1740
caagggaaaa cgcaagcgca aagagaaagc aggtagcttg cagtgggctt acatggcgat    1800
agctagactg ggcggtttta tggacagcaa gcgaaccgga attgccagct ggggcgccct    1860
ctggtaaggt tgggaagccc tgcaaagtaa actggatggc tttcttgccg ccaaggatct    1920 gatgcgcag gggatcaaga tctgatcaag agacaggatg aggatcgttt cgcatgattg    1980
aacaagatgg attgcacgca ggttctccgg ccgcttgggt ggagaggcta ttcggctatg    2040
actgggcaca acagacaatc ggctgctctg atgccgccgt gttccggctg tcagcgcagg    2100
ggcgcccggt tctttttgtc aagaccgacc tgtccggtgc cctgaatgaa ctgcaggacg    2160
aggcagcgcg gctatcgtgg ctggccacga cgggcgttcc ttgcgcagct gtgctcgacg    2220
ttgtcactga agcgggaagg gactggctgc tattgggcga agtgccgggg caggatctcc    2280
tgtcatctca ccttgctcct gccgagaaag tatccatcat ggctgatgca atgcggcggc    2340
tgcatacgct tgatccggct acctgcccat tcgaccacca agcgaaacat cgcatcgagc    2400
gagcacgtac tcggatggaa gccggtcttg tcgatcagga tgatctggac gaagagcatc    2460
aggggctcgc gccagccgaa ctgttcgcca ggctcaaggc gcgcatgccc gacggcgagg    2520
atctcgtcgt gacccatggc gatgcctgct tgccgaatat catggtggaa aatggccgct    2580
tttctggatt catcgactgt ggccggctgg gtgtggcgga ccgctatcag gacatagcgt    2640
tggctacccg tgatattgct gaagagcttg gcggcgaatg ggctgaccgc ttcctcgtgc    2700
tttacggtat cgccgctccc gattcgcagc gcatcgcctt ctatcgcctt cttgacgagt    2760
tcttctgagc gggactctgg ggttcgaaat gaccgaccaa gcgacgccca acctgccatc    2820
acgagatttc gattccaccg ccgccttcta tgaaaggttg gcttcggaa tcgttttccg    2880 ggacgccggc tggatgatcc tccagcgcgg ggatctcatg ctggagttct cgcccacgc    2940 tagcggcgcg ccggccggcc cggtgtgaaa taccgcacag atgcgtaagg agaaaatacc    3000
gcatcaggcg ctcttccgct tcctcgctca ctgactcgct gcgctcggtc gttcggctgc    3060
ggcgagcggt atcagctcac tcaaaggcgg taatacggtt atccacagaa tcaggggata    3120
acgcaggaaa gaacatgtga gcaaaaggcc agcaaaaggc caggaaccgt aaaaaggccg    3180
cgttgctggc gtttttccat aggctccgcc cccctgacga gcatcacaaa aatcgacgct    3240
caagtcagag gtggcgaaac ccgacaggac tataaagata ccaggcgttt ccccctggaa    3300
gctccctcgt gcgctctcct gttccgaccc tgccgcttac cggatacctg tccgcctttc    3360
tcccttcggg aagcgtggcg ctttctcata gctcacgctg taggtatctc agttcggtgt    3420
aggtcgttcg ctccaagctg ggctgtgtgc acgaaccccc cgttcagccc gaccgctgcg    3480
ccttatccgg taactatcgt cttgagtcca acccggtaag acacgactta tcgccactgg    3540
cagcagccac tggtaacagg attagcagag cgaggtatgt aggcggtgct acagagttct    3600
tgaagtggtg gcctaactac ggctacacta gaaggacagt atttggtatc tgcgctctgc    3660
```

```
tgaagccagt taccttcgga aaaagagttg gtagctcttg atccggcaaa caaaccaccg   3720
ctggtagcgg tggttttttt gtttgcaagc agcagattac gcgcagaaaa aaaggatctc   3780
aagaagatcc tttgatcttt tctacggggt ctgacgctca gtggaacgaa aactcacgtt   3840
aagggatttt ggtcatgaga ttatcaaaaa ggatcttcac ctagatcctt ttaaaggccg   3900
gccgcggccg ccatcggcat tttcttttgc gttttatt tgttaactgtt aattgtcctt   3960 gttcaaggat gctgtctttg acaacagatg ttttcttgcc tttgatgttc agcaggaagc   4020
tcggcgcaaa cgttgattgt ttgtctgcgt agaatcctct gtttgtcata tagcttgtaa   4080
tcacgacatt gtttccttc gcttgaggta cagcgaagtg tgagtaagta aaggttacat   4140
cgttaggatc aagatccatt tttaacacaa ggccagtttt gttcagcggc ttgtatgggc   4200
cagttaaaga attagaaaca taaccaagca tgtaaatatc gttagacgta atgccgtcaa   4260
tcgtcatttt tgatccgcgg gagtcagtga acaggtacca tttgccgttc attttaaaga   4320
cgttcgcgcg ttcaattca tctgttactg tgttagatgc aatcagcggt ttcatcactt   4380
ttttcagtgt gtaatcatcg tttagctcaa tcataccgag agcgccgttt gctaactcag   4440
ccgtgcgttt tttatcgctt tgcagaagtt tttgactttc ttgacggaag aatgatgtgc   4500
ttttgccata gtatgctttg ttaaataaag attcttcgcc ttggtagcca tcttcagttc   4560
cagtgtttgc ttcaaatact aagtatttgt ggcctttatc ttctacgtag tgaggatctc   4620
tcagcgtatg gttgtcgcct gagctgtagt tgccttcatc gatgaactgc tgtacatttt   4680
gatacgtttt tccgtcaccg tcaaagattg atttataatc ctctacaccg ttgatgttca   4740
aagagctgtc tgatgctgat acgttaactt gtgcagttgt cagtgtttgt ttgccgtaat   4800
gtttaccgga gaaatcagtg tagaataaac ggattttccc gtcagatgta atgtggctg   4860 aacctgacca ttcttgtgtt tggtctttta ggatagaatc atttgcatcg aatttgtcgc   4920
tgtctttaaa gacgcggcca gcgttttcc agctgtcaat agaagtttcg ccgacttttt   4980
gatagaacat gtaaatcgat gtgtcatccg cattttagg atctccggct aatgcaaaga   5040
cgatgtggta gccgtgatag tttgcgacag tgccgtcagc gttttgtaat ggccagctgt   5100
cccaaacgtc caggccttt gcagaagaga tatttttaat tgtggacgaa tcaaattcag   5160
aaacttgata ttttccattt ttttgctgtt cagggatttg cagcatatca tggcgtgtaa   5220
tatgggaaat gccgtatgtt tccttatatg gcttttggtt cgtttctttc gcaaacgctt   5280
gagttgcgcc tcctgccagc agtgcggtag taaaggttaa tactgttgct tgttttgcaa   5340 acttttgat gttcatcgtt catgtctcct ttttttatgta ctgtgttagc ggtctgcttc   5400
ttccagccct cctgtttgaa gatggcaagt tagttacgca aataaaaaa agacctaaaa   5460 tatgtaaggg gtgacgccaa agtatacact ttgcccttta cacattttag gtcttgcctg   5520
ctttatcagt aacaaacccg cgcgatttac ttttcgacct cattctatta gactctcgtt   5580
tggattgcaa ctggtctatt ttcctctttt gtttgataga aaatcataaa aggatttgca   5640
gactacgggc ctaaagaact aaaaaatcta tctgtttctt ttcattctct gtatttttta   5700
tagtttctgt tgcatgggca taaagttgcc ttttaatca caattcagaa aatatcataa   5760
tatctcattt cactaaataa tagtgaacgg caggtatatg tgatgggtta aaaaggatcg   5820
gcggccgctc gatttaaatc tcgagaggcc tgacgtcggg                         5860
```

<210> SEQ ID NO 13
<211> LENGTH: 23
<212> TYPE: DNA
<213> ORGANISM: Corynebacterium glutamicum

```
<220> FEATURE:
<223> OTHER INFORMATION: SOD8

<400> SEQUENCE: 13
accctggcgg aaaccctgag tcg                                              23

<210> SEQ ID NO 14
<211> LENGTH: 65
<212> TYPE: DNA
<213> ORGANISM: Corynebacterium glutamicum
<220> FEATURE:
<223> OTHER INFORMATION: SOD1

<400> SEQUENCE: 14
tacgaccagg gccacgggta aaaaatcctt tcgtaggttt ccgcaccgag catatacatc      60
ttttg                                                                  65

<210> SEQ ID NO 15
<211> LENGTH: 40
<212> TYPE: DNA
<213> ORGANISM: Corynebacterium glutamicum
<220> FEATURE:
<223> OTHER INFORMATION: LYSC2

<400> SEQUENCE: 15
cctacgaaag gattttttac ccgtggccct ggtcgtacag                            40

<210> SEQ ID NO 16
<211> LENGTH: 21
<212> TYPE: DNA
<213> ORGANISM: Corynebacterium glutamicum
<220> FEATURE:
<223> OTHER INFORMATION: LYSC6

<400> SEQUENCE: 16
gattagtgga acctcgtcgt c                                                21

<210> SEQ ID NO 17
<211> LENGTH: 19
<212> TYPE: DNA
<213> ORGANISM: Corynebacterium glutamicum
<220> FEATURE:
<223> OTHER INFORMATION: SOD4

<400> SEQUENCE: 17
gcggcgcagg attttctaa                                                   19

<210> SEQ ID NO 18
<211> LENGTH: 22
<212> TYPE: DNA
<213> ORGANISM: Corynebacterium glutamicum
<220> FEATURE:
<223> OTHER INFORMATION: LYSC4

<400> SEQUENCE: 18
tcggttgcct gagtaatgtc tt                                               22

<210> SEQ ID NO 19
<211> LENGTH: 5720
<212> TYPE: DNA
<213> ORGANISM: Corynebacterium glutamicum
<220> FEATURE:
<223> OTHER INFORMATION: PK19
<220> FEATURE:
<221> NAME/KEY: misc_feature
<222> LOCATION: (2706)..(3968)
<223> OTHER INFORMATION: lysC complement
```

```
<220> FEATURE:
<221> NAME/KEY: misc_feature
<222> LOCATION: (3969)..(4166)
<223> OTHER INFORMATION: Psod complement
<220> FEATURE:
<221> NAME/KEY: misc_feature
<222> LOCATION: (4538)..(5236)
<223> OTHER INFORMATION: 5' lysC complement
<220> FEATURE:
<221> NAME/KEY: misc_feature
<222> LOCATION: (5626)..(6420)
<223> OTHER INFORMATION: KanR
<220> FEATURE:
<221> NAME/KEY: misc_feature
<222> LOCATION: (6449)..(6911)
<223> OTHER INFORMATION: PsacB
<220> FEATURE:
<221> NAME/KEY: misc_feature
<222> LOCATION: (6912)..(6)
<223> OTHER INFORMATION: sacB

<400> SEQUENCE: 19
```

| | | | | | |
|---|---|---|---|---|---|
| ggtcgactct | agaggatccc | cgggtaccga | gctcgaattc | actggccgtc | gttttacaac | 60 |
| gtcgtgactg | ggaaaaccct | ggcgttaccc | aacttaatcg | ccttgcagca | catccccctt | 120 |
| tcgccagctg | gcgtaatagc | gaagaggccc | gcaccgatcg | cccttcccaa | cagttgcgca | 180 |
| gcctgaatgg | cgaatggcga | taagctagct | tcacgctgcc | gcaagcactc | agggcgcaag | 240 |
| ggctgctaaa | ggaagcggaa | cacgtagaaa | gccagtccgc | agaaacggtg | ctgaccccgg | 300 |
| atgaatgtca | gctactgggc | tatctggaca | agggaaaacg | caagcgcaaa | gagaaagcag | 360 |
| gtagcttgca | gtgggcttac | atggcgatag | ctagactggg | cggttttatg | gacagcaagc | 420 |
| gaaccggaat | tgccagctgg | ggcgccctct | ggtaaggttg | ggaagccctg | caaagtaaac | 480 |
| tggatggctt | tcttgccgcc | aaggatctga | tggcgcaggg | gatcaagatc | tgatcaagag | 540 |
| acaggatgag | gatcgtttcg | catgattgaa | caagatggat | tgcacgcagg | ttctccggcc | 600 |
| gcttgggtgg | agaggctatt | cggctatgac | tgggcacaac | agacaatcgg | ctgctctgat | 660 |
| gccgccgtgt | tccggctgtc | agcgcagggg | cgcccggttc | ttttttgtcaa | gaccgacctg | 720 |
| tccggtgccc | tgaatgaact | ccaagacgag | gcagcgcggc | tatcgtggct | ggccacgacg | 780 |
| ggcgttcctt | gcgcagctgt | gctcgacgtt | gtcactgaag | cgggaaggga | ctggctgcta | 840 |
| ttgggcgaag | tgccggggca | ggatctcctg | tcatctcacc | ttgctcctgc | cgagaaagta | 900 |
| tccatcatgg | ctgatgcaat | gcggcggctg | catacgcttg | atccggctac | ctgcccattc | 960 |
| gaccaccaag | cgaaacatcg | catcgagcga | gcacgtactc | ggatggaagc | cggtcttgtc | 1020 |
| gatcaggatg | atctggacga | agagcatcag | gggctcgcgc | cagccgaact | gttcgccagg | 1080 |
| ctcaaggcgc | ggatgcccga | cggcgaggat | ctcgtcgtga | cccatggcga | tgcctgcttg | 1140 |
| ccgaatatca | tggtggaaaa | tggccgcttt | tctggattca | tcgactgtgg | ccggctgggt | 1200 |
| gtggcggacc | gctatcagga | catagcgttg | gctacccgtg | atattgctga | agagcttggc | 1260 |
| ggcgaatggg | ctgaccgctt | cctcgtgctt | tacggtatcg | ccgctcccga | ttcgcagcgc | 1320 |
| atcgccttct | atcgccttct | tgacgagttc | ttctgagcgg | gactctgggg | ttcgctagag | 1380 |
| gatcgatcct | ttttaaccca | tcacatatac | ctgccgttca | ctattattta | gtgaaatgag | 1440 |
| atattatgat | attttctgaa | ttgtgattaa | aaaggcaact | ttatgcccat | gcaacagaaa | 1500 |
| ctataaaaaa | tacagagaat | gaaaagaaac | agatagattt | tttagttctt | taggcccgta | 1560 |
| gtctgcaaat | ccttttatga | ttttctatca | aacaaaagag | gaaaatagac | cagttgcaat | 1620 |
| ccaaacgaga | gtctaataga | atgaggtcga | aagtaaatc | gcgcgggttt | gttactgata | 1680 |
| aagcaggcaa | gacctaaaat | gtgtaaaggg | caaagtgtat | actttggcgt | cacccccttac | 1740 |

```
atattttagg tcttttttta ttgtgcgtaa ctaacttgcc atcttcaaac aggagggctg    1800
gaagaagcag accgctaaca cagtacataa aaaaggagac atgaacgatg aacatcaaaa    1860
agtttgcaaa acaagcaaca gtattaacct ttactaccgc actgctggca ggaggcgcaa    1920
ctcaagcgtt tgcgaaagaa acgaaccaaa agccatataa ggaaacatac ggcatttccc    1980 atattcacg ccatgatatg ctgcaaatcc ctgaacagca aaaaaatgaa aaatatcaag     2040
tttctgaatt tgattcgtcc acaattaaaa atatctcttc tgcaaaaggc ctggacgttt    2100
gggacagctg gccattacaa aacgctgacg gcactgtcgc aaactatcac ggctaccaca    2160
tcgtctttgc attagccgga gatcctaaaa atgcggatga cacatcgatt tacatgttct    2220
atcaaaaagt cggcgaaact tctattgaca gctggaaaaa cgctggccgc gtctttaaag    2280
acagcgacaa attcgatgca aatgattcta tcctaaaaga ccaaacacaa gaatggtcag    2340
gttcagccac atttacatct gacggaaaaa tccgtttatt ctacactgat ttctccggta    2400
aacattacgg caaacaaaca ctgacaactg cacaagttaa cgtatcagca tcagacagct    2460
ctttgaacat caacggtgta gaggattata atcaatctt tgacggtgac ggaaaaacgt     2520
atcaaaatgt acagcagttc atcgatgaag gcaactacag ctcaggcgac aaccatacgc    2580
tgagagatcc tcactacgta gaagataaag gccacaaata cttagtattt gaagcaaaca    2640
ctggaactga agatggctac caaggcgaag aatctttatt taacaaagca tactatggca    2700
aaagcacatc attcttccgt caagaaagtc aaaaacttct gcaaagcgat aaaaaacgca    2760
cggctgagtt agcaaacggc gctctcggta tgattgagct aaacgatgat tacacactga    2820
aaaaagtgat gaaaccgctg attgcatcta acacagtaac agatgaaatt gaacgcgcga    2880
acgtctttaa aatgaacggc aaatggtacc tgttcactga ctcccgcgga tcaaaaatga    2940
cgattgacgg cattacgtct aacgatattt acatgcttgg ttatgtttct aattctttaa    3000
ctggcccata caagccgctg aacaaaactg gccttgtgtt aaaaatggat cttgatccta    3060
acgatgtaac ctttacttac tcacacttcg ctgtacctca agcgaaagga aacaatgtcg    3120
tgattacaag ctatatgaca aacagaggat tctacgcaga caaacaatca acgtttgcgc    3180
cgagcttcct gctgaacatc aaaggcaaga aaacatctgt tgtcaaagac agcatccttg    3240
aacaaggaca attaacagtt aacaaataaa acgcaaaag aaaatgccga tgggtaccga    3300
gcgaaatgac cgaccaagcg acgcccaacc tgccatcacg agatttcgat tccaccgccg    3360
ccttctatga aaggttgggc ttcggaatcg ttttccggga cgccctcgcg gacgtgctca    3420
tagtccacga cgcccgtgat tttgtagccc tggccgacgg ccagcaggta ggccgacagg    3480
ctcatgccgg ccgccgccgc ttttcctca atcgctcttc gttcgtctgg aaggcagtac    3540
accttgatag gtgggctgcc cttcctggtt ggcttggttt catcagccat ccgcttgccc    3600
tcatctgtta cgccggcggt agccggccag cctcgcagag caggattccc gttgagcacc    3660
gccaggtgcg aataagggac agtgaagaag gaacacccgc tcgcgggtgg gcctacttca    3720
cctatcctgc ccggctgacg ccgttggata caccaaggaa agtctacacg aaccctttgg    3780
caaaatcctg tatatcgtgc gaaaaaggat ggatataccg aaaaaatcgc tataatgacc    3840
ccgaagcagg gttatgcagc ggaaaagcgc tgcttccctg ctgttttgtg aatatctac     3900 cgactggaaa caggcaaatg caggaaatta ctgaactgag gggacaggcg agagacgatg    3960
ccaaagagct cctgaaaatc tcgataactc aaaaaatacg cccggtagtg atcttatttc    4020
attatgtgta aagttggaac ctcttacgtg ccgatcaacg tctcattttc gccaaaagtt    4080
ggcccagggc ttcccggtat caacagggac accaggattt atttattctg cgaagtgatc    4140
```

```
ttccgtcaca ggtatttatt cggcgcaaag tgcgtcgggt gatgctgcca acttactgat    4200
ttagtgtatg atggtgtttt tgaggtgctc cagtggcttc tgtttctatc agctcctgaa    4260
aatctcgata actcaaaaaa tacgcccggt agtgatctta tttcattatg gtgaaagttg    4320
gaacctctta cgtgccgatc aacgtctcat tttcgccaaa agttggccca gggcttcccg    4380
gtatcaacag ggacaccagg atttatttat tctgcgaagt gatcttccgt cacaggtatt    4440
tattcggcgc aaagtgcgtc gggtgatgct gccaacttac tgatttagtg tatgatggtg    4500
tttttgaggt gctccagtgg cttctgtttc tatcagggct ggatgatcct ccagcgcggg    4560
gatctcatgc tggagttctt cgcccacccc aaaaggatct aggtgaagat cctttttgat    4620
aatctcatga ccaaaatccc ttaacgtgag ttttcgttcc actgagcgtc agaccccgta    4680
gaaaagatca aggatcttc ttgagatcct ttttttctgc gcgtaatctg ctgcttgcaa    4740
acaaaaaaac caccgctacc agcggtggtt tgtttgccgg atcaagagct accaactctt    4800
tttccgaagg taactggctt cagcagagcg cagataccaa atactgttct tctagtgtag    4860
ccgtagttag gccaccactt caagaactct gtagcaccgc ctacatacct cgctctgcta    4920
atcctgttac cagtggctgc tgccagtggc gataagtcgt gtcttaccgg gttggactca    4980
agacgatagt taccggataa ggcgcagcgg tcgggctgaa cggggggttc gtgcacacag    5040
cccagcttgg agcgaacgac ctacaccgaa ctgagatacc tacagcgtga gctatgagaa    5100
agcgccacgc ttcccgaagg gagaaaggcg gacaggtatc cggtaagcgg cagggtcgga    5160
acaggagagc gcacgaggga gcttccaggg ggaaacgcct ggtatcttta tagtcctgtc    5220
gggtttcgcc acctctgact tgagcgtcga ttttgtgat gctcgtcagg ggggcggagc    5280
ctatggaaaa acgccagcaa cgcggccttt ttacggttcc tggccttttg ctggccttt    5340 gctcacatgt tctttcctgc gttatcccct gattctgtgg ataaccgtat taccgccttt    5400
gagtgagctg ataccgctcg ccgcagccga acgaccgagc gcagcgagtc agtgagcgag    5460
gaagcggaag agcgcccaat acgcaaaccg cctctccccg cgcgttggcc gattcattaa    5520
tgcagctggc acgacaggtt tcccgactgg aaagcgggca gtgagcgcaa cgcaattaat    5580
gtgagttagc tcactcatta ggaccccag gctttacact ttatgcttcc ggctcgtatg    5640
ttgtgtggaa ttgtgagcgg ataacaattt cacacaggaa acagctatga ccatgattac    5700
gccaagcttg catgcctgca                                                5720

<210> SEQ ID NO 20
<211> LENGTH: 27
<212> TYPE: DNA
<213> ORGANISM: Corynebacterium glutamicum
<220> FEATURE:
<223> OTHER INFORMATION: LYSC23

<400> SEQUENCE: 20
caccgcggct ttggacatca ctgctac                                           27

<210> SEQ ID NO 21
<211> LENGTH: 26
<212> TYPE: DNA
<213> ORGANISM: Corynebacterium glutamicum
<220> FEATURE:
<223> OTHER INFORMATION: LYSC24

<400> SEQUENCE: 21
cctggggctt tagcggatgc gtctca                                            26
```

<210> SEQ ID NO 22
<211> LENGTH: 8324
<212> TYPE: DNA
<213> ORGANISM: Corynebacterium glutamicum
<220> FEATURE:
<223> OTHER INFORMATION: PK19
<220> FEATURE:
<221> NAME/KEY: misc_feature
<222> LOCATION: (2706)..(3968)
<223> OTHER INFORMATION: lysC complement
<220> FEATURE:
<221> NAME/KEY: misc_feature
<222> LOCATION: (3969)..(4166)
<223> OTHER INFORMATION: Psod complement
<220> FEATURE:
<221> NAME/KEY: misc_feature
<222> LOCATION: (4538)..(5236)
<223> OTHER INFORMATION: 5' lysC complement
<220> FEATURE:
<221> NAME/KEY: misc_feature
<222> LOCATION: (5626)..(6420)
<223> OTHER INFORMATION: KanR
<220> FEATURE:
<221> NAME/KEY: misc_feature
<222> LOCATION: (6449)..(6911)
<223> OTHER INFORMATION: PsacB
<220> FEATURE:
<221> NAME/KEY: misc_feature
<222> LOCATION: (6912)..(6)
<223> OTHER INFORMATION: sacB

<400> SEQUENCE: 22

```
aaacgcaaaa gaaaatgccg atgggtaccg agcgaaatga ccgaccaagc gacgcccaac      60
ctgccatcac gagatttcga ttccaccgcc gccttctatg aaaggttggg cttcggaatc     120
gttttccggg acgccctcgc ggacgtgctc atagtccacg acgcccgtga ttttgtagcc     180
ctggccgacg gccagcaggt aggccgacag gctcatgccg gccgccgccg ccttttcctc     240
aatcgctctt cgttcgtctg gaaggcagta caccttgata ggtgggctgc ccttcctggt     300
tggcttggtt tcatcagcca tccgcttgcc ctcatctgtt acgccggcgg tagccggcca     360
gcctcgcaga gcaggattcc cgttgagcac cgccaggtgc gaataaggga cagtgaagaa     420
ggaacacccg ctcgcgggtg ggcctacttc acctatcctg cccggctgac gccgttggat     480
acaccaagga aagtctacac gaacccttttg gcaaaatcct gtatatcgtg cgaaaaagga    540
tggatatacc gaaaaaatcg ctataatgac cccgaagcag ggttatgcag cggaaaagcg     600
ctgcttccct gctgttttgt ggaatatcta ccgactggaa acaggcaaat gcaggaaatt     660
actgaactga ggggacaggc gagagacgat gccaagagc tcctgaaaat ctcgataact       720
caaaaatac gcccggtagt gatcttattt cattatggtg aaagttggaa cctcttacgt       780
gccgatcaac gtctcatttt cgccaaaagt tggcccaggg cttcccggta tcaacaggga    840
caccaggatt tatttattct gcgaagtgat cttccgtcac aggtatttat tcggcgcaaa     900
gtgcgtcggg tgatgctgcc aacttactga tttagtgtat gatggtgttt ttgaggtgct     960
ccagtggctt ctgtttctat cagctcctga aaatctcgat aactcaaaaa atacgcccgg    1020
tagtgatctt atttcattat ggtgaaagtt ggaacctctt acgtgccgat caacgtctca    1080
ttttcgccaa aagttggccc agggcttccc ggtatcaaca gggacaccag gatttattta    1140
ttctgcgaag tgatcttccg tcacaggtat ttattcggcg caaagtgcgt cgggtgatgc    1200
tgccaactta ctgatttagt gtatgatggt gttttgagg tgctccagtg gcttctgttt     1260
ctatcagggc tggatgatcc tccagcgcgg ggatctcatg ctggagttct tcgcccaccc    1320
caaaaggatc taggtgaaga tcctttttga taatctcatg accaaaatcc cttaacgtga    1380
gttttcgttc cactgagcgt cagaccccgt agaaaagatc aaaggatctt cttgagatcc    1440
```

```
ttttttctg cgcgtaatct gctgcttgca aacaaaaaaa ccaccgctac cagcggtggt   1500
ttgtttgccg gatcaagagc taccaactct ttttccgaag gtaactggct tcagcagagc   1560
gcagatacca aatactgttc ttctagtgta gccgtagtta ggccaccact tcaagaactc   1620
tgtagcaccg cctacatacc tcgctctgct aatcctgtta ccagtggctg ctgccagtgg   1680
cgataagtcg tgtcttaccg ggttggactc aagacgatag ttaccggata aggcgcagcg   1740
gtcgggctga acggggggtt cgtgcacaca gcccagcttg gagcgaacga cctacaccga   1800
actgagatac ctacagcgtg agctatgaga aagcgccacg cttcccgaag ggagaaaggc   1860
ggacaggtat ccggtaagcg gcagggtcgg aacaggagag cgcacgaggg agcttccagg   1920
gggaaacgcc tggtatcttt atagtcctgt cgggtttcgc cacctctgac ttgagcgtcg   1980
atttttgtga tgctcgtcag ggggcggag cctatggaaa aacgccagca acgcggcctt   2040
tttacggttc ctggccttt gctggccttt tgctcacatg ttctttcctg cgttatcccc   2100
tgattctgtg gataaccgta ttaccgcctt tgagtgagct gataccgctc gccgcagccg   2160
aacgaccgag cgcagcgagt cagtgagcga ggaagcggaa gagcgcccaa tacgcaaacc   2220
gcctctcccc gcgcgttggc cgattcatta atgcagctgg cacgacaggt ttcccgactg   2280
gaaagcgggc agtgagcgca acgcaattaa tgtgagttag ctcactcatt aggcacccca   2340
ggctttacac tttatgcttc cggctcgtat gttgtgtgga attgtgagcg gataacaatt   2400
tcacacagga aacagctatg accatgatta cgccaagctt gcatgcctgc aggtcgactc   2460
tagaggatcc ccgggtaccg agctcgaatt cgcccttcg gttgcctgag taatgtcttc   2520
tacctcgatt tccgtgccac ggaattcaat cttacggcct gcggaacgtg gggaagcaaa   2580
gaaacgaaca gtgtcagctg gaaattgcg ctcttccaaa agggtgcgca taacctggcc   2640
gacctggccg gttgcaccaa caactgcgat ggtggtcatt gtaaaactac tcctttaaaa   2700
ctttagcgtc cggtgcctgc ataaacgacg gcttcgtctt cgccgcccag ctggaactgc   2760
tcatgcaatg cacgtgcagc agcatccaga tcatcttcac ggatcagcac ggaaatacga   2820
atctcagagg tggaaatcaa ttcgatgttc acgttgacat cgcgcagagc ttccatgaac   2880
tctgcggtaa cacctgggtg agacttcatg ccagcaccca cgagggagac tttgccgacc   2940
tggtcgtcgt aaagcacatt ggtccagttg ccctgaacct gaagcttctt caagatctcc   3000
atcgcgcggc ggccgtcgga acgagggcag gtgaagatga tgtcggtggt gccgtcttct   3060
acagaagaga cgttctgcag aaccatgtca atgttgattt ctgcatcagc caacgcacgg   3120
aaaaccttcg cagcctcgcc tggcttatcg gaaatacgcca aacggttac tttggcttcg   3180 gacttgtcgg ttgcgacacc ggtaaggact gcttcttcca caggaatatc ctccatagag   3240
ccggcaatca aagtgccggg atcattacta taagacgagc gtacgcgaag tggcacattg   3300
aatgcacgag cgtattcaac actgcgcagc accaaaatct tggagccaac agcagcaagt   3360
tccagcattt cttcgaagct gagcttttcc agcttctgtg cattaggaac gatgcgcggg   3420
tcagcggtat acacaccgtc aacgtccgag taaatctcac acacatcagc gttcaaagca   3480
gctgccaacg caactgcagt ggtgtcagaa ccaccacgac ccaacgtggt gacatcgcgg   3540
gtttctttat aaacccctg gaaccagca acaatgcaga tcttgccctc atcgagtgct   3600
tcacgcacac gacctggagt gacatcaaca atgcgtgcgt ttccgtggcg ctcggtggtg   3660
agcacaccag cctgagagcc cgtgaaagat tgggcttctg cgccaaggga ctcaatagcc   3720
atggcgacga gagcgttaga aatacgctca ccagcagtca ggagcatatc catttcacga   3780
gctggcggaa cgggattcac tgccgctgca agttctagaa gttcatccgt ggtgtctccc   3840
```

```
attgcggagc agacaaccac gacatcattt ccagccttct tggtggcaac gatccgttca   3900
gcgacgtttc taatgcgttc cgcactctca agcgaggaac cgccatattt ctgtacgacc   3960
agggccacgg gtaaaaaatc ctttcgtagg tttccgcacc gagcatatac atcttttgaa   4020
aatccgtcag atggcgcttc gcaaaagtac ttggtgcgac acctcccaat gataggcctt   4080
tttgttgata ttgcaacgaa attttttcagc cgacctattt atcgggtagc gggtcacaag   4140
cccggaataa ttggcagcta agtagggttg aagggcataa ggcttcctca attttcgaaa   4200
ggaacattcc tgttatggca tggttttttcg cacccgaacc cgtgatggtt accgctgatg   4260
aggcgcttaa aggtggcagg catcctgttt tagaaaatcc tgcgccgcaa gggcgaattc   4320
actggccgtc gttttacaac gtcgtgactg ggaaaaccct ggcgttaccc aacttaatcg   4380
ccttgcagca catccccctt tcgccagctg gcgtaatagc gaagaggccc gcaccgatcg   4440
cccttcccaa cagttgcgca gcctgaatgg cgaatggcga taagctagat gcatgctcga   4500
gcggccgcca gtgtgatgga tatctgcaga attcgccctt ggggctttag cggatgcgtc   4560
tcagccactg ggacgcgttc caataaacag accatatatt gatattcgat ttaatatttg   4620
agacaaaagt gacaggtgct acttcgcgag caactctttta gtcaactacc ctgaatcaag   4680
tgcaaagcaa tctgctcgcc gtgcttttcg ccctagcatc ggcattaaca atcgcatggg   4740
gcaccgtggt cagacaccgg atcgcgctcc gcaccccaaa agatggctcc ctaaggagct   4800
cacctttact caatgctctg atgacaccga tgtggtgggc aggcatgagt accgcgatgc   4860
tggcatattt cttacaaaca gtagcacttg gtttcggcac cctcttggta gtgcaaccag   4920
tgcttgtcct gtcgctgatg ttcacgctgc cgctctcagc acgattcaat ggctaccgac   4980
tacgccgaac tgaaatcttc tgggctaccc tcctcaccgt agccgtgggc atcatgatcg   5040
ttttgggacg ccccccttccc ggaaaccccc accccactc gatcgatgga ttccagtact   5100
tttagtcggc gttgcagtaa tgggtggaat gtggctgctt gcggaatacg tattaaagaa   5160
ggacaaagcc ctcatccttg gtcttgtgac gggtgcattg tttggctacg tagcagtgat   5220
gtccaaagcc gcggtgaagg gcgaattcca gcacactggc ggccgttact agcttcacgc   5280
tgccgcaagc actcagggcg caagggctgc taaaggaagc ggaacacgta gaaagccagt   5340
ccgcagaaac ggtgctgacc ccggatgaat gtcagctact gggctatctg gacaagggaa   5400
aacgcaagcg caaagagaaa gcaggtagct tgcagtgggc ttacatggcg atagctagac   5460
tgggcggttt tatggacagc aagcgaaccg gaattgccag ctgggcgcc ctctggtaag   5520
gttgggaagc cctgcaaagt aaactggatg gctttcttgc cgccaaggat ctgatggcgc   5580
aggggatcaa gatctgatca agagacagga tgaggatcgt ttcgcatgat tgaacaagat   5640
ggattgcacg caggttctcc ggccgcttgg gtggagaggc tattcggcta tgactgggca   5700
caacagacaa tcggctgctc tgatgccgcc gtgttccggc tgtcagcgca ggggcgcccg   5760
gttcttttgg tcaagaccga cctgtccggt gccctgaatg aactccaaga cgaggcagcg   5820
cggctatcgt ggctggccac gacgggcgtt ccttgcgcag ctgtgctcga cgttgtcact   5880
gaagcgggaa gggactggct gctattgggc gaagtgccgg ggcaggatct cctgtcatct   5940
caccttgctc ctgccgagaa agtatccatc atggctgatg caatgcggcg gctgcatacg   6000
cttgatccgg ctacctgccc attcgaccac caagcgaaac atcgcatcga gcgagcacgt   6060
actcggatgg aagccggtct tgtcgatcag gatgatctgg acgaagagca tcaggggctc   6120
gcgccagccg aactgttcgc caggctcaag gcgcggatgc ccgacggcga ggatctcgtc   6180
gtgacccatg gcgatgcctg cttgccgaat atcatggtgg aaaatggccg cttttctgga   6240
```

```
ttcatcgact gtggccggct gggtgtggcg gaccgctatc aggacatagc gttggctacc      6300
cgtgatattg ctgaagagct tggcggcgaa tgggctgacc gcttcctcgt gctttacggt      6360
atcgccgctc ccgattcgca gcgcatcgcc ttctatcgcc ttcttgacga gttcttctga      6420
gcgggactct ggggttcgct agaggatcga tcctttttaa cccatcacat atacctgccg      6480
ttcactatta tttagtgaaa tgagatatta tgatattttc tgaattgtga ttaaaaaggc      6540
aactttatgc ccatgcaaca gaaactataa aaatacaga gaatgaaaag aaacagatag      6600
attttttagt tctttaggcc cgtagtctgc aaatcctttt atgattttct atcaaacaaa      6660
agaggaaaat agaccagttg caatccaaac gagagtctaa tagaatgagg tcgaaaagta      6720
aatcgcgcgg gtttgttact gataaagcag gcaagaccta aatgtgtaa agggcaaagt      6780 gtatactttg gcgtcacccc ttacatattt taggtctttt tttattgtgc gtaactaact      6840
tgccatcttc aaacaggagg gctggaagaa gcagaccgct aacacagtac ataaaaagg      6900 agacatgaac gatgaacatc aaaaagtttg caaaacaagc aacagtatta accttactg      6960 ccgcactgct ggcaggaggc gcaactcaag cgtttgcgaa agaaacgaac caaaagccat      7020
ataaggaaac atacggcatt tcccatatta cacgccatga tatgctgcaa atccctgaac      7080
agcaaaaaaa tgaaaatat caagttcctg aatttgattc gtccacaatt aaaaatatct      7140
cttctgcaaa aggcctggac gtttgggaca gctggccatt acaaaacgct gacggcactg      7200
tcgcaaacta tcacggctac cacatcgtct ttgcattagc cggagatcct aaaaatgcgg      7260
atgacacatc gatttacatg ttctatcaaa agtcggcga aacttctatt gacagctgga      7320
aaaacgctgg ccgcgtcttt aaagacagcg acaaattcga tgcaaatgat tctatcctaa      7380
aagaccaaac acaagaatgg tcaggttcag ccacatttac atctgacgga aaaatccgtt      7440
tattctacac tgatttctcc ggtaaacatt acggcaaaca aacactgaca actgcacaag      7500
ttaacgtatc agcatcagac agctctttga acatcaacgg tgtagaggat tataaatcaa      7560
tctttgacgg tgacggaaaa acgtatcaaa atgtacagca gttcatcgat gaaggcaact      7620
acagctcagg cgacaaccat acgctgagag atcctcacta cgtagaagat aaaggccaca      7680
aatacttagt atttgaagca aacactggaa ctgaagatgg ctaccaaggc gaagaatctt      7740
tatttaacaa agcatactat ggcaaaagca catcattctt ccgtcaagaa agtcaaaaac      7800
ttctgcaaag cgataaaaaa cgcacggctg agttagcaaa cggcgctctc ggtatgattg      7860
agctaaacga tgattacaca ctgaaaaaag tgatgaaacc gctgattgca tctaacacag      7920
taacagatga aattgaacgc gcgaacgtct ttaaaatgaa cggcaaatgg tacctgttca      7980
ctgactcccg cggatcaaaa atgacgattg acggcattac gtctaacgat atttacatgc      8040
ttggttatgt ttctaattct ttaactggcc catacaagcc gctgaacaaa actggccttg      8100
tgttaaaaat ggatcttgat cctaacgatg taacctttac ttactcacac ttcgctgtac      8160
ctcaagcgaa aggaaacaat gtcgtgatta caagctatat gacaaacaga ggattctacg      8220
cagacaaaca atcaacgttt gcgccgagct tcctgctgaa catcaaggc aagaaaacat      8280 ctgttgtcaa agacagcatc cttgaacaag gacaattaac agtt                      8324
```

<210> SEQ ID NO 23
<211> LENGTH: 52
<212> TYPE: DNA
<213> ORGANISM: Corynebacterium glutamicum
<220> FEATURE:
<223> OTHER INFORMATION: SEQ_ID_23

<400> SEQUENCE: 23

```
cccgggatcc gctagcggcg cgccggccgg cccggtgtga ataccgcac ag            52
```

<210> SEQ ID NO 24
<211> LENGTH: 53
<212> TYPE: DNA
<213> ORGANISM: Corynebacterium glutamicum
<220> FEATURE:
<223> OTHER INFORMATION: SEQ_ID_24

<400> SEQUENCE: 24

```
tctagactcg agcggccgcg gccggccttt aaattgaaga cgaaagggcc tcg          53
```

<210> SEQ ID NO 25
<211> LENGTH: 47
<212> TYPE: DNA
<213> ORGANISM: Corynebacterium glutamicum
<220> FEATURE:
<223> OTHER INFORMATION: SEQ_ID_25

<400> SEQUENCE: 25

```
gagatctaga cccggggatc cgctagcggg ctgctaaagg aagcgga                 47
```

<210> SEQ ID NO 26
<211> LENGTH: 38
<212> TYPE: DNA
<213> ORGANISM: Corynebacterium glutamicum
<220> FEATURE:
<223> OTHER INFORMATION: SEQ_ID_26

<400> SEQUENCE: 26

```
gagaggcgcg ccgctagcgt gggcgaagaa ctccagca                           38
```

<210> SEQ ID NO 27
<211> LENGTH: 34
<212> TYPE: DNA
<213> ORGANISM: Corynebacterium glutamicum
<220> FEATURE:
<223> OTHER INFORMATION: SEQ_ID_27

<400> SEQUENCE: 27

```
gagagggcgg ccgcgcaaag tcccgcttcg tgaa                               34
```

<210> SEQ ID NO 28
<211> LENGTH: 34
<212> TYPE: DNA
<213> ORGANISM: Corynebacterium glutamicum
<220> FEATURE:
<223> OTHER INFORMATION: SEQ_ID_28

<400> SEQUENCE: 28

```
gagagggcgg ccgctcaagt cggtcaagcc acgc                               34
```

<210> SEQ ID NO 29
<211> LENGTH: 140
<212> TYPE: DNA
<213> ORGANISM: Corynebacterium glutamicum
<220> FEATURE:
<223> OTHER INFORMATION: SEQ_ID_29

<400> SEQUENCE: 29

```
tcgaatttaa atctcgagag gcctgacgtc gggcccggta ccacgcgtca tatgactagt   60
tcggacctag ggatatcgtc gacatcgatg ctcttctgcg ttaattaaca attgggatcc  120
tctagacccg ggatttaaat                                              140
```

```
<210> SEQ ID NO 30
<211> LENGTH: 140
<212> TYPE: DNA
<213> ORGANISM: Corynebacterium glutamicum
<220> FEATURE:
<223> OTHER INFORMATION: SEQ_ID_30

<400> SEQUENCE: 30
gatcatttaa atcccgggtc tagaggatcc caattgttaa ttaacgcaga agagcatcga    60
tgtcgacgat atccctaggt ccgaactagt catatgacgc gtggtaccgg gcccgacgtc   120
aggcctctcg agatttaaat                                               140

<210> SEQ ID NO 31
<211> LENGTH: 5091
<212> TYPE: DNA
<213> ORGANISM: Corynebacterium glutamicum
<220> FEATURE:
<223> OTHER INFORMATION: PCLIK5MCS
<220> FEATURE:
<221> NAME/KEY: misc_feature
<222> LOCATION: (469)..(1260)
<223> OTHER INFORMATION: KanR
<220> FEATURE:
<221> NAME/KEY: misc_feature
<222> LOCATION: (1527)..(2387)
<223> OTHER INFORMATION: Ori EC  pMB    (complement)
<220> FEATURE:
<221> NAME/KEY: misc_feature
<222> LOCATION: (2533)..(3207)
<223> OTHER INFORMATION: Orf1
<220> FEATURE:
<221> NAME/KEY: misc_feature
<222> LOCATION: (3541)..(4662)
<223> OTHER INFORMATION: Rep Protein

<400> SEQUENCE: 31
tcgatttaaa tctcgagagg cctgacgtcg ggcccggtac cacgcgtcat atgactagtt    60
cggacctagg gatatcgtcg acatcgatgc tcttctgcgt taattaacaa ttgggatcct   120
ctagacccgg gatttaaatc gctagcgggc tgctaaagga agcggaacac gtagaaagcc   180
agtccgcaga aacggtgctg accccggatg aatgtcagct actgggctat ctggacaagg   240
gaaaacgcaa gcgcaaagag aaagcaggta gcttgcagtg ggcttacatg gcgatagcta   300
gactgggcgg ttttatggac agcaagcgaa ccggaattgc cagctggggc gccctctggt   360
aaggttggga agccctgcaa agtaaactgg atggctttct tgccgccaag gatctgatgg   420
cgcaggggat caagatctga tcaagagaca ggatgaggat cgtttcgcat gattgaacaa   480
gatggattgc acgcaggttc tccggccgct tgggtggaga ggctattcgg ctatgactgg   540
gcacaacaga caatcggctg ctctgatgcc gccgtgttcc ggctgtcagc gcaggggcgc   600
ccggttcttt ttgtcaagac cgacctgtcc ggtgccctga atgaactgca ggacgaggca   660
gcgcggctat cgtggctggc cacgacgggc gttccttgcg cagctgtgct cgacgttgtc   720
actgaagcgg gaagggactg gctgctattg ggcgaagtgc cggggcagga tctcctgtca   780
tctcaccttg ctcctgccga gaaagtatcc atcatggctg atgcaatgcg gcggctgcat   840
acgcttgatc cggctacctg cccattcgac caccaagcga acatcgcat  cgagcgagca   900 cgtactcgga tggaagccgg tcttgtcgat caggatgatc tggacgaaga gcatcagggg   960
ctcgcgccag ccgaactgtt cgccaggctc aaggcgcgca tgcccgacgg cgaggatctc  1020
gtcgtgaccc atggcgatgc ctgcttgccg aatatcatgg tggaaaatgg ccgcttttct  1080
ggattcatcg actgtggccg gctgggtgtg gcggaccgct atcaggacat agcgttggct  1140
acccgtgata ttgctgaaga gcttggcggc gaatgggctg accgcttcct cgtgctttac  1200
```

```
ggtatcgccg ctcccgattc gcagcgcatc gccttctatc gccttcttga cgagttcttc    1260
tgagcgggac tctggggttc gaaatgaccg accaagcgac gcccaacctg ccatcacgag    1320
atttcgattc caccgccgcc ttctatgaaa ggttgggctt cggaatcgtt ttccgggacg    1380
ccggctggat gatcctccag cgcggggatc tcatgctgga gttcttcgcc cacgctagcg    1440
gcgcgccggc cggccggtg tgaaataccg cacagatgcg taaggagaaa ataccgcatc     1500
aggcgctctt ccgcttcctc gctcactgac tcgctgcgct cggtcgttcg gctgcggcga    1560
gcggtatcag ctcactcaaa ggcggtaata cggttatcca cagaatcagg gataacgca     1620 ggaaagaaca tgtgagcaaa aggccagcaa aaggccagga accgtaaaaa ggccgcgttg    1680
ctggcgtttt tccataggct ccgcccccct gacgagcatc acaaaaatcg acgctcaagt    1740
cagaggtggc gaaacccgac aggactataa agataccagg cgtttccccc tggaagctcc    1800
ctcgtgcgct ctcctgttcc gaccctgccg cttaccggat acctgtccgc ctttctccct    1860
tcgggaagcg tggcgctttc tcatagctca cgctgtaggt atctcagttc ggtgtaggtc    1920
gttcgctcca agctgggctg tgtgcacgaa ccccccgttc agcccgaccg ctgcgcctta    1980
tccggtaact atcgtcttga gtccaacccg gtaagcacg acttatcgcc actggcagca     2040
gccactggta acaggattag cagagcgagg tatgtaggcg gtgctacaga gttcttgaag    2100
tggtggccta actacggcta cactagaagg acagtatttg gtatctgcgc tctgctgaag    2160
ccagttacct tcggaaaaag agttggtagc tcttgatccg gcaaacaaac caccgctggt    2220
agcggtggtt tttttgtttg caagcagcag attacgcgca gaaaaaaagg atctcaagaa    2280
gatcctttga tcttttctac ggggtctgac gctcagtgga acgaaaactc acgttaaggg    2340
attttggtca tgagattatc aaaaaggatc ttcacctaga tccttttaaa ggccggccgc    2400
ggccgcgcaa agtcccgctt cgtgaaaatt ttcgtgccgc gtgattttcc gccaaaaact    2460
ttaacgaacg ttcgttataa tggtgtcatg accttcacga cgaagtacta aaattggccc    2520
gaatcatcag ctatggatct ctctgatgtc gcgctggagt ccgacgcgct cgatgctgcc    2580
gtcgatttaa aaacggtgat cggatttttc cgagctctcg atacgacgga cgcgccagca    2640
tcacgagact gggccagtgc cgcgagcgac ctagaaactc tcgtggcgga tcttgaggag    2700
ctggctgacg agctgcgtgc tcggccagcg ccaggaggac gcacagtagt ggaggatgca    2760
atcagttgcg cctactgcgg tggcctgatt cctccccggc ctgacccgcg aggacggcgc    2820
gcaaaatatt gctcagatgc gtgtcgtgcc gcagccagcc gcgagcgcgc aacaaacgc     2880 cacgccgagg agctggaggc ggctaggtcg caaatggcgc tggaagtgcg tcccccgagc    2940
gaaattttgg ccatggtcgt cacagagctg gaagcggcag cgagaattat cgcgatcgtg    3000
gcggtgcccg caggcatgac aaacatcgta atgccgcgt ttcgtgtgcc gtggccgccc     3060
aggacgtgtc agcgccgcca ccacctgcac cgaatcggca gcagcgtcgc gcgtcgaaaa    3120
agcgcacagg cggcaagaag cgataagctg cacgaatacc tgaaaaatgt tgaacgcccc    3180
gtgagcggta actcacaggg cgtcggctaa cccccagtcc aaacctggga gaaagcgctc    3240
aaaaatgact ctagcggatt cacgagacat tgacacaccg gcctgaaat tttccgctga    3300 tctgttcgac acccatcccg agctcgcgct gcgatcacgt ggctggacga gcgaagaccg    3360
ccgcgaattc ctcgctcacc tgggcagaga aaatttccag ggcagcaaga cccgcgactt    3420
cgccagcgct tggatcaaag acccggacac ggagaaacac agccgaagtt ataccgagtt    3480
ggttcaaaat cgcttgcccg gtgccagtat gttgctctga cgcacgcgca gcacgcagcc    3540
gtgcttgtcc tggacattga tgtgccgagc caccaggccg gcgggaaaat cgagcacgta    3600
```

```
aaccccgagg tctacgcgat tttggagcgc tgggcacgcc tggaaaaagc gccagcttgg    3660
atcggcgtga atccactgag cgggaaatgc cagctcatct ggctcattga tccggtgtat    3720
gccgcagcag gcatgagcag cccgaatatg cgcctgctgg ctgcaacgac cgaggaaatg    3780
acccgcgttt tcggcgctga ccaggctttt tcacataggc tgagccgtgg ccactgcact    3840
ctccgacgat cccagccgta ccgctggcat gcccagcaca atcgcgtgga tcgcctagct    3900
gatcttatgg aggttgctcg catgatctca ggcacagaaa aacctaaaaa acgctatgag    3960
caggagtttt ctagcggacg ggcacgtatc gaagcggcaa gaaaagccac tgcggaagca    4020
aaagcacttg ccacgcttga agcaagcctg ccgagcgccg ctgaagcgtc tggagagctg    4080
atcgacggcg tccgtgtcct ctggactgct ccagggcgtg ccgcccgtga tgagacggct    4140
tttcgccacg ctttgactgt gggataccag ttaaaagcgg ctggtgagcg cctaaaagac    4200
accaagggtc atcgagccta cgagcgtgcc tacaccgtcg ctcaggcggt cggaggaggc    4260
cgtgagcctg atctgccgcc ggactgtgac cgccagacgg attggccgcg acgtgtgcgc    4320
ggctacgtcg ctaaaggcca gccagtcgtc cctgctcgtc agacagagac gcagagccag    4380
ccgaggcgaa aagctctggc cactatggga agacgtggcg gtaaaaggc cgcagaacgc    4440 tggaaagacc caaacagtga gtacgcccga gcacagcgag aaaaactagc taagtccagt    4500
caacgacaag ctaggaaagc taaggaaat cgcttgacca ttgcaggttg gtttatgact    4560
gttgagggag agactggctc gtggccgaca atcaatgaag ctatgtctga atttagcgtg    4620
tcacgtcaga ccgtgaatag agcacttaag gtctgcgggc attgaacttc cacgaggacg    4680
ccgaaagctt cccagtaaat gtgccatctc gtaggcagaa aacggttccc ccgtagggtc    4740
tctctcttgg cctcctttct aggtcgggct gattgctctt gaagctctct aggggggctc    4800
acaccatagg cagataacgt tccccaccgg ctcgcctcgt aagcgcacaa ggactgctcc    4860
caaagatctt caaagccact gccgcgactg ccttcgcgaa gccttgcccc gcggaaattt    4920
cctccaccga gttcgtgcac acccctatgc caagcttctt tcaccctaaa ttcgagagat    4980
tggattctta ccgtggaaat tcttcgcaaa aatcgtcccc tgatcgccct tgcgacgttg    5040
gcgtcggtgc cgctggttgc gcttggcttg accgacttga tcagcggccg c             5091
```

<210> SEQ ID NO 32
<211> LENGTH: 28
<212> TYPE: DNA
<213> ORGANISM: Corynebacterium glutamicum
<220> FEATURE:
<223> OTHER INFORMATION: SEQ_ID_32

<400> SEQUENCE: 32
gcgcggtacc tagactcacc ccagtgct                                        28

<210> SEQ ID NO 33
<211> LENGTH: 30
<212> TYPE: DNA
<213> ORGANISM: Corynebacterium glutamicum
<220> FEATURE:
<223> OTHER INFORMATION: SEQ_ID_33

<400> SEQUENCE: 33
ctctactagt ttagatgtag aactcgatgt                                      30

<210> SEQ ID NO 34
<211> LENGTH: 6349
<212> TYPE: DNA
<213> ORGANISM: Corynebacterium glutamicum

```
<220> FEATURE:
<223> OTHER INFORMATION: PCLIK5MCS
<220> FEATURE:
<221> NAME/KEY: misc_feature
<222> LOCATION: (42)..(177)
<223> OTHER INFORMATION: PmetA
<220> FEATURE:
<221> NAME/KEY: misc_feature
<222> LOCATION: (178)..(1311)
<223> OTHER INFORMATION: metA
<220> FEATURE:
<221> NAME/KEY: misc_feature
<222> LOCATION: (1727)..(2518)
<223> OTHER INFORMATION: KanR
<220> FEATURE:
<221> NAME/KEY: misc_feature
<222> LOCATION: (2785)..(3645)
<223> OTHER INFORMATION: Orf1
<220> FEATURE:
<221> NAME/KEY: misc_feature
<222> LOCATION: (3791)..(4465)
<223> OTHER INFORMATION: Ori-EC    complement
<220> FEATURE:
<221> NAME/KEY: misc_feature
<222> LOCATION: (4799)..(5920)
<223> OTHER INFORMATION: Rep Protein

<400> SEQUENCE: 34
tcgatttaaa tctcgagagg cctgacgtcg ggcccggtac ctagactcac cccagtgctt      60
aaagcgctgg gtttttcttt ttcagactcg tgagaatgca aactagacta gacagagctg     120
tccatataca ctggacgaag ttttagtctt gtccacccag aacaggcggt tattttcatg     180 cccacccctcg cgccttcagg tcaacttgaa atccaagcga tcggtgatgt ctccaccgaa     240
gccggagcaa tcattacaaa cgctgaaatc gcctatcacc gctggggtga ataccgcgta     300
gataaagaag gacgcagcaa tgtcgttctc atcgaacacg ccctcactgg agattccaac     360
gcagccgatt ggtgggctga cttgctcggt cccggcaaag ccatcaacac tgatatttac     420
tgcgtgatct gtaccaacgt catcggtggt tgcaacggtt ccaccggacc tggctccatg     480
catccagatg gaaatttctg gggtaatcgc ttccccgcca cgtccattcg tgatcaggta     540
aacgccgaaa acaattcct cgacgcactc ggcatcacca cggtcgccgc agtacttggt     600
ggttccatgg gtggtgcccg cacctagag tgggccgcaa tgtacccaga aactgttggc     660
gcagctgctg ttcttgcagt ttctgcacgc gccagcgcct ggcaaatcgg cattcaatcc     720
gcccaaatta aggcgattga aaacgaccac cactggcacg aaggcaacta ctacgaatcc     780
ggctgcaacc cagccaccgg actcggcgcc gcccgacgca tcgcccacct cacctaccgt     840
ggcgaactag aaatcgacga acgcttcggc accaaagccc aaaagaacga aacccactc     900 ggtccctacc gcaagcccga ccagcgcttc gccgtggaat cctacttgga ctaccaagca     960
gacaagctag tacagcgttt cgacgccggc tcctacgtct tgctcaccga cgccctcaac    1020
cgccacgaca ttggtcgcga ccgcggaggc ctcaacaagg cactcgaatc catcaaagtt    1080
ccagtccttg tcgcaggcgt agataccgat attttgtacc cctaccacca gcaagaacac    1140
ctctccagaa acctgggaaa tctactggca atggcaaaaa tcgtatcccc tgtcggccac    1200
gatgctttcc tcaccgaaag ccgccaaatg gatcgcatcg tgaggaactt cttcagcctc    1260
atctccccag acgaagacaa cccttcgacc tacatcgagt tctacatcta aactagttcg    1320
gacctaggga tatcgtcgac atcgatgctc ttctgcgtta attaacaatt gggatcctct    1380
agacccggga tttaaatcgc tagcgggctg ctaaaggaag cggaacacgt agaaagccag    1440
tccgcagaaa cggtgctgac cccggatgaa tgtcagctac tgggctatct ggacaaggga    1500
aaacgcaagc gcaaagagaa agcaggtagc ttgcagtggg cttacatggc gatagctaga    1560
```

```
ctgggcggtt ttatggacag caagcgaacc ggaattgcca gctggggcgc cctctggtaa    1620
ggttgggaag ccctgcaaag taaactggat ggctttcttg ccgccaagga tctgatggcg    1680 cagggatca agatctgatc aagagacagg atgaggatcg tttcgcatga ttgaacaaga     1740
tggattgcac gcaggttctc cggccgcttg ggtggagagg ctattcggct atgactgggc    1800
acaacagaca atcggctgct ctgatgccgc cgtgttccgg ctgtcagcgc agggggcgccc   1860 ggttcttttt gtcaagaccg acctgtccgg tgccctgaat gaactgcagg acgaggcagc    1920
gcggctatcg tggctggcca cgacgggcgt tccttgcgca gctgtgctcg acgttgtcac    1980
tgaagcggga agggactggc tgctattggg cgaagtgccg gggcaggatc tcctgtcatc    2040
tcaccttgct cctgccgaga aagtatccat catggctgat gcaatgcggc ggctgcatac    2100
gcttgatccg gctacctgcc cattcgacca ccaagcgaaa catcgcatcg agcgagcacg    2160
tactcggatg gaagccggtc ttgtcgatca ggatgatctg gacgaagagc atcaggggct    2220
cgcgccagcc gaactgttcg ccaggctcaa ggcgcgcatg cccgacggcg aggatctcgt    2280
cgtgacccat ggcgatgcct gcttgccgaa tatcatggtg gaaaatggcc gcttttctgg    2340
attcatcgac tgtggccggc tgggtgtggc ggaccgctat caggacatag cgttggctac    2400
ccgtgatatt gctgaagagc ttggcggcga atgggctgac cgcttcctcg tgctttacgg    2460
tatcgccgct cccgattcgc agcgcatcgc cttctatcgc cttcttgacg agttcttctg    2520
agcgggactc tggggttcga aatgaccgac caagcgacgc ccaacctgcc atcacgagat    2580
ttcgattcca ccgccgcctt ctatgaaagg ttgggcttcg gaatcgtttt ccggacgcc     2640 ggctggatga tcctccagcg cggggatctc atgctggagt tcttcgccca cgctagcggc    2700
gcgccggccg gccggtgtg aaataccgca cagatgcgta aggagaaaat accgcatcag    2760
gcgctcttcc gcttcctcgc tcactgactc gctgcgctcg gtcgttcggc tgcggcgagc    2820
ggtatcagct cactcaaagg cggtaatacg gttatccaca gaatcagggg ataacgcagg    2880
aaagaacatg tgagcaaaag gccagcaaaa ggccaggaac cgtaaaaagg ccgcgttgct    2940
ggcgtttttc cataggctcc gcccccctga cgagcatcac aaaaatcgac gctcaagtca    3000
gaggtggcga aacccgacag gactataaag ataccaggcg tttccccctg gaagctccct    3060
cgtgcgctct cctgttccga ccctgccgct taccggatac ctgtccgcct ttctcccttc    3120
gggaagcgtg gcgctttctc atagctcacg ctgtaggtat ctcagttcgg tgtaggtcgt    3180
tcgctccaag ctgggctgtg tgcacgaacc ccccgttcag cccgaccgct gcgccttatc    3240
cggtaactat cgtcttgagt ccaacccggt aagacacgac ttatcgccac tggcagcagc    3300
cactggtaac aggattagca gagcgaggta tgtaggcggt gctacagagt tcttgaagtg    3360
gtggcctaac tacggctaca ctagaaggac agtatttggt atctgcgctc tgctgaagcc    3420
agttaccttc ggaaaaagag ttggtagctc ttgatccggc aaacaaacca ccgctggtag    3480
cggtggtttt tttgtttgca agcagcagat tacgcgcaga aaaaaaggat ctcaagaaga    3540
tcctttgatc ttttctacgg ggtctgacgc tcagtggaac gaaaactcac gttaagggat    3600
tttggtcatg agattatcaa aaaggatctt cacctagatc cttttaaagg ccggccgcgg    3660
ccgcgcaaag tccgcttcg tgaaaatttt cgtgccgcgt gattttccgc caaaaacttt    3720
aacgaacgtt cgttataatg gtgtcatgac cttcacgacg aagtactaaa attggcccga    3780
atcatcagct atggatctct ctgatgtcgc gctggagtcc gacgcgctcg atgctgccgt    3840
cgatttaaaa acggtgatcg gattttccg agctctcgat acgacggacg cgccagcatc    3900
acgagactgg gccagtgccg cgagcgacct agaaactctc gtggcggatc ttgaggagct    3960
```

```
ggctgacgag ctgcgtgctc ggccagcgcc aggaggacgc acagtagtgg aggatgcaat    4020
cagttgcgcc tactgcggtg gcctgattcc tccccggcct gacccgcgag gacggcgcgc    4080
aaaatattgc tcagatgcgt gtcgtgccgc agccagccgc gagcgcgcca acaaacgcca    4140
cgccgaggag ctggaggcgg ctaggtcgca aatggcgctg gaagtgcgtc ccccgagcga    4200
aattttggcc atggtcgtca cagagctgga agcggcagcg agaattatcg cgatcgtggc    4260
ggtgcccgca ggcatgacaa acatcgtaaa tgccgcgttt cgtgtgccgt ggccgcccag    4320
gacgtgtcag cgccgccacc acctgcaccg aatcggcagc agcgtcgcgc gtcgaaaaag    4380
cgcacaggcg gcaagaagcg ataagctgca cgaatacctg aaaaatgttg aacgcccgt    4440 gagcggtaac tcacagggcg tcggctaacc cccagtccaa acctgggaga aagcgctcaa    4500
aaatgactct agcggattca cgagacattg acacaccggc ctggaaattt tccgctgatc    4560
tgttcgacac ccatcccgag ctcgcgctgc gatcacgtgg ctggacgagc aagaccgcc    4620 gcgaattcct cgctcacctg ggcagagaaa atttccaggg cagcaagacc cgcgacttcg    4680
ccagcgcttg gatcaaagac ccggacacgg agaaacacag ccgaagttat accgagttgg    4740
ttcaaaatcg cttgcccggt gccagtatgt tgctctgacg cacgcgcagc acgcagccgt    4800
gcttgtcctg gacattgatg tgccgagcca ccaggccggc gggaaaatcg agcacgtaaa    4860
ccccgaggtc tacgcgattt tggagcgctg ggcacgcctg gaaaaagcgc cagcttggat    4920
cggcgtgaat ccactgagcg ggaaatgcca gctcatctgg ctcattgatc cggtgtatgc    4980 cgcagcagge atgagcagcc cgaatatgcg cctgctggct gcaacgaccg aggaaatgac    5040
ccgcgttttc ggcgctgacc aggcttttc acataggctg agccgtggcc actgcactct    5100
ccgacgatcc cagccgtacc gctggcatgc ccagcacaat cgcgtggatc gcctagctga    5160
tcttatggag gttgctcgca tgatctcagg cacagaaaaa cctaaaaaac gctatgagca    5220
ggagttttct agcggacggg cacgtatcga agcggcaaga aaagccactg cggaagcaaa    5280
agcacttgcc acgcttgaag caagcctgcc gagcgccgct gaagcgtctg gagagctgat    5340
cgacggcgtc cgtgtcctct ggactgctcc agggcgtgcc gcccgtgatg agacggcttt    5400
tcgccacgct ttgactgtgg gataccagtt aaaagcggct ggtgagcgcc taaaagacac    5460
caagggtcat cgagcctacg agcgtgccta caccgtcgct caggcggtcg gaggaggccg    5520
tgagcctgat ctgccgccgg actgtgaccg ccagacggat tggccgcgac gtgtgcgcgg    5580
ctacgtcgct aaaggccagc cagtcgtccc tgctcgtcag acagacgcg agagccagcc    5640 gaggcgaaaa gctctggcca ctatgggaag acgtggcggt aaaaaggccg cagaacgctg    5700
gaaagaccca acagtgagt acgcccgagc acagcgagaa aaactagcta agtccagtca    5760
acgacaagct aggaaagcta aggaaatcg cttgaccatt gcaggttggt ttatgactgt    5820
tgagggagag actggctcgt ggccgacaat caatgaagct atgtctgaat ttagcgtgtc    5880
acgtcagacc gtgaatagag cacttaaggt ctgcgggcat tgaacttcca cgaggacgcc    5940
gaaagcttcc cagtaaatgt gccatctcgt aggcagaaaa cggttccccc gtagggtctc    6000
tctcttggcc tcctttctag gtcgggctga ttgctcttga agctctctag gggggctcac    6060
accataggca gataacgttc cccaccggct cgcctcgtaa gcgcacaagg actgctccca    6120
aagatcttca aagccactgc cgcgactgcc ttcgcgaagc cttgccccgc ggaaatttcc    6180
tccaccgagt tcgtgcacac ccctatgcca agcttctttc accctaaatt cgagagattg    6240
gattcttacc gtgaaattc ttcgcaaaaa tcgtcccctg atcgcccttg cgacgttggc    6300
gtcggtgccg ctggttgcgc ttggcttgac cgacttgatc agcggccgc                6349
```

-continued

<210> SEQ ID NO 35
<211> LENGTH: 29
<212> TYPE: DNA
<213> ORGANISM: Corynebacterium glutamicum
<220> FEATURE:
<223> OTHER INFORMATION: SEQ_ID_35

<400> SEQUENCE: 35
gagactcgag agctgccaat tattccggg                                         29

<210> SEQ ID NO 36
<211> LENGTH: 41
<212> TYPE: DNA
<213> ORGANISM: Corynebacterium glutamicum
<220> FEATURE:
<223> OTHER INFORMATION: SEQ_ID_36

<400> SEQUENCE: 36
cctgaaggcg cgagggtggg catgggtaaa aatcctttc g                            41

<210> SEQ ID NO 37
<211> LENGTH: 19
<212> TYPE: DNA
<213> ORGANISM: Corynebacterium glutamicum
<220> FEATURE:
<223> OTHER INFORMATION: SEQ_ID_37

<400> SEQUENCE: 37
cccaccctcg cgccttcag                                                    19

<210> SEQ ID NO 38
<211> LENGTH: 18
<212> TYPE: DNA
<213> ORGANISM: Corynebacterium glutamicum
<220> FEATURE:
<223> OTHER INFORMATION: SEQ_ID_38

<400> SEQUENCE: 38
ctgggtacat tgcggccc                                                     18

<210> SEQ ID NO 39
<211> LENGTH: 6386
<212> TYPE: DNA
<213> ORGANISM: Corynebacterium glutamicum
<220> FEATURE:
<223> OTHER INFORMATION: PCLIK5MCS
<220> FEATURE:
<221> NAME/KEY: misc_feature
<222> LOCATION: (6 )..(196 )
<223> OTHER INFORMATION: Psod
<220> FEATURE:
<221> NAME/KEY: misc_feature
<222> LOCATION: (197 )..(1330 )
<223> OTHER INFORMATION: metA
<220> FEATURE:
<221> NAME/KEY: misc_feature
<222> LOCATION: (1752 )..(2543 )
<223> OTHER INFORMATION: KanR
<220> FEATURE:
<221> NAME/KEY: misc_feature
<222> LOCATION: (2810 )..(3670 )
<223> OTHER INFORMATION: Ori-Ec (pMB) complement
<220> FEATURE:
<221> NAME/KEY: misc_feature
<222> LOCATION: (3816 )..(4490 )
<223> OTHER INFORMATION: Orf1
<220> FEATURE:
<221> NAME/KEY: misc_feature
<222> LOCATION: (4824 )..(5945 )
<223> OTHER INFORMATION: Rep Protein

<400> SEQUENCE: 39

```
tcgagagctg ccaattattc cgggcttgtg acccgctacc cgataaatag gtcggctgaa      60
aaatttcgtt gcaatatcaa caaaaaggcc tatcattggg aggtgtcgca ccaagtactt     120
ttgcgaagcg ccatctgacg gattttcaaa agatgtatat gctcggtgcg gaaacctacg     180
aaaggatttt ttacccatgc ccaccctcgc gccttcaggt caacttgaaa tccaagcgat     240
cggtgatgtc tccaccgaag ccggagcaat cattacaaac gctgaaatcg cctatcaccg     300
ctggggtgaa taccgcgtag ataaagaagg acgcagcaat gtcgttctca tcgaacacgc     360
cctcactgga gattccaacg cagccgattg gtgggctgac ttgctcggtc ccggcaaagc     420
catcaacact gatatttact gcgtgatctg taccaacgtc atcggtggtt gcaacggttc     480
caccggacct ggctccatgc atccagatgg aaatttctgg ggtaatcgct tccccgccac     540
gtccattcgt gatcaggtaa acgccgaaaa acaattcctc gacgcactcg gcatcaccac     600
ggtcgccgca gtacttggtg gttccatggg tggtgcccgc accctagagt gggccgcaat     660
gtacccagaa actgttggcg cagctgctgt tcttgcagtt tctgcacgcg ccagcgcctg     720
gcaaatcggc attcaatccg cccaaattaa ggcgattgaa aacgaccacc actggcacga     780
aggcaactac tacgaatccg gctgcaaccc agccaccgga ctcggcgccg cccgacgcat     840
cgcccacctc acctaccgtg gcgaactaga aatcgacgaa cgcttcggca ccaaagccca     900
aaagaacgaa aacccactcg gtccctaccg caagcccgac cagcgcttcg ccgtggaatc     960
ctacttggac taccaagcag acaagctagt acagcgtttc gacgccggct cctacgtctt    1020
gctcaccgac gccctcaacc gccacgacat tggtcgcgac cgcggaggcc tcaacaaggc    1080
actcgaatcc atcaaagttc cagtccttgt cgcaggcgta gataccgata ttttgtaccc    1140
ctaccaccag caagaacacc tctccagaaa cctgggaaat ctactggcaa tggcaaaaat    1200
cgtatcccct gtcggccacg atgctttcct caccgaaagc cgccaaatgg atcgcatcgt    1260
gaggaacttc ttcagcctca tctccccaga cgaagacaac ccttcgacct acatcgagtt    1320
ctacatctaa catatgacta gttcggacct agggatatcg tcgacatcga tgctcttctg    1380
cgttaattaa caattgggat cctctagacc cgggatttaa atcgctagcg ggctgctaaa    1440
ggaagcggaa cacgtagaaa gccagtccgc agaaacggtg ctgaccccgg atgaatgtca    1500
gctactgggc tatctggaca agggaaaacg caagcgcaaa gagaaagcag gtagcttgca    1560
gtgggcttac atggcgatag ctagactggg cggttttatg gacagcaagc gaaccggaat    1620
tgccagctgg ggcgccctct ggtaaggttg gaagccctg caaagtaaac tggatggctt    1680
tcttgccgcc aaggatctga tggcgcaggg gatcaagatc tgatcaagag acaggatgag    1740
gatcgtttcg catgattgaa caagatggat tgcacgcagg ttctccggcc gcttgggtgg    1800
agaggctatt cggctatgac tgggcacaac agacaatcgg ctgctctgat gccgccgtgt    1860
tccggctgtc agcgcagggg cgcccggttc tttttgtcaa gaccgacctg tccggtgccc    1920
tgaatgaact gcaggacgag gcagcgcggc tatcgtggct ggccacgacg gcgttccttt    1980
gcgcagctgt gctcgacgtt gtcactgaag cgggaaggga ctggctgcta ttgggcgaag    2040
tgccggggca ggatctcctg tcatctcacc ttgctcctgc cgagaaagta tccatcatgg    2100
ctgatgcaat gcggcggctg catacgcttg atccggctac ctgcccattc gaccaccaag    2160
cgaaacatcg catcgagcga gcacgtactc ggatggaagc cggtcttgtc gatcaggatg    2220
atctggacga agagcatcag gggctcgcgc cagccgaact gttcgccagg ctcaaggcgc    2280
gcatgcccga cggcgaggat ctcgtcgtga cccatggcga tgcctgcttg ccgaatatca    2340
```

```
tggtggaaaa tggccgcttt tctggattca tcgactgtgg ccggctgggt gtggcggacc    2400
gctatcagga catagcgttg gctacccgtg atattgctga agagcttggc ggcgaatggg    2460
ctgaccgctt cctcgtgctt tacggtatcg ccgctcccga ttcgcagcgc atcgccttct    2520
atcgccttct tgacgagttc ttctgagcgg gactctgggg ttcgaaatga ccgaccaagc    2580
gacgcccaac ctgccatcac gagatttcga ttccaccgcc gccttctatg aaaggttggg    2640
cttcggaatc gttttccggg acgccggctg gatgatcctc cagcgcgggg atctcatgct    2700
ggagttcttc gcccacgcta gcggcgcgcc ggccggcccg gtgtgaaata ccgcacagat    2760
gcgtaaggag aaaataccgc atcaggcgct cttccgcttc ctcgctcact gactcgctgc    2820
gctcggtcgt tcggctgcgg cgagcggtat cagctcactc aaaggcggta atacggttat    2880
ccacagaatc aggggataac gcaggaaaga acatgtgagc aaaaggccag caaaaggcca    2940
ggaaccgtaa aaaggccgcg ttgctggcgt ttttccatag gctccgcccc cctgacgagc    3000
atcacaaaaa tcgacgctca agtcagaggt ggcgaaaccc gacaggacta taaagatacc    3060
aggcgtttcc ccctggaagc tccctcgtgc gctctcctgt tccgaccctg ccgcttaccg    3120
gatacctgtc cgcctttctc ccttcgggaa gcgtggcgct ttctcatagc tcacgctgta    3180
ggtatctcag ttcggtgtag gtcgttcgct ccaagctggg ctgtgtgcac gaaccccccg    3240
ttcagcccga ccgctgcgcc ttatccggta actatcgtct tgagtccaac ccggtaagac    3300
acgacttatc gccactggca gcagccactg gtaacaggat tagcagagcg aggtatgtag    3360
gcggtgctac agagttcttg aagtggtggc ctaactacgg ctacactaga aggacagtat    3420
ttggtatctg cgctctgctg aagccagtta ccttcggaaa aagagttggt agctcttgat    3480
ccggcaaaca aaccaccgct ggtagcggtg gtttttttgt ttgcaagcag cagattacgc    3540
gcagaaaaaa aggatctcaa gaagatcctt tgatcttttc tacggggtct gacgctcagt    3600
ggaacgaaaa ctcacgttaa gggattttgg tcatgagatt atcaaaaagg atcttcacct    3660
agatcctttt aaaggccggc cgcggccgcg caaagtcccg cttcgtgaaa attttcgtgc    3720
cgcgtgattt tccgccaaaa actttaacga acgttcgtta taatggtgtc atgaccttca    3780
cgacgaagta ctaaaattgg cccgaatcat cagctatgga tctctctgat gtcgcgctgg    3840
agtccgacgc gctcgatgct gccgtcgatt taaaaacggt gatcggattt ttccgagctc    3900
tcgatacgac ggacgcgcca gcatcacgag actgggccag tgccgcgagc gacctagaaa    3960
ctctcgtggc ggatcttgag gagctggctg acgagctgcg tgctcggcca gcgcaggag    4020 gacgcacagt agtggaggat gcaatcagtt gcgcctactg cggtggcctg attcctcccc    4080
ggcctgaccc gcgaggacgg cgcgcaaaat attgctcaga tgcgtgtcgt gccgcagcca    4140
gccgcgagcg cgccaacaaa cgccacgccg aggagctgga ggcggctagg tcgcaaatgg    4200
cgctggaagt gcgtccccg agcgaaattt tggccatggt cgtcacagag ctggaagcgg    4260
cagcgagaat tatcgcgatc gtggcggtgc ccgcaggcat gacaaacatc gtaaatgccg    4320
cgtttcgtgt gccgtggccg cccaggacgt gtcagcgccg ccaccacctg caccgaatcg    4380
gcagcagcgt cgcgcgtcga aaagcgcac aggcggcaag aagcgataag ctgcacgaat    4440
acctgaaaaa tgttgaacgc cccgtgagcg gtaactcaca gggcgtcggc taaccccag    4500 tccaaacctg ggagaaagcg ctcaaaaatg actctagcgg attcacgaga cattgacaca    4560
ccggcctgga aatttccgc tgatctgttc gacacccatc ccgagctcgc gctgcgatca    4620
cgtggctgga cgagcgaaga ccgccgcgaa ttcctcgctc acctgggcag agaaaatttc    4680
cagggcagca agacccgcga cttcgccagc gcttggatca aagacccgga cacggagaaa    4740
```

| | |
|---|---|
| cacagccgaa gttataccga gttggttcaa aatcgcttgc ccggtgccag tatgttgctc | 4800 |
| tgacgcacgc gcagcacgca gccgtgcttg tcctggacat tgatgtgccg agccaccagg | 4860 |
| ccggcgggaa aatcgagcac gtaaaccccg aggtctacgc gattttggag cgctgggcac | 4920 |
| gcctggaaaa agcgccagct tggatcggcg tgaatccact gagcgggaaa tgccagctca | 4980 |
| tctggctcat tgatccggtg tatgccgcag caggcatgag cagcccgaat atgcgcctgc | 5040 |
| tggctgcaac gaccgaggaa atgacccgcg ttttcggcgc tgaccaggct ttttcacata | 5100 |
| ggctgagccg tggccactgc actctccgac gatcccagcc gtaccgctgg catgcccagc | 5160 |
| acaatcgcgt ggatcgccta gctgatctta tggaggttgc tcgcatgatc tcaggcacag | 5220 |
| aaaaacctaa aaaacgctat gagcaggagt tttctagcgg acgggcacgt atcgaagcgg | 5280 |
| caagaaaagc cactgcggaa gcaaaagcac ttgccacgct tgaagcaagc ctgccgagcg | 5340 |
| ccgctgaagc gtctggagag ctgatcgacg gcgtccgtgt cctctggact gctccagggc | 5400 |
| gtgccgcccg tgatgagacg gcttttcgcc acgctttgac tgtgggatac cagttaaaag | 5460 |
| cggctggtga gcgcctaaaa gacaccaagg gtcatcgagc ctacgagcgt gcctacaccg | 5520 |
| tcgctcaggc ggtcggagga ggccgtgagc ctgatctgcc gccggactgt gaccgccaga | 5580 |
| cggattggcc gcgacgtgtg cgcggctacg tcgctaaagg ccagccagtc gtccctgctc | 5640 |
| gtcagacaga gacgcagagc cagccgaggc gaaaagctct ggccactatg gaagacgtg | 5700 |
| gcggtaaaaa ggccgcagaa cgctggaaag acccaaacag tgagtacgcc cgagcacagc | 5760 |
| gagaaaaact agctaagtcc agtcaacgac aagctaggaa agctaaagga aatcgcttga | 5820 |
| ccattgcagg ttggtttatg actgttgagg gagagactgg ctcgtggccg acaatcaatg | 5880 |
| aagctatgtc tgaatttagc gtgtcacgtc agaccgtgaa tagagcactt aaggtctgcg | 5940 |
| ggcattgaac ttccacgagg acgccgaaag cttcccagta aatgtgccat ctcgtaggca | 6000 |
| gaaaacggtt cccccgtagg gtctctctct tggcctcctt tctaggtcgg gctgattgct | 6060 |
| cttgaagctc tctagggggg ctcacaccat aggcagataa cgttccccac cggctcgcct | 6120 |
| cgtaagcgca caaggactgc tcccaaagat cttcaaagcc actgccgcga ctgccttcgc | 6180 |
| gaagccttgc cccgcggaaa tttcctccac cgagttcgtg cacacccta tgccaagctt | 6240 |
| ctttcaccct aaattcgaga gattggattc ttaccgtgga aattcttcgc aaaaatcgtc | 6300 |
| ccctgatcgc ccttgcgacg ttggcgtcgg tgccgctggt tgcgcttggc ttgaccgact | 6360 |
| tgatcagcgg ccgctcgatt taaatc | 6386 |

<210> SEQ ID NO 40
<211> LENGTH: 1005
<212> TYPE: DNA
<213> ORGANISM: Corynebacterium glutamicum
<220> FEATURE:
<223> OTHER INFORMATION: FRUCTOSE-1,6-BISPHOSPHATASE

<400> SEQUENCE: 40

| | |
|---|---|
| atgaacctaa agaaccccga acgccagac cgtaaccttg ctatggagct ggtgcgagtt | 60 |
| acggaagcag ctgcactggc ttctggacgt tgggttggac gtggcatgaa gaatgaaggc | 120 |
| gacggtgccg ctgttgacgc catgcgccag ctcatcaact cagtgaccat gaagggcgtc | 180 |
| gttgttatcg gcgagggcga aaagacgaa gctccaatgc tgtacaacgg cgaagaggtc | 240 |
| ggaaccggct ttggacctga ggttgatatc gcagttgacc cagttgacgg caccaccctg | 300 |
| atggctgagg gtcgccccaa cgcaatttcc attctcgcag ctgcagagcg tggcaccatg | 360 |
| tacgatccat cctccgtctt ctacatgaag aagatcgccg tgggacctga ggccgcaggc | 420 |

```
aagatcgaca tcgaagctcc agttgcccac aacatcaacg cggtggcaaa gtccaaggga    480
atcaacccct ccgacgtcac cgttgtcgtg cttgaccgtc ctcgccacat cgaactgatc    540
gcagacattc gtcgtgcagg cgcaaaggtt cgtctcatct ccgacggcga cgttgcaggt    600
gcagttgcag cagctcagga ttccaactcc gtggacatca tgatgggcac cggcggaacc    660
ccagaaggca tcatcactgc gtgcgccatg aagtgcatgg gtggcgaaat ccagggcatc    720
ctggccccaa tgaacgattt cgagcgccag aaggcacacg acgctggtct ggttcttgat    780
caggttctgc acaccaacga tctggtgagc tccgacaact gctacttcgt ggcaaccggt    840
gtgaccaacg gtgacatgct ccgtggcgtt tcctaccgcg caaacggcgc aaccacccgt    900
tccctggtta tgcgcgcaaa gtcaggcacc atccgccaca tcgagtctgt ccaccagctg    960
tccaagctgc aggaatactc cgtggttgac tacaccaccg cgacc                   1005
```

<210> SEQ ID NO 41
<211> LENGTH: 335
<212> TYPE: PRT
<213> ORGANISM: Corynebacterium glutamicum

<400> SEQUENCE: 41

```
Met Asn Leu Lys Asn Pro Glu Thr Pro Asp Arg Asn Leu Ala Met Glu
  1               5                  10                  15

Leu Val Arg Val Thr Glu Ala Ala Leu Ala Ser Gly Arg Trp Val
             20                  25                  30

Gly Arg Gly Met Lys Asn Glu Gly Asp Gly Ala Ala Val Asp Ala Met
         35                  40                  45

Arg Gln Leu Ile Asn Ser Val Thr Met Lys Gly Val Val Ile Gly
     50                  55                  60

Glu Gly Glu Lys Asp Glu Ala Pro Met Leu Tyr Asn Gly Glu Glu Val
 65                  70                  75                  80

Gly Thr Gly Phe Gly Pro Glu Val Asp Ile Ala Val Asp Pro Val Asp
                 85                  90                  95

Gly Thr Thr Leu Met Ala Glu Gly Arg Pro Asn Ala Ile Ser Ile Leu
            100                 105                 110

Ala Ala Ala Glu Arg Gly Thr Met Tyr Asp Pro Ser Ser Val Phe Tyr
        115                 120                 125

Met Lys Lys Ile Ala Val Gly Pro Glu Ala Ala Lys Ile Asp Ile
130                 135                 140

Glu Ala Pro Val Ala His Asn Ile Asn Ala Val Ala Lys Ser Lys Gly
145                 150                 155                 160

Ile Asn Pro Ser Asp Val Thr Val Val Leu Asp Arg Pro Arg His
                165                 170                 175

Ile Glu Leu Ile Ala Asp Ile Arg Arg Ala Gly Ala Lys Val Arg Leu
            180                 185                 190

Ile Ser Asp Gly Asp Val Ala Gly Ala Val Ala Ala Gln Asp Ser
        195                 200                 205

Asn Ser Val Asp Ile Met Met Gly Thr Gly Gly Thr Pro Glu Gly Ile
210                 215                 220

Ile Thr Ala Cys Ala Met Lys Cys Met Gly Gly Glu Ile Gln Gly Ile
225                 230                 235                 240

Leu Ala Pro Met Asn Asp Phe Glu Arg Gln Lys Ala His Asp Ala Gly
                245                 250                 255

Leu Val Leu Asp Gln Val Leu His Thr Asn Asp Leu Val Ser Ser Asp
            260                 265                 270
```

```
Asn Cys Tyr Phe Val Ala Thr Gly Val Thr Asn Gly Asp Met Leu Arg
        275                 280                 285

Gly Val Ser Tyr Arg Ala Asn Gly Ala Thr Thr Arg Ser Leu Val Met
    290                 295                 300

Arg Ala Lys Ser Gly Thr Ile Arg His Ile Glu Ser Val His Gln Leu
305                 310                 315                 320

Ser Lys Leu Gln Glu Tyr Ser Val Val Asp Tyr Thr Thr Ala Thr
                325                 330                 335

<210> SEQ ID NO 42
<211> LENGTH: 6
<212> TYPE: DNA
<213> ORGANISM: Corynebacterium glutamicum
<220> FEATURE:
<223> OTHER INFORMATION: -10-REGION_1

<400> SEQUENCE: 42 tgcaat                                                              6

<210> SEQ ID NO 43
<211> LENGTH: 7
<212> TYPE: DNA
<213> ORGANISM: Corynebacterium glutamicum
<220> FEATURE:
<223> OTHER INFORMATION: -10-REGION_2

<400> SEQUENCE: 43 tatcatt                                                             7

<210> SEQ ID NO 44
<211> LENGTH: 7
<212> TYPE: DNA
<213> ORGANISM: Corynebacterium glutamicum
<220> FEATURE:
<223> OTHER INFORMATION: RIBOSOME BINDING Site

<400> SEQUENCE: 44 gaaagga                                                             7
```

PSOD EXPRESSION UNITS

RELATED APPLICATIONS

This application is a divisional of U.S. application Ser. No. 10/583,191, filed Jun. 14, 2006, now abandoned, which is a 35 U.S.C. 371 National stage filing of International Application No. PCT/EP2004/014337, filed Dec. 16, 2004, which claims priority to German Application No. 103 59 660.7, filed Dec. 18, 2003. The entire contents of each of these applications are hereby incorporated by reference herein.

SEQUENCE LISTING SUBMISSION

The Sequence Listing associated with this application is filed in electronic format via EFS-Web and hereby incorporated by reference into the specification in its entirety. The name of the text file containing the Sequence Listing is Sequence List__12810__00674_US. The size of the text file is 80 KB, and the text file was created on Aug. 4, 2008.

SPECIFICATION

The present invention relates to the use of nucleic acid sequences for regulating the transcription and expression of genes, the novel promoters and expression units themselves, methods for altering or causing the transcription rate and/or expression rate of genes, expression cassettes comprising the expression units, genetically modified microorganisms with altered or caused transcription rate and/or expression rate, and methods for preparing biosynthetic products by cultivating the genetically modified microorganisms.

Various biosynthetic products such as, for example, fine chemicals, such as, inter alia, amino acids, vitamins, but also proteins, are produced in cells by natural metabolic processes and are used in many branches of industry, including the cosmetics, feed, food and pharmaceutical industries. These substances, which are referred to collectively as fine chemicals/proteins, comprise inter alia organic acids, both proteinogenic and non-proteinogenic amino acids, nucleotides and nucleosides, lipids and fatty acids, diols, carbohydrates, aromatic compounds, vitamins and cofactors, and proteins and enzymes. Their production takes place most expediently on the industrial scale by culturing bacteria which have been developed in order to produce and secrete large quantities of the particular desired substance. Organisms particularly suitable for this purpose are coryneform bacteria, gram-positive non-pathogenic bacteria.

It is known that amino acids are prepared by fermentation of strains of coryneform bacteria, especially *Corynebacterium glutamicum*. Because of the great importance, continuous work is done on improving the production processes. Process improvements may relate to fermentation technique measures such as, for example, stirring and oxygen supply, or the composition of the nutrient media, such as, for example, the sugar concentration during the fermentation, or the working up to give the product, for example by ion exchange chromatography or else spray drying, or the intrinsic performance properties of the microorganism itself.

Methods of recombinant DNA technology have likewise been employed for some years for strain improvement of *Corynebacterium* strains producing fine chemical/proteins, by amplifying individual genes and investigating the effect on the production of fine chemicals/proteins.

Other ways for developing a process for producing fine chemicals, amino acids or proteins, or for increasing or improving the productivity of a pre-existing process for producing fine chemicals, amino acids or proteins, include increasing or to altering the expression of one or more genes, and/or influencing the translation of an mRNA by suitable polynucleotide sequences. In this connection, influencing the translation of an mRNA may include increasing or reducing other parameters of the expression of genes, such as chronological expression patterns.

Various constituents of bacterial regulatory sequences are known to the skilled worker. A distinction is made between the binding sites for regulators, also called operators, the binding sites for RNA polymerase holoenzymes, also called −35 and −10 regions, and the binding site for ribosomal 16S RNA, also called ribosome binding site or else Shine-Dalgarno sequence.

The sequence of a ribosome binding site, also called Shine-Dalgarno sequence, means for the purposes of this invention polynucleotide sequences which are located up to 20 bases upstream of the translation initiation codon.

In the literature (*E. coli* and *S. typhimurium*, Neidhardt F. C. 1995 ASM Press) it is reported that both the composition of the polynucleotide sequence of the Shine-Dalgarno sequence, the sequence string of the bases, but also the distance of a polynucleotide sequence present in the Shine-Dalgarno sequence from has a considerable influence on the translation initiation rate.

Nucleic acid sequences having promoter activity can influence the formation of mRNA in various ways. Promoters whose activities are independent of the physiological growth phase of the organism are called constitutive. Other promoters in turn respond to external chemical and physical stimuli such as oxygen, metabolites, heat, pH, etc.

Others in turn show a strong dependence of their activity in different growth phases. For example, promoters showing a particularly pronounced activity during the exponential growth phase of microorganisms, or else precisely in the stationary phase of microbial growth, are described in the literature. Both characteristics of promoters may have a beneficial effect on productivity for a production of fine chemicals and proteins, depending on the metabolic pathway.

For example, promoters which switch off the expression of a gene during growth, but switch it on after an optimal growth, can be used to regulate a gene which controls the production of a metabolite. The modified strain then displays the same growth parameters as the starting strain but produces more product per cell. This type of modification may increase both the titer (g of product/liter) and the C yield (g of product/g of C source).

It has already been possible to isolate in *Corynebacterium* species those nucleotide sequences which can be used to increase or diminish gene expression. These regulated promoters may increase or reduce the rate at which a gene is transcribed, depending on the internal and/or external conditions of the cell. In some cases, the presence of a particular factor, known as inducer, can stimulate the rate of transcription from the promoter. Inducers may influence transcription from the promoter either directly or indirectly. Another class of factors, known as suppressors, is able to reduce or else inhibit the transcription from the promoter. Like the inducers, the suppressors can also act directly or indirectly. However, temperature-regulated promoters are also known. Thus, the level of transcription of such promoters can be increased or else diminished for example by increasing the growth temperature above the normal growth temperature of the cell.

A small number of promoters from *C. glutamicum* have been described to date. The promoter of the malate synthase gene from *C. glutamicum* was described in DE 4440118. This promoter was inserted upstream of a structural gene coding for a protein. After transformation of such a construct into a coryneform bacterium there is regulation of the expression of the structural gene downstream of the promoter. Expression of the structural gene is induced as soon as an appropriate inducer is added to the medium.

Reinscheid et al., Microbiology 145:503 (1999) described a transcriptional fusion between the pta-ack promoter from *C. glutamicum* and a reporter gene (chloramphenicol acetyltransferase). Cells of *C. glutamicum* comprising such a transcriptional fusion exhibited increased expression of the reporter gene on growth on acetate-containing medium. By comparison with this, transformed cells which grew on glucose showed no increased expression of this reporter gene.

Pa'tek et al., Microbiology 142:1297 (1996) describe some DNA sequences from *C. glutamicum* which are able to enhance the expression of a reporter gene in *C. glutamicum* cells. These sequences were compared together in order to define consensus sequences for *C. glutamicum* promoters.

Further DNA sequences from *C. glutamicum* which can be used to regulate gene expression have been described in the patent WO 02/40679. These isolated polynucleotides represent expression units from *Corynebacterium glutamicum* which can be used either to increase or else to reduce gene expression. This patent additionally describes recombinant plasmids on which the expression units from *Corynebacterium glutamicum* are associated with heterologous genes. The method described herein, of fusing a promoter from *Corynebacterium glutamicum* with a heterologous gene, can be employed inter alia for regulating the genes of amino acid biosynthesis.

It is an object of the present invention to provide further promoters and/or expression units with advantageous properties.

We have found that this object is achieved by the use of a nucleic acid having promoter activity, comprising A) the nucleic acid sequence SEQ. ID. NO. 1 or
B) a sequence derived from this sequence by substitution, insertion or deletion of nucleotides and having an identity of at least 90% at the nucleic acid level with the sequence SEQ. ID. NO. 1,
or
C) a nucleic acid sequence which hybridizes with the nucleic acid sequence SEQ. ID. NO. 1 under stringent conditions, or
D) functionally equivalent fragments of the sequences of A), B) or C)

for the transcription of genes.

"Transcription" means according to the invention the process by which a complementary RNA molecule is produced starting from a DNA template. Proteins such as RNA polymerase, so-called sigma factors and transcriptional regulator proteins are involved in this process. The synthesized RNA is then used as template in the translation process, which then leads to the biosynthetically active protein.

The formation rate with which a biosynthetically active protein is produced is a product of the rate of transcription and of translation. Both rates can be influenced according to the invention, and thus influence the rate of formation of products in a microorganism.

A "promoter" or a "nucleic acid having promoter activity" means according to the invention a nucleic acid which, in a functional linkage to a nucleic acid to be transcribed, regulates the transcription of this nucleic acid.

A "functional linkage" means in this connection for example the sequential arrangement of one of the nucleic acids of the invention having promoter activity and a nucleic acid sequence to be transcribed and, where appropriate, further regulatory elements such as, for example, nucleic acid sequences which ensure the transcription of nucleic acids, and for example a terminator, in such a way that each of the regulatory elements is able to fulfill its function in the transcription of the nucleic acid sequence. A direct linkage in the chemical sense is not absolutely necessary therefor. Genetic control sequences, such as, for example, enhancer sequences, are able to exercise their function on the target sequence even from more remote positions or even from other DNA molecules. Arrangements in which the nucleic acid sequence to be transcribed is positioned behind (i.e. at the 3' end) of the promoter sequence of the invention, so that the two sequences are covalently connected together, are preferred. In this connection, the distance between the promoter sequence and the nucleic acid sequence to be expressed transgenically is preferably fewer than 200 base pairs, particularly preferably less than 100 base pairs, very particularly preferably less than 50 base pairs.

"Promoter activity" means according to the invention the quantity of RNA formed by the promoter in a particular time, that is to say the transcription rate.

"Specific promoter activity" means according to the invention the quantity of RNA formed by the promoter in a particular time for each promoter.

The term "wild type" means according to the invention the appropriate starting microorganism.

Depending on the context, the term "microorganism" means the starting microorganism (wild type) or a genetically modified microorganism of the invention, or both.

Preferably, and especially in cases where the microorganism or the wild type cannot be unambiguously assigned, "wild type" means for the alteration or causing of the promoter activity or transcription rate, for the alteration of causing of the expression activity or expression rate and for increasing the content of biosynthetic products in each case a reference organism.

In a preferred embodiment, this reference organism is *Corynebacterium glutamicum* ATCC 13032.

In a preferred embodiment, the starting microorganisms used are already able to produce the desired fine chemical. Particular preference is given in this connection among the particularly preferred microorganisms of bacteria of the genus *Corynebacterium* and the particularly preferred fine chemicals L-lysine, L-methionine and L-threonine to those starting microorganisms already able to produce L-lysine, L-methionine and/or L-threonine. These are particularly preferably corynebacteria in which, for example, the gene coding for an aspartokinase (ask gene) is deregulated or the feedback inhibition is abolished or reduced. Such bacteria have, for example, a mutation leading to a reduction or abolition of the feedback inhibition, such as, for example, the mutation T311I, in the ask gene.

In the case of a "caused promoter activity" or transcription rate in relation to a gene compared with the wild type, therefore, compared with the wild type the formation of an RNA which was not present in this way in the wild type is caused.

In the case of an altered promoter activity or transcription rate in relation to a gene compared with the wild type, therefore, compared with the wild type the quantity of RNA produced in a particular time is altered.

"Altered" means in this connection preferably increased or reduced.

This can take place for example by increasing or reducing the specific promoter activity of the endogenous promoter of the invention, for example by mutating the promoter or by stimulating or inhibiting the promoter.

A further possibility is to achieve the increased promoter activity or transcription rate for example by regulating the transcription of genes in the microorganism by nucleic acids of the invention having promoter activity or by nucleic acids with increased specific promoter activity, where the genes are heterologous in relation to the nucleic acids having promoter activity.

The regulation of the transcription of genes in the microorganism by nucleic acids of the invention having promoter activity or by nucleic acids with increased specific promoter activity is preferably achieved by
introducing one or more nucleic acids of the invention having promoter activity, appropriate with altered specific promoter activity, into the genome of the microorganism so that transcription of one or more endogenous genes takes place under the control of the introduced nucleic acid of the invention having promoter activity, appropriate with altered specific promoter activity, or
introducing one or more genes into the genome of the microorganism so that transcription of one or more of the introduced genes takes place under the control of the endogenous nucleic acids of the invention having promoter activity, where appropriate with altered specific promoter activity, or
introducing one or more nucleic acid constructs comprising a nucleic acid of the invention having promoter activity, where appropriate with altered specific promoter activity, and functionally linked one or more nucleic acids to be transcribed, into the microorganism.

The nucleic acids of the invention having promoter activity comprise
A) the nucleic acid sequence SEQ. ID. NO. 1 or
B) a sequence derived from this sequence by substitution, insertion or deletion of nucleotides and having an identity of at least 90% at the nucleic acid level with the sequence SEQ. ID. NO. 1,
or
C) a nucleic acid sequence which hybridizes with the nucleic acid sequence SEQ. ID. NO. 1 under stringent conditions, or
D) functionally equivalent fragments of the sequences of A), B) or C).

The nucleic acid sequence SEQ. ID. NO. 1 represents the promoter sequence of superoxide dismutase (Psod) from *Corynebacterium glutamicum*. SEQ. ID. NO. 1 corresponds to the promoter sequence of the wild type.

The invention additionally relates to nucleic acids having promoter activity comprising a sequence derived from this sequence by substitution, insertion or deletion of nucleotides and having an identity of at least 90% at the nucleic acid level with the sequence SEQ. ID. NO. 1.

Further natural examples of the invention for promoters of the invention can easily be found for example from various organisms whose genomic sequence is known, by identity comparisons of the nucleic acid sequences from databases with the sequence SEQ ID NO: 1 described above.

Artificial promoter sequences of the invention can easily be found starting from the sequence SEQ ID NO: 1 by artificial variation and mutation, for example by substitution, insertion or deletion of nucleotides.

The term "substitution" means in the description the replacement of one or more nucleotides by one or more nucleotides. "Deletion" is the replacement of a nucleotide by a direct linkage. Insertions are insertions of nucleotides into the nucleic acid sequence, with formal replacement of a direct linkage by one or more nucleotides.

Identity between two nucleic acids means the identity of the nucleotides over the complete length of the nucleic acid in each case, in particular the identity calculated by comparison with the aid of the vector NTI Suite 7.1 software from Informax (USA) using the Clustal method (Higgins D G, Sharp P M. Fast and sensitive multiple sequence alignments on a microcomputer. Comput Appl. Biosci. 1989 April; 5(2):151-1), setting the following parameters:

| Multiple alignment parameter: | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |
| Pairwise alignment parameter: | |
| FAST algorithm | on |
| K-tuple size | 1 |
| Gap penalty | 3 |
| Window size | 5 |
| Number of best diagonals | 5 |

A nucleic acid sequence having an identity of at least 90% with the sequence SEQ ID NO: 1 accordingly means a nucleic acid sequence which, on comparison of its sequence with the sequence SEQ ID NO: 1, in particular in accordance with the above programming algorithm with the above parameter set, shows an identity of at least 90%.

Particularly preferred promoters show an identity of 91%, more preferably 92%, 93%, 94%, 95%, 96%, 97%, 98%, particularly preferably 99%, with the nucleic acid sequence SEQ. ID. NO. 1.

Further natural examples of promoters can moreover easily be found starting from the nucleic acid sequences described above, in particular starting from the sequence SEQ ID NO: 1 from various organisms whose genomic sequence is unknown, by hybridization techniques in a manner known per se.

A further aspect of the invention therefore relates to nucleic acids having promoter activity comprising a nucleic acid sequence which hybridizes with the nucleic acid sequence SEQ. ID. No. 1 under stringent conditions. This nucleic acid sequence comprises at least 10, more preferably more than 12, 15, 30, 50 or particularly preferably more than 150, nucleotides.

The hybridization takes place according to the invention under stringent conditions. Such hybridization conditions are described for example in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6:

Stringent hybridization conditions mean in particular: incubation at 42° C. overnight in a solution consisting of 50% formamide, 5×SSC (750 mM NaCl, 75 mM trisodium citrate), 50 mM sodium phosphate (pH 7.6), 5×Denhardt's solution, 10% dextran sulfate and 20 g/ml denatured, sheared salmon sperm DNA, followed by washing the filters with 0.1×SSC at 65° C.

A "functionally equivalent fragment" means for nucleic acid sequences having promoter activity fragments which have substantially the same or a higher specific promoter activity than the starting sequence.

"Essentially identical" means a specific promoter activity which displays at least 50%, preferably 60%, more preferably 70%, more preferably 80%, more preferably 90%, particularly preferably 95% of the specific promoter activity of the starting sequence.

"Fragments" mean partial sequences of the nucleic acids having promoter activity which are described by embodiment A), B) or C). These fragments preferably have more than 10, but more preferably more than 12, 15, 30, 50 or particularly preferably more than 150, connected nucleotides of the nucleic acid sequence SEQ. ID. NO. 1.

It is particularly preferred to use the nucleic acid sequence SEQ. ID. NO. 1 as promoter, i.e. for transcription of genes.

SEQ. ID. NO. 1 has been described without assignment of function in the Genbank entry AP005283. The invention therefore further relates to the novel nucleic acid sequences of the invention having promoter activity.

The invention relates in particular to a nucleic acid having promoter activity, comprising
- A) the nucleic acid sequence SEQ. ID. NO 1 or
- B) a sequence derived from this sequence by substitution, insertion or deletion of nucleotides and having an identity of at least 90% at the nucleic acid level with the sequence SEQ. ID. NO. 1, or
- C) a nucleic acid sequence which hybridizes with the nucleic acid sequence SEQ. ID. NO 1 under stringent conditions, or
- D) functionally equivalent fragments of the sequences of A), B) or C), with the proviso that the nucleic acid having the sequence SEQ. ID. NO. 1 is excluded.

All the nucleic acids having promoter activity which are mentioned above can additionally be prepared in a manner known per se by chemical synthesis from the nucleotide building blocks such as, for example, by fragment condensation of individual overlapping complementary nucleic acid building blocks of the double helix. The chemical synthesis of oligonucleotides can take place for example in known manner by the phosphoramidite method (Voet, Voet, 2nd edition, Wiley Press New York, pp. 896-897). Addition of synthetic oligonucleotides and filling in of gaps using the Klenow fragment of DNA polymerase and ligation reactions, and general cloning methods, are described in Sambrook et al. (1989), Molecular cloning: A laboratory manual, Cold Spring Harbor Laboratory Press.

The invention further relates to the use of an expression unit comprising one of the nucleic acids of the invention having promoter activity and additionally functionally linked a nucleic acid sequence which ensures the translation of ribonucleic acids for the expression of genes.

An expression unit means according to the invention a nucleic acid having expression activity, i.e a nucleic acid which, in functional linkage to a nucleic acid to be expressed, or gene, regulates the expression, i.e. the transcription and the translation of this nucleic acid or of this gene.

A "functional linkage" means in this connection for example the sequential arrangement of one of the expression units of the invention and of a nucleic acid sequence which is to be expressed transgenically and, where appropriate, further regulatory elements such as, for example, a terminator in such a way that each of the regulatory elements can fulfill its function in the transgenic expression of the nucleic acid sequence. A direct linkage in the chemical sense is not absolutely necessary for this. Genetic control sequences, such as, for example, enhancer sequences, can exercise their function on the target sequence also from more remote positions or even from different DNA molecules. Arrangements in which the nucleic acid sequence to be expressed transgenically is positioned behind (i.e. at the 3' end) the expression unit sequence of the invention, so that the two sequences are covalently connected together, are preferred. It is preferred in this case for the distance between the expression unit sequence and the nucleic acid sequence to be expressed transgenically to be less than 200 base pairs, particularly preferably fewer than 100 base pairs, very particularly preferably fewer than 50 base pairs.

"Expression activity" means according to the invention the quantity of protein produced in a particular time by the expression unit, i.e. the expression rate.

"Specific expression activity" means according to the invention the quantity of protein produced by the expression unit in a particular time for each expression unit.

In the case of a "caused expression activity" or expression rate in relation to a gene compared with the wild type, therefore, compared with the wild type the production of a protein which was not present in this way in the wild type is caused.

In the case of an "altered expression activity" or expression rate in relation to a gene compared with the wild type, therefore, compared with the wild type the quantity of protein produced in a particular time is altered.

"Altered" preferably means in this connection increased or decreased.

This can take place for example by increasing or reducing the specific activity of the endogenous expression unit, for example by mutating the expression unit or by stimulating or inhibiting the expression unit.

The increased expression activity or expression rate can moreover be achieved for example by regulating the expression of genes in the microorganism by expression units of the invention or by expression units with increased specific expression activity, where the genes are heterologous in relation to the expression units.

The regulation of the expression of genes in the microorganism by expression units of the invention or by expression units of the invention with increased specific expression activity is preferably achieved by
introducing one or more expression units of the invention, where appropriate with altered specific expression activity, into the genome of the microorganism so that expression of one or more endogenous genes takes place under the control of the introduced expression units of the invention, where appropriate with altered specific expression activity, or
introducing one or more genes into the genome of the microorganism so that expression of one or more of the introduced genes takes place under the control of the endogenous expression units of the invention, where appropriate with altered specific expression activity, or
introducing one or more nucleic acid constructs comprising an expression unit of the invention, where appropriate with altered specific expression activity, and functionally linked one or more nucleic acids to be expressed, into the microorganism.

The expression units of the invention comprise a nucleic acid of the invention, described above, having promoter activity and additionally functionally linked a nucleic acid sequence which ensures the translation of ribonucleic acids.

This nucleic acid sequence which ensures the translation of ribonucleic acids preferably comprises the nucleic acid sequence SEQ. ID. NO. 42 as ribosome binding site.

In a preferred embodiment, the expression unit of the invention comprises:
- E) the nucleic acid sequence SEQ. ID. NO. 2 or
- F) a sequence derived from this sequence by substitution, insertion or deletion of nucleotides and having an identity of at least 90% at the nucleic acid level with the sequence SEQ. ID. NO. 2, or G) a nucleic acid sequence which hybridizes with the nucleic acid sequence SEQ. ID. NO. 2 under stringent conditions, or H) functionally equivalent fragments of the sequences of E), F) or G).

The nucleic acid sequence SEQ. ID. NO. 2 represents the nucleic acid sequence of the expression unit of superoxide dismutase (Psod) from *Corynebacterium glutamicum*. SEQ. ID. NO. 2 corresponds to the sequence of the expression unit of the wild type.

The invention further relates to expression units comprising a sequence which is derived from this sequence by substitution, insertion or deletion of nucleotides and which have an identity of at least 90% at the nucleic acid level with the sequence SEQ. ID. NO. 2.

Further natural examples of the invention for expression units of the invention can easily be found for example from various organisms whose genomic sequence is known, by identity comparisons of the nucleic acid sequences from databases with the sequence SEQ ID NO: 2 described above.

Artificial sequences of the invention of the expression units can easily be found starting from the sequence SEQ ID NO: 2 by artificial variation and mutation, for example by substitution, insertion or deletion of nucleotides.

A nucleic acid sequence having an identity of at least 90% with the sequence SEQ ID NO: 2 accordingly means a nucleic acid sequence which, on comparison of its sequence with the sequence SEQ ID NO: 2, in particular in accordance with the above programming algorithm with the above parameter set, shows an identity of at least 90%.

Particularly preferred expression units show an identity of 91%, more preferably 92%, 93%, 94%, 95%, 96%, 97%, 98%, particularly preferably 99%, with the nucleic acid sequence SEQ. ID. NO. 2.

Further natural examples of expression units can moreover easily be found starting from the nucleic acid sequences described above, in particular starting from the sequence SEQ ID NO: 2 from various organisms whose genomic sequence is unknown, by hybridization techniques in a manner known per se.

A further aspect of the invention therefore relates to expression units comprising a nucleic acid sequence which hybridizes with the nucleic acid sequence SEQ. ID. No. 2 under stringent conditions. This nucleic acid sequence comprises at least 10, more preferably more than 12, 15, 30, 50 or particularly preferably more than 150, nucleotides.

"Hybridization" means the ability of a poly- or oligonucleotide to bind under stringent conditions to a virtually complementary sequence, while nonspecific bindings between non-complementary partners do not occur under these conditions. For this, the sequences ought preferably to be 90-100% complementary. The property of complementary sequences being able to bind specifically to one another is made use of for example in the Northern or Southern blotting technique or in primer binding in PCR or RT-PCR.

The hybridization takes place according to the invention under stringent conditions. Such hybridization conditions are described for example in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6:

Stringent hybridization conditions mean in particular: incubation at 42° C. overnight in a solution consisting of 50% formamide, 5×SSC (750 mM NaCl, 75 mM trisodium citrate), 50 mM sodium phosphate (pH 7.6), 5×Denhardt's solution, 10% dextran sulfate and 20 g/ml denatured, sheared salmon sperm DNA, followed by washing the filters with 0.1×SSC at 65° C.

The nucleotide sequences of the invention further make it possible to produce probes and primers which can be used for identifying and/or cloning homologous sequences in other cell types and microorganisms. Such probes and primers normally comprise a nucleotide sequence region which hybridizes under stringent conditions onto a least approximately 12, preferably at least approximately 25, such as, for example, approximately 40, 50 or 75 consecutive nucleotides of a sense strand of a nucleic acid sequence of the invention or of a corresponding antisense strand.

Also comprised according to the invention are nucleic acid sequences which comprise so-called silent mutations or are modified in accordance with the codon usage of a specific original or host organism compared with a specifically mentioned sequence, as well as naturally occurring variants such as, for example, splice variants or allelic variants, thereof.

A "functionally equivalent fragment" means for expression units fragments which have substantially the same or a higher specific expression activity than the starting sequence.

"Essentially identical" means a specific expression activity which displays at least 50%, preferably 60%, more preferably 70%, more preferably 80%, more preferably 90%, particularly preferably 95% of the specific expression activity of the starting sequence.

"Fragments" mean partial sequences of the expression units which are described by embodiment E), F) or G). These fragments preferably have more than 10, but more preferably more than 12, 15, 30, 50 or particularly preferably more than 150, connected nucleotides of the nucleic acid sequence SEQ. ID. NO 1.

It is particularly preferred to use the nucleic acid sequence SEQ. ID. NO. 2 as expression unit, i.e. for expression of genes.

SEQ. ID. NO. 2 has been described without assignment of function in the Genbank entry AP005283. The invention therefore further relates to the novel expression units of the invention.

The invention relates in particular to an expression unit comprising a nucleic acid of the invention having promoter activity and additionally functionally linked a nucleic acid sequence which ensures the translation of ribonucleic acids.

The invention particularly preferably relates to an expression unit comprising

E) the nucleic acid sequence SEQ. ID. NO. 2 or

F) a sequence derived from this sequence by substitution, insertion or deletion of nucleotides and having an identity of at least 90% at the nucleic acid level with the sequence SEQ. ID. NO. 2, or G) a nucleic acid sequence which hybridizes with the nucleic acid sequence SEQ. ID. NO. 2 under stringent conditions, or H) functionally equivalent fragments of the sequences of E), F) or G), with the proviso that the nucleic acid having the sequence SEQ. ID. NO. 2 is excluded.

The expression units of the invention comprise one or more of the following genetic elements: a minus 10 ("−10") sequence; a minus 35 ("−35") sequence; a transcription sequence start, an enhancer region; and an operator region.

These genetic elements are preferably specific for species of corynebacteria, especially for *Corynbacterium glutamicum*.

All the expression units which are mentioned above can additionally be prepared in a manner known per se by chemical synthesis from the nucleotide building blocks such as, for example, by fragment condensation of individual overlapping complementary nucleic acid building blocks of the double helix. The chemical synthesis of oligonucleotides can take place for example in known manner by the phosphoramidite method (Voet, Voet, 2nd edition, Wiley Press New York, pp. 896-897). Addition of synthetic oligonucleotides and filling in of gaps using the Klenow fragment of DNA polymerase and ligation reactions, and general cloning methods, are described in Sambrook et al. (1989), Molecular cloning: A laboratory manual, Cold Spring Harbor Laboratory Press.

The methods and techniques used for the inventions in this patent are known to the skilled worker trained in microbiological and recombinant DNA techniques. Methods and techniques for growing bacterial cells, inserting isolated DNA molecules into the host cell, and isolating, cloning and sequencing isolated nucleic acid molecules etc. are examples of such techniques and methods. These methods are described in many standard literature sources: Davis et al., Basic Methods In Molecular Biology (1986); J. H. Miller, Experiments in Molecular Genetics, Cold Spring Harbor Laboratory Press, Cold Spring Harbor, N.Y. (1972); J. H. Miller, A Short Course in Bacterial Genetics, Cold Spring Harbor Laboratory Press, Cold Spring Harbor, N.Y. (1992); M. Singer and P. Berg, Genes & Genomes, University Science Books, Mill Valley, Calif. (1991); J. Sambrook, E. F. Fritsch and T. Maniatis, Molecular Cloning: A Laboratory Manual, 2nd ed., Cold Spring Harbor Laboratory Press, Cold Spring Harbor, N.Y. (1989); P. B. Kaufmann et al., Handbook of Molecular and Cellular Methods in Biology and Medicine, CRC Press, Boca Raton, Fla. (1995); Methods in Plant Molecular Biology and Biotechnology, B. R. Glick and J. E. Thompson, eds., CRC Press, Boca Raton, Fla. (1993); and P. F. Smith-Keary, Molecular Genetics of *Escherichia coli*, The Guilford Press, New York, N.Y. (1989).

All nucleic acid molecules of the present invention are preferably in the form of an isolated nucleic acid molecule. An "isolated" nucleic acid molecule is separated from other nucleic acid molecules which are present in the natural source of the nucleic acid, and may additionally be substantially free of other cellular material or culture medium if it is prepared by recombinant techniques, or free of chemical precursors or other chemicals if it is chemically synthesized.

The invention additionally includes the nucleic acid molecules complementary to the specifically described nucleotide sequences, or a section thereof.

The promoters and/or expression units of the invention can for example be used particularly advantageously in improved methods for the preparation of biosynthetic products by fermentation as described hereinafter.

The promoters and/or expression units of the invention have in particular the advantage that they are induced in microorganisms by stress. It is possible by suitable control of the fermentation process to control this stress induction specifically for an increase in the transcription/expression rate of desired genes. In the production of L-lysine in particular, this stress phase is reached very early, so that in this case an increased transcription/expression rate of desired genes can be achieved very early.

The nucleic acids of the invention having promoter activity can be used to alter, i.e. to increase or reduce, or to cause the transcription rate of genes in microorganisms compared with the wild type.

The expression units of the invention can be used to alter, i.e. to increase or reduce, or to cause the expression rate of genes in microorganisms compared with the wild type.

The nucleic acids of the invention having promoter activity and the expression units of the invention can also serve to regulate and enhance the production of various biosynthetic products such as, for example, fine chemicals, proteins, in particular amino acids, microorganisms, in particular in *Corynebacterium* species.

The invention therefore relates to a method for altering or causing the transcription rate of genes in microorganisms compared with the wild type by
 a) altering the specific promoter activity in the microorganism of endogenous nucleic acids of the invention having promoter activity, which regulate the transcription of endogenous genes, compared with the wild type or
 b) regulating transcription of genes in the microorganism by nucleic acids of the invention having promoter activity or by nucleic acids with altered specific promoter activity as set forth in embodiment a), where the genes are heterologous in relation to the nucleic acids having promoter activity.

According to embodiment a), the alteration or causing of the transcription rate of genes in the microorganism compared with the wild type can take place by altering, i.e. increasing or reducing, the specific promoter activity in the microorganism. This can take place for example by targeted mutation of the nucleic acid sequence of the invention having promoter activity, i.e. by targeted substitution, deletion or insertion of nucleotides. An increased or reduced promoter activity can be achieved by replacing nucleotides in the RNA polymerase holoenzyme binding sites (known to the skilled worker also as −10 region and −35 region). Additionally by reducing or enlarging the distance of the described RNA polymerase holoenzyme binding sites from one another by deleting nucleotides or inserting nucleotides. Additionally by putting binding sites (also known to the skilled worker as operators) for regulatory proteins (known to the skilled worker as repressors and activators) in the spatial vicinity of the binding sites of the RNA polymerase holoenzyme so that, after binding to a promoter sequence, these regulators diminish or enhance the binding and transcription activity of the RNA polymerase holoenzyme, or else place it under a new regulatory influence.

The nucleic acid sequence SEQ. ID. NO. 44 preferably represents the ribosome binding site of the expression units of the invention, and the sequences SEQ. ID. NOs. 42 or 43 represent the −10 region of the expression units of the invention. Alterations in the nucleic acid sequence in these regions lead to an alteration in the specific expression activity.

The invention therefore relates to the use of the nucleic acid sequence SEQ. ID. NO. 44 as ribosome binding site in expression units which enable genes to be expressed in bacteria of the genus *Corynebacterium* or *Brevibacterium*.

The invention further relates to the use of the nucleic acid sequences SEQ. ID. NOs. 42 or 43 as −10 region in expression units which enable genes to be expressed in bacteria of the genus *Corynebacterium* or *Brevibacterium*.

The invention relates in particular to an expression unit which enables genes to be expressed in bacteria of the genus *Corynebacterium* or *Brevibacterium*, comprising the nucleic acid sequence SEQ. ID. NO. 44. In this case, the nucleic acid sequence SEQ. ID. NO. 44 is preferably used as ribosome binding site.

The invention further relates to an expression unit which enables genes to be expressed in bacteria of the genus *Corynebacterium* or *Brevibacterium*, comprising at least one of the nucleic acid sequences SEQ. ID. NOs. 42 or 43. In this case, one of the nucleic acid sequences SEQ. ID. NOs. 42 or 43 is preferably used as −10 region.

In relation to the "specific promoter activity", an increase or reduction compared with the wild type means an increase or reduction in the specific activity compared with the nucleic acid of the invention having promoter activity of the wild type, i.e. for example compared with SEQ. ID. NO. 1.

According to embodiment b), the alteration or causing of the transcription rate of genes in microorganisms compared with the wild type can take place by regulating the transcription of genes in the microorganism by nucleic acids of the invention having promoter activity or by nucleic acids with altered specific promoter activity according to embodiment a), where the genes are heterologous in relation to the nucleic acids having promoter activity.

This is preferably achieved by
- b1) introducing one or more nucleic acids of the invention having promoter activity, where appropriate with altered specific promoter activity, into the genome of the microorganism so that transcription of one or more endogenous genes takes place under the control of the introduced nucleic acid having promoter activity, where appropriate with altered specific promoter activity, or
- b2) introducing one or more genes into the genome of the microorganism so that transcription of one or more of the introduced genes takes place under the control of the endogenous nucleic acids of the invention having promoter activity, where appropriate with altered specific promoter activity, or
- b3) introducing one or more nucleic acid constructs comprising a nucleic acid of the invention having promoter activity, where appropriate with altered specific promoter activity, and functionally linked one or more nucleic acids to be transcribed, into the microorganism.

It is thus possible to alter, i.e. to increase or to reduce, the transcription rate of an endogenous gene of the wild type by according to embodiment b1), introducing one or more nucleic acids of the invention having promoter activity, where appropriate with altered specific promoter activity, into the genome of the microorganism so that transcription of one or more endogenous genes takes place under the control of the introduced nucleic acid having promoter activity, where appropriate with altered specific promoter activity, or according to embodiment b2), introducing one or more endogenous genes into the genome of the microorganism so that transcription of one or more of the introduced endogenous genes takes place under the control of the endogenous nucleic acids of the invention having promoter activity, where appropriate with altered specific promoter activity, or according to embodiment b3), introducing one or more nucleic acid constructs comprising a nucleic acid of the invention having promoter activity, where appropriate with altered specific promoter activity, and functionally linked one or more endogenous nucleic acids to be transcribed, into the microorganism.

It is thus further possible to cause the transcription rate of an exogenous gene compared with the wild type by according to embodiment b2), introducing one or more endogenous genes into the genome of the microorganism so that transcription of one or more of the introduced exogenous genes takes place under the control of the endogenous nucleic acids of the invention having promoter activity, where appropriate with altered specific promoter activity, or according to embodiment b3), introducing one or more nucleic acid constructs comprising a nucleic acid of the invention having promoter activity, where appropriate with altered specific promoter activity, and functionally linked one or more exogenous nucleic acids to be transcribed, into the microorganism.

The insertion of genes according to embodiment b2) can moreover take place by integrating a gene into coding regions or noncoding regions. Insertion preferably takes place into noncoding regions.

Insertion of nucleic acid constructs according to embodiment b3) may moreover take place chromosomally or extrachromosomally. There is preferably chromosomal insertion of the nucleic acid constructs. A "chromosomal" integration is the insertion of an exogenous DNA fragment into the chromosome of a host cell. This term is also used for homologous recombination between an exogenous DNA fragment and the appropriate region on the chromosome of the host cell.

In embodiment b) there is preferably also use of nucleic acids of the invention with altered specific promoter activity in accordance with embodiment a). In embodiment b), as described in embodiment a), these may be present or be prepared in the microorganism, or be introduced in isolated form into the microorganism.

"Endogenous" means genetic information, such as, for example, genes, which is already present in the wild-type genome.

"Exogenous" means genetic information, such as, for example, genes, which is not present in the wild-type genome.

The term "genes" in relation to regulation of transcription by the nucleic acids of the invention having promoter activity preferably means nucleic acids which comprise a region to be transcribed, i.e. for example a region which regulates the translation, and a coding region and, where appropriate, further regulatory elements such as, for example, a terminator.

The term "genes" in relation to the regulation, described hereinafter, of expression by the expression units of the invention preferably means nucleic acids which comprise a coding region and, where appropriate, further regulatory elements such as, for example, a terminator.

A "coding region" means a nucleic acid sequence which encodes a protein.

"Heterologous" in relation to nucleic acids having promoter activity and genes means that the genes used are not in the wild type transcribed under the regulation of the nucleic acids of the invention having promoter activity, but that a new functional linkage which does not occur in the wild type is produced, and the functional combination of nucleic acid of the invention having promoter activity and specific gene does not occur in the wild type.

"Heterologous" in relation to expression units and genes means that the genes used are not in the wild type expressed under the regulation of the expression units of the invention having promoter activity, but that a new functional linkage which does not occur in the wild type is produced, and the functional combination of expression unit of the invention and specific gene does not occur in the wild type.

The invention further relates in a preferred embodiment to a method for increasing or causing the transcription rate of genes in microorganisms compared with the wild type by
- ah) increasing the specific promoter activity in the microorganism of endogenous nucleic acids of the invention having promoter activity, which regulate the transcription of endogenous genes, compared with the wild type, or
- bh) regulating the transcription of genes in the microorganism by nucleic acids of the invention having promoter activity or by nucleic acids with increased specific promoter activity as set forth in embodiment a), where the genes are heterologous in relation to the nucleic acids having promoter activity.

The regulation of the transcription of genes in the microorganism by nucleic acids of the invention having promoter activity or by nucleic acids of the invention with increased specific promoter activity according to embodiment ah) is preferably achieved by bh1) introducing one or more nucleic acids of the invention having promoter activity, where appropriate with increased specific promoter activity, into the genome of the microorganism so that transcription of one or more endogenous genes takes place under the control of the introduced nucleic acid of the invention having promoter activity, where appropriate with increased specific promoter activity, or bh2) introducing one or more genes into the genome of the microorganism so that transcription of one or more of the introduced genes takes place under the control of the endogenous nucleic acids of the invention having promoter activity, where appropriate with increased specific promoter activity, or bh3) introducing one or more nucleic acid constructs comprising a nucleic acid of the invention having promoter activity, where appropriate with increased specific promoter activity, and functionally linked one or more nucleic acids to be transcribed, into the microorganism.

The invention further relates in a preferred embodiment to a method for reducing the transcription rate of genes in microorganisms compared with the wild type by ar) reducing the specific promoter activity in the microorganism of endogenous nucleic acids of the invention having promoter activity, which regulate the transcription of the endogenous genes, compared with the wild type, or br) introducing nucleic acids with reduced specific promoter activity as set forth in embodiment a) into the genome of the microorganism so that transcription of endogenous genes takes place under the control of the introduced nucleic acid with reduced promoter activity.

The invention further relates to a method for altering or causing the expression rate of a gene in microorganisms compared with the wild type by c) altering the specific expression activity in the microorganism of endogenous expression units of the invention, which regulate the expression of the endogenous genes, compared with the wild type, or d) regulating the expression of genes in the microorganism by expression units of the invention or by expression units of the invention with altered specific expression activity as set forth in embodiment c), where the genes are heterologous in relation to the expression units.

According to embodiment c), the alteration or causing of the expression rate of genes in microorganisms compared with the wild type can take place by altering, i.e. increasing or reducing, the specific expression activity in the microorganism. This can take place for example by targeted mutation of the nucleic acid sequence of the invention having promoter activity, i.e. by targeted substitution, deletion or insertion of nucleotides. For example, extending the distance between Shine-Dalgarno sequence and the translation start codon usually leads to a change, a diminution or else an enhancement of the specific expression activity. An alteration of the specific expression activity can also be achieved by either shortening or extending the distance of the sequence of the Shine-Dalgarno region (ribosome binding site) from the translation start codon through deletions or insertions of nucleotides. But also by altering the sequence of the Shine-Dalgarno region in such a way that the homology to complementary 3' side 16S rRNA is either enhanced or else diminished.

In relation to the "specific expression activity", an increase or reduction compared with the wild type means an increase or reduction of the specific activity compared with the expression unit of the invention of the wild type, i.e. for example compared with SEQ. ID. NO. 2.

According to embodiment d), the alteration or causing of the expression rate of genes in microorganisms compared with the wild type can take place by regulating the expression of genes in the microorganism by expression units of the invention or by expression units of the invention with altered specific expression activity as set forth in embodiment c), where the genes are heterologous in relation to the expression units.

This is preferably achieved by d1) introducing one or more expression units of the invention, where appropriate with altered specific expression activity, into the genome of the microorganism so that expression of one or more endogenous genes takes place under the control of the introduced expression units, or d2) introducing one or more genes into the genome of the microorganism so that expression of one or more of the introduced genes takes place under the control of the endogenous expression units of the invention, where appropriate with altered specific expression activity, or d3) introducing one or more nucleic acid constructs comprising an expression unit of the invention, where appropriate with altered specific expression activity, and functionally linked one or more nucleic acids to be expressed, into the microorganism.

It is thus possible to alter, i.e. to increase or to reduce, the expression rate of an endogenous gene of the wild type by according to embodiment d1) introducing one or more expression units of the invention, where appropriate with altered specific expression activity, into the genome of the microorganism so that expression of one or more endogenous genes takes place under the control of the introduced expression units, or according to embodiment d2) introducing one or more genes into the genome of the microorganism so that expression of one or more of the introduced genes takes place under the control of the endogenous expression units of the invention, where appropriate with altered specific expression activity, or according to embodiment d3) introducing one or more nucleic acid constructs comprising an expression unit of the invention, where appropriate with altered specific expression activity, and functionally linked one or more nucleic acids to be expressed, into the microorganism.

It is thus further possible to cause the expression rate of an endogenous gene compared with the wild type by according to embodiment d2) introducing one or more exogenous genes into the genome of the microorganism so that expression of one or more of the introduced genes takes place under the control of the endogenous expression units of the invention, where appropriate with altered specific expression activity, or according to embodiment d3) introducing one or more nucleic acid constructs comprising an expression unit of the invention, where appropriate with altered specific expression activity, and functionally linked one or more exogenous nucleic acids to be expressed, into the microorganism.

The insertion of genes according to embodiment d2) can moreover take place by integrating a gene into coding regions or noncoding regions. Insertion preferably takes place into noncoding regions.

Insertion of nucleic acid constructs according to embodiment d3) may moreover take place chromosomally or extrachromosomally. There is preferably chromosomal insertion of the nucleic acid constructs.

The nucleic acid constructs are also referred to hereinafter as expression cassettes.

In embodiment d) there is preferably also use of expression units of the invention with altered specific expression activity in accordance with embodiment c). In embodiment d), as described in embodiment c), these may be present or be prepared in the microorganism, or be introduced in isolated form into the microorganism.

The invention further relates in a preferred embodiment to a method for increasing or causing the expression rate of a gene in microorganisms compared with the wild type by ch) increasing the specific expression activity in the microorganism of endogenous expression units of the invention, which regulate the expression of the endogenous genes, compared with the wild type, or dh) regulating the expression of genes in the microorganism by expression units of the invention or by expression units with increased specific expression activity as set forth in embodiment a), where the genes are heterologous in relation to the expression units.

The regulation of the expression of genes in the microorganism by expression units of the invention or by expression units with increased specific expression activity as set forth in embodiment c) is preferably achieved by

- dh1) introducing one or more expression units of the invention, where appropriate with increased specific expression activity, into the genome of the microorganism so that expression of one or more endogenous genes takes place under the control of the introduced expression units, where appropriate with increased specific expression activity, or
- dh2) introducing one or more genes into the genome of the microorganism so that expression of one or more of the introduced genes takes place under the control of the endogenous expression units of the invention, where appropriate with increased specific expression activity, or
- dh3) introducing one or more nucleic acid constructs comprising an expression unit of the invention, where appropriate with increased specific expression activity, and functionally linked one or more nucleic acids to be expressed, into the microorganism.

The invention further relates to a method for reducing the expression rate of genes in microorganisms compared with the wild type by cr) reducing the specific expression activity in the microorganism of endogenous expression units of the invention, which regulate the expression of the endogenous genes, compared with the wild type, or dr) introducing expression units with reduced specific expression activity as set forth in embodiment cr) into the genome of the microorganism so that expression of endogenous genes takes place under the control of the introduced expression units with reduced expression activity.

In a preferred embodiment of the methods of the invention described above for altering or causing the transcription rate and/or expression rate of genes in microorganisms, the genes are selected from the group of nucleic acids encoding a protein from the biosynthetic pathway of fine chemicals, where the genes may optionally comprise further regulatory elements.

In a particularly preferred embodiment of the methods of the invention described above for altering or causing the transcription rate and/or expression rate of genes in microorganisms, the genes are selected from the group of nucleic acids encoding a protein from the biosynthetic pathway of proteinogenic and non-proteinogenic amino acids, nucleic acids encoding a protein from the biosynthetic pathway of nucleotides and nucleosides, nucleic acids encoding a protein from the biosynthetic pathway of organic acids, nucleic acids encoding a protein from the biosynthetic pathway of lipids and fatty acids, nucleic acids encoding a protein from the biosynthetic pathway of diols, nucleic acids encoding a protein from the biosynthetic pathway of carbohydrates, nucleic acids encoding a protein from the biosynthetic pathway of aromatic compounds, nucleic acids encoding a protein from the biosynthetic pathway of vitamins, nucleic acids encoding a protein from the biosynthetic pathway of cofactors and nucleic acids encoding a protein from the biosynthetic pathway of enzymes, where the genes may optionally comprise further regulatory elements.

In a particularly preferred embodiment, the proteins from the biosynthetic pathway of amino acids are selected from the group of aspartate kinase, aspartate-semialdehyde dehydrogenase, diaminopimelate dehydrogenase, diaminopimelate decarboxylase, dihydrodipicolinate synthetase, dihydrodipicolinate reductase, glyceraldehyde-3-phosphate dehydrogenase, 3-phosphoglycerate kinase, pyruvate carboxylase, triosephosphate isomerase, transcriptional regulator LuxR, transcriptional regulator LysR1, transcriptional regulator LysR2, malate-quinone oxidoreductase, glucose-6-phosphate deydrogenase, 6-phosphogluconate dehydrogenase, transketolase, transaldolase, homoserine O-acetyltransferase, cystathionine gamma-synthase, cystathionine beta-lyase, serine hydroxymethyltransferase, O-acetylhomoserine sulfhydrylase, methylenetetrahydrofolate reductase, phosphoserine aminotransferase, phosphoserine phosphatase, serine acetyltransferase, homoserine dehydrogenase, homoserine kinase, threonine synthase, threonine exporter carrier, threonine dehydratase, pyruvate oxidase, lysine exporter, biotin ligase, cysteine synthase I, cysteine synthase II, coenzyme B12-dependent methionine synthase, coenzyme B12-independent methionine synthase activity, sulfate adenylyltransferase subunit 1 and 2, phosphoadenosine-phosphosulfate reductase, ferredoxin-sulfite reductase, ferredoxin NADP reductase, 3-phosphoglycerate dehydrogenase, RXA00655 regulator, RXN2910 regulator, arginyl-tRNA synthetase, phosphoenolpyruvate carboxylase, threonine efflux protein, serine hydroxymethyltransferase, fructose-1, 6-bisphosphatase, protein of sulfate reduction RXA077, protein of sulfate reduction RXA248, protein of sulfate reduction RXA247, protein OpcA, 1-phosphofructokinase and 6-phosphofructokinase.

Preferred proteins and nucleic acids encoding these proteins of the proteins described above from the biosynthetic pathway of amino acids are respectively protein sequences and nucleic acid sequences of microbial origin, preferably from bacteria of the genus *Corynebacterium* or *Brevibacterium*, preferably from coryneform bacteria, particularly preferably from *Corynebacterium glutamicum*.

Examples of particularly preferred protein sequences and the corresponding nucleic acid sequences encoding these proteins from the biosynthetic pathway of amino acids, the document referring thereto, and the designation thereof in the referring document are listed in Table 1:

TABLE 1

| Protein | Nucleic acid encoding protein | Referring document | SEQ. ID. NO. in referring document |
|---|---|---|---|
| Aspartate kinase | ask or lysC | EP1108790 | DNA: 281<br>Protein: 3781 |
| Aspartate-semialdehyde dehydrogenase | asd | EP1108790 | DNA: 331<br>Protein: 3831 |
| Dihydrodipicolinate synthetase | dapA | WO 0100843 | DNA: 55<br>Protein: 56 |
| Dihydrodipicolinate reductase | dapB | WO 0100843 | DNA: 35<br>Protein: 36 |
| meso-Diaminopimelate D-dehydrogenase | ddh | EP1108790 | DNA: 3494<br>Protein: 6944 |
| Diaminopicolinate decarboxytase | lysA | EP1108790 | DNA: 3451<br>Prot.: 6951 |
| Lysine exporter | lysE | EP1108790 | DNA: 3455<br>Prot.: 6955 |
| Arginyl-tRNA synthetase | argS | EP1108790 | DNA: 3450<br>Prot.: 6950 |
| Glucose-6-phosphate dehydrognease | zwf | WO 0100844 | DNA: 243<br>Prot.: 244 |
| Glyceraldehyde-3-phosphate dehydrogenase | gap | WO 0100844 | DNA: 187<br>Prot.: 188 |
| 3-Phosphoglycerate kinase | pgk | WO 0100844 | DNA: 69<br>Prot.: 70 |
| Pyruvate carboxylase | pycA | EP1108790 | DNA: 765<br>Prot.: 4265 |
| Triosephosphate isomerase | tpi | WO 0100844 | DNA: 61<br>Prot.: 62 |
| Biotin ligase | birA | EP1108790 | DNA: 786<br>Prot: 4286 |
| PEP carboxylase | pck | EP1108790 | DNA: 3470<br>Prot.: 6970 |
| Homoserine kinase | thrB | WO 0100843 | DNA: 173<br>Prot.: 174 |
| Threonine synthase | thrC | WO 0100843 | DNA: 175<br>Prot.: 176 |
| Threonine export carrier | thrE | WO 0251231 | DNA: 41<br>Prot.: 42 |
| Threonine efflux protein | RXA2390 | WO 0100843 | DNA: 7<br>Prot.: 8 |
| Threonine dehydratase | ilvA | EP 1108790 | DNA: 2328<br>Prot.: 5828 |
| Homoserine O-acetyltransferase | metA | EP 1108790 | DNA: 727<br>Prot.: 4227 |
| Cystathionine gamma-synthase | metB | EP 1108790 | DNA: 3491<br>Prot.: 6991 |
| Cystathionine beta-lyase | metC | EP 1108790 | DNA: 2535<br>Prot.: 6035 |
| Coenzyme B12-dependent methionine synthase, - | metH | EP 1108790 | DNA: 1663<br>Prot.: 5163 |
| O-Acetylhomoserine sulfhydrylase | metY | EP 1108790 | DNA: 726<br>Prot.: 4226 |
| Methylenetetrahydrofolate reductase | metF | EP 1108790 | DNA: 2379<br>Prot.: 5879 |
| D-3-Phosphoglycerate dehydrogenase | serA | EP 1108790 | DNA: 1415<br>Prot.: 4915 |
| Phosphoserine phosphatase 1 | serB | WO 0100843 | DNA: 153<br>Prot.: 154 |
| Phosphoserine phosphatase 2 | serB | EP 1108790 | DNA: 467<br>Prot.: 3967 |
| Phosphoserine phosphatase 3 | serB | EP 1108790 | DNA: 334<br>Prot.: 3834 |
| Phosphoserine aminotransferase | serC | WO 0100843 | DNA: 151<br>Prot.: 152 |
| Serine acetyltransferase | cysE | WO 0100843 | DNA: 243<br>Prot.: 244 |
| Cysteine synthase I | cysK | EP 1108790 | DNA: 2817<br>Prot.: 6317 |
| Cysteine synthase II | CysM | EP 1108790 | DNA: 2338<br>Prot.: 5838 |
| Homoserine dehydrogenase | hom | EP 1108790 | DNA: 3452<br>Prot.: 6952 |
| Coenzyme B12-independent methionine synthase | metE | WO 0100843 | DNA: 755<br>Prot.: 756 |
| Serine hydroxymethyltransferase | glyA | WO 0100843 | DNA: 143<br>Prot.: 144 |
| Protein in sulfate reduction | RXA247 | EP 1108790 | DNA: 3089<br>Prot.: 6589 |
| Protein in sulfate reduction | RXA248 | EP 1108790 | DNA: 3090<br>Prot.: 6590 |
| Sulfate adenylyltransferase subunit 1 | CysN | EP 1108790 | DNA: 3092<br>Prot.: 6592 |
| Sulfate adenylyl transferase subunit 2 | CysD | EP 1108790 | DNA: 3093<br>Prot.: 6593 |
| Phosphoadenosine-phosphosulfate reductase | CysH | WO 02729029 | DNA: 7<br>Prot.: 8 |
| Ferredoxin-sulfite reductase | RXA073 | WO 0100842 | DNA: 329<br>Prot.: 330 |
| Ferredoxin NADP-reductase | RXA076 | WO 0100843 | DNA: 79<br>Prot.: 80 |
| Transcriptional regulator LuxR | luxR | WO 0100842 | DNA: 297<br>Protein: 298 |
| Transcriptional regulator LysR1 | lysR1 | EP 1108790 | DNA: 676<br>Protein: 4176 |
| Transcriptional regulator LysR2 | lysR2 | EP 1108790 | DNA: 3228<br>Protein: 6728 |
| Transcriptional regulator LysR3 | lysRS | EP 1108790 | DNA: 2200<br>Protein: 5700 |
| Malate-quinone oxidoreductase | mqo | WO 0100844 | DNA: 569<br>Protein: 570 |
| Transketolase | RXA2739 | EP 1108790 | DNA: 1740<br>Prot: 5240 |
| Transaldolase | RXA2738 | WO 0100844 | DNA: 245<br>Prot: 246 |
| OpcA | opcA | WO 0100804 | DNA: 79<br>Prot: 80 |
| 1-Phosphofructo-kinase 1 | pfk1 | WO0100844 | DNA: 55<br>Protein: 56 |
| 1-Phosphofructo-kinase 2 | pfk2 | WO0100844 | DNA: 57<br>Protein: 58 |
| 6-Phosphofructo-kinase 1 | 6-pfk1 | EP 1108790 | DNA: 1383<br>Protein: 4883 |
| 6-Phosphofructo-kinase 2 | 6-pfk2 | DE 10112992 | DNA: 1<br>Protein: 2 |
| Fructose-1,6-bisphosphatase 1 | fbr1 | EP1108790 | DNA: 1136<br>Protein: 4636 |
| Pyruvate oxidase | poxB | WO 0100844 | DNA: 85<br>Protein: 86 |
| RXA00655 regulator | RXA655 | US2003162267.2 | DNA: 1<br>Prot.: 2 |
| RXN02910 regulator | RXN2910 | US2003162267.2 | DNA: 5<br>Prot.: 6 |
| 6-phosphoglucono-lactonase | RXA2735 | WO 0100844 | DNA: 1<br>Prot.: 2 |

A further example of a particularly preferred protein sequence and the corresponding nucleic acid sequence encoding this protein from the biosynthetic pathway of amino acids is the sequence of fructose-1,6-bisphosphatase 2, also called fbr2, (SEQ. ID. NO. 41) and the corresponding nucleic acid sequence encoding a fructose-1,6-bisphosphatase 2 (SEQ. ID. NO. 40).

A further example of a particularly preferred protein sequence and the corresponding nucleic acid sequence encoding this protein from the biosynthetic pathway of amino acids is the sequence of the protein in sulfate reduction, also called RXA077, (SEQ. ID. NO. 4) and the corresponding nucleic acid sequence encoding a protein in sulfate reduction (SEQ. ID. NO. 3).

Further particularly preferred protein sequences from the biosynthetic pathway of amino acids have in each case the amino acid sequence indicated in Table 1 for this protein, where the respective protein has, in at least one of the amino acid positions indicated in Table 2/column 2 for this amino acid sequence, a different proteinogenic amino acid than the respective amino acid indicated in Table 2/column 3 in the same line. In a further preferred embodiment, the proteins have, in at least one of the amino acid positions indicated in Table 2/column 2 for the amino acid sequence, the amino acid indicated in Table 2/column 4 in the same line. The proteins indicated in Table 2 are mutated proteins of the biosynthetic pathway of amino acids, which have particularly advantageous properties and are therefore particularly suitable for expressing the corresponding nucleic acids through the promoter of the invention and for producing amino acids. For example, the mutation T311I leads to the feedback inhibition of ask being switched off.

The corresponding nucleic acids which encode a mutated protein described above from Table 2 can be prepared by conventional methods.

A suitable starting point for preparing the nucleic acid sequences encoding a mutated protein is, for example, the genome of a *Corynebacterium glutamicum* strain which is obtainable from the American Type Culture Collection under the designation ATCC 13032, or the nucleic acid sequences referred to in Table 1. For the back-translation of the amino acid sequence of the mutated proteins into the nucleic acid sequences encoding these proteins, it is advantageous to use the codon usage of the organism into which the nucleic acid sequence is to be introduced or in which the nucleic acid sequence is present. For example, it is advantageous to use the codon usage of *Corynebacterium glutamicum* for *Corynebacterium glutamicum*. The codon usage of the particular organism can be ascertained in a manner known per se from databases or patent applications which describe at least one protein and one gene which encodes this protein from the desired organism.

The information in Table 2 is to be understood in the following way:

In column 1 "identification", an unambiguous designation for each sequence in relation to Table 1 is indicated.

In column 2 "AA-POS", the respective number refers to the amino acid position of the corresponding polypeptide sequence from Table 1. A "26" in the column "AA-POS" accordingly means amino acid position 26 of the correspondingly indicated polypeptide sequence. The numbering of the position starts at +1 at the N terminus.

In column 3 "AA wild type", the respective letter designates the amino acid—represented in one-letter code—at the position indicated in column 2 in the corresponding wild-type strain of the sequence from Table 1.

In column 4 "AA mutant", the respective letter designates the amino acid—represented in one-letter code—at the position indicated in column 2 in the corresponding mutant strain.

In column 5 "function", the physiological function of the corresponding polypeptide sequence is indicated.

For mutated protein with a particular function (column 5) and a particular initial amino acid sequence (Table 1), columns 2, 3 and 4 describe at least one mutation, and a plurality of mutations for some sequences. This plurality of mutations always refers to the closest initial amino acid sequence above in each case (Table 1). The term "at least one of the amino acid positions" of a particular amino acid sequence preferably means at least one of the mutations described for this amino acid sequence in columns 2, 3 and 4.

| One-letter code for proteinogenic amino acids: | |
|---|---|
| A | alanine |
| C | cysteine |
| D | aspartate |
| E | glutamate |
| F | phenylalanine |
| G | glycine |
| H | histidine |
| I | isoleucine |
| K | lysine |
| L | leucine |
| M | methionine |
| N | asparagine |
| P | proline |
| Q | glutamine |
| R | arginine |
| S | serine |
| T | threonine |
| V | valine |
| W | tryptophan |
| Y | tyrosine |

TABLE 2

| Column 1 Identification | Column 2 AA position | Column 3 AA wild type | Column 4 AA mutant | Column 5 Function |
|---|---|---|---|---|
| ask | 317 | S | A | aspartate kinase |
|  | 311 | T | I |  |
|  | 279 | A | T |  |
| asd | 66 | D | G | asparate-semialdehyde dehydrogenase |
|  | 234 | R | H |  |
|  | 272 | D | E |  |
|  | 285 | K | E |  |
|  | 20 | L | F |  |
| dapA | 2 | S | A | dihydrodipicolinate synthetase |
|  | 84 | K | N |  |
|  | 85 | L | V |  |
| dapB | 91 | D | A | dihydrodipicolinate reductase |
|  | 83 | D | N |  |
| ddh | 174 | D | E | meso-diaminopimelate D-dehydrogenase |
|  | 235 | F | L |  |
|  | 237 | S | A |  |
| lysA | 265 | A | D | diaminopicolinate decarboxylase |
|  | 320 | D | N |  |
|  | 332 | I | V |  |
| argS | 355 | G | D | arginyl-tRNA synthetase |
|  | 156 | A | S |  |
|  | 513 | V | A |  |
|  | 540 | H | R |  |
| zwt | 8 | S | T | glucose-6-phosphate dehydrogenase |
|  | 150 | T | A |  |
|  | 321 | G | S |  |
| gap | 264 | G | S | glyceraldehyde-3-phosphate dehydrogenase |
| pycA | 7 | S | L | pyruvate carboxylase |
|  | 153 | E | D |  |
|  | 182 | A | S |  |
|  | 206 | A | S |  |
|  | 227 | H | R |  |
|  | 455 | A | G |  |
|  | 458 | P | S |  |
|  | 639 | S | T |  |
|  | 1008 | R | H |  |
|  | 1059 | S | P |  |
|  | 1120 | D | E |  |
| pck | 162 | H | Y | PEP carboxylase |
|  | 241 | G | D |  |
|  | 829 | T | R |  |
| thrB | 103 | S | A | homoserine kinase |
|  | 190 | T | A |  |
|  | 133 | A | V |  |
|  | 138 | P | S |  |
| thrC | 69 | G | R | threonine synthase |
|  | 478 | T | I |  |

TABLE 2-continued

| Column 1 Identification | Column 2 AA position | Column 3 AA wild type | Column 4 AA mutant | Column 5 Function |
|---|---|---|---|---|
| RXA330 | 85 | I | M | threonine efflux protein |
|  | 161 | F | I |  |
|  | 195 | G | D |  |
| hom | 104 | V | I | homoserine dehydrogenase |
|  | 116 | T | I |  |
|  | 148 | G | A |  |
|  | 59 | V | A |  |
|  | 270 | T | S |  |
|  | 345 | R | P |  |
|  | 268 | K | N |  |
|  | 61 | D | H |  |
|  | 72 | E | Q |  |
| lysR1 | 80 | R | H | transcriptional regulator LysR1 |
| lysR3 | 142 | R | W | transcriptional regulator LysR3 |
|  | 179 | A | T |  |
| RXA2739 | 75 | N | D | transketolase |
|  | 329 | A | T |  |
|  | 332 | A | T |  |
|  | 556 | V | I |  |
| RXA2738 | 242 | K | M | transaldolase |
| opcA | 107 | Y | H | OpcA |
|  | 219 | K | N |  |
|  | 233 | P | S |  |
|  | 261 | Y | H |  |
|  | 312 | S | F |  |
|  | 65 | G | R | aspartate-1-decarboxylase |
|  | 33 | G | S | 6-phosphoglucono-lactonase |

In the methods of the invention described above for altering or causing the transcription rate and/or expression rate of genes in microorganisms, and the methods described hereinafter for producing genetically modified microorganisms, the genetically modified microorganisms described hereinafter and the methods described hereinafter for producing biosynthetic products, the introduction of the nucleic acids of the invention having promoter activity, of the expression units of the invention, of the genes described above and of the nucleic acid constructs or expression cassettes described above into the microorganism, in particular into coryneform bacteria, preferably takes place by the SacB method.

The SacB method is known to the skilled worker and described for example in Schäfer A, Tauch A, Jäger W, Kalinowski J, Thierbach G, Pühler A.; Small mobilizable multipurpose cloning vectors derived from the *Escherichia coli* plasmids pK18 and pK19: selection of defined deletions in the chromosome of *Corynebacterium glutamicum*, Gene. 1994 Jul. 22; 145(1):69-73 and Blomfield I C, Vaughn V, Rest R F, Eisenstein B I.; Allelic exchange in *Escherichia coli* using the *Bacillus subtilis* sacB gene and a temperature-sensitive pSC101 replicon; Mol. Microbiol. 1991 June; 5(6): 1447-57.

In a preferred embodiment of the methods of the invention described above, the alteration or causing of the transcription rate and/or expression rate of genes in microorganisms takes place by introducing nucleic acids of the invention having promoter activity or expression units of the invention into the microorganism.

In a further preferred embodiment of the methods of the invention described above, the alteration or causing of the transcription rate and/or expression rate of genes in microorganisms takes place by introducing the nucleic acid constructs or expression cassettes described above into the microorganism.

The invention therefore also relates to an expression cassette comprising at least one expression unit of the invention at least one further nucleic acid sequence to be expressed, i.e. a gene to be expressed and where appropriate further genetic control elements such as, for example, a terminator, where at least one expression unit and a further nucleic acid sequence to be expressed are functionally linked together, and the further nucleic acid sequence to be expressed is heterologous in relation to the expression unit.

The nucleic acid sequence to be expressed is preferably at least one nucleic acid encoding a protein from the biosynthesis pathway of fine chemicals.

The nucleic acid sequence to be expressed is particularly preferably selected from the group of nucleic acids encoding a protein from the biosynthetic pathway of proteinogenic and non-proteinogenic amino acids, nucleic acids encoding a protein from the biosynthetic pathway of nucleotides and nucleosides, nucleic acids encoding a protein from the biosynthetic pathway of organic acids, nucleic acids encoding a protein from the biosynthetic pathway of lipids and fatty acids, nucleic acids encoding a protein from the biosynthetic pathway of diols, nucleic acids encoding a protein from the biosynthetic pathway of carbohydrates, nucleic acids encoding a protein from the biosynthetic pathway of aromatic compounds, nucleic acids encoding a protein from the biosynthetic pathway of vitamins, nucleic acids encoding a protein from the biosynthetic pathway of cofactors and nucleic acids encoding a protein from the biosynthetic pathway of enzymes.

Preferred proteins from the biosynthetic pathway of amino acids are described above and examples thereof are described in Tables 1 and 2.

The physical location of the expression unit relative to the gene to be expressed in the expression cassettes of the invention is chosen so that the expression unit regulates the transcription and preferably also the translation of the gene to be expressed, and thus enables one or more proteins to be produced. "Enabling production" includes in this connection a constitutive increase in the production, diminution or blocking of production under specific conditions and/or increasing the production under specific conditions. The "conditions" comprise in this connection: (1) addition of a component to the culture medium, (2) removal of a component from the culture medium, (3) replacement of one component in the culture medium by a second component, (4) increasing the temperature of the culture medium, (5) reducing the temperature of the culture medium, and (6) regulating the atmospheric conditions such as, for example, the oxygen or nitrogen concentration in which the culture medium is kept.

The invention further relates to an expression vector comprising an expression cassette of the invention described above.

Vectors are well known to the skilled worker and can be found in "Cloning Vectors" (Pouwels P. H. et al., editors, Elsevier, Amsterdam-New York-Oxford, 1985). Apart from plasmids, vectors also mean all other vectors known to the skilled worker, such as, for example, phages, transposons, IS elements, phasmids, cosmids, and linear or circular DNA. These vectors may undergo autonomous replication in the host organism or chromosomal replication.

Suitable and particularly preferred plasmids are those which are replicated in coryneform bacteria. Numerous known plasmid vectors such as, for example, pZ1 (Menkel et al., Applied and Environmental Microbiology (1989) 64: 549-554), pEKEx1 (Eikmanns et al., Gene 102: 93-98

(1991)) or pHS2-1 (Sonnen et al., Gene 107: 69-74 (1991)) are based on the cryptic plasmids pHM1519, pBL1 or pGA1. Other plasmid vectors such as, for example, pCLiK5MCS, or those based on pCG4 (U.S. Pat. No. 4,489,160) or pNG2 (Serwold-Davis et al., FEMS Microbiology Letters 66, 119-124 (1990)) or pAG1 (U.S. Pat. No. 5,158,891), can be used in the same way.

Also suitable are those plasmid vectors with the aid of which the method of gene amplification by integration into the chromosome can be used, as described for example by Reinscheid et al. (Applied and Environmental Microbiology 60, 126-132 (1994)) for the duplication and amplification of the hom-thrB operon. In this method the complete gene is cloned into a plasmid vector which is able to replicate in a host (typically *E. coli*) but not in *C. glutamicum*. Examples of suitable vectors are pSUP301 (Simon et al., Bio/Technology 1, 784-791 (1983)), pK18mob or pK19mob (Schäfer et al., Gene 145, 69-73 (1994)), Bernard et al., Journal of Molecular Biology, 234: 534-541 (1993)), pEM1 (Schrumpf et al. 1991, Journal of Bacteriology 173: 4510-4516) or pBGS8 (Spratt et al., 1986, Gene 41: 337-342). The plasmid vector which comprises the gene to be amplified is subsequently transferred by transformation into the desired strain of *C. glutamicum*. Methods for transformation are described for example in Thierbach et al. (Applied Microbiology and Biotechnology 29, 356-362 (1988)), Dunican and Shivnan (Biotechnology 7, 1067-1070 (1989)) and Tauch et al. (FEMS Microbiological Letters 123, 343-347 (1994)).

The invention further relates to a genetically modified microorganism where the genetic modification leads to an alteration or causing of the transcription rate of at least one gene compared with the wild type, and is dependent on a) altering the specific promoter activity in the microorganism of at least one endogenous nucleic acid having promoter activity as set forth in claim 1, which regulates the transcription of at least one endogenous gene, or b) regulating the transcription of genes in the microorganism by nucleic acids having promoter activity as set forth in claim 1 or by nucleic acids having promoter activity as set forth in claim 1 with altered specific promoter activity as set forth in embodiment a), where the genes are heterologous in relation to the nucleic acids having promoter activity.

As described above for the methods, the regulation of the transcription of genes in the microorganism by nucleic acids having promoter activity as set forth in claim 1 or by nucleic acids having promoter activity as set forth in claim 1 with altered specific promoter activity as set forth in embodiment a), is achieved by b1) introducing one or more nucleic acids having promoter activity as set forth in claim 1, where appropriate with altered specific promoter activity, into the genome of the microorganism so that transcription of one or more endogenous genes takes place under the control of the introduced nucleic acid having promoter activity as set forth in claim 1, where appropriate with altered specific promoter activity, or b2) introducing one or more genes into the genome of the microorganism so that transcription of one or more of the introduced genes takes place under the control of the endogenous nucleic acids having promoter activity as set forth in claim 1, where appropriate with altered specific promoter activity, or b3) introducing one or more nucleic acid constructs comprising a nucleic acid having promoter activity as set forth in claim 1, where appropriate with altered specific promoter activity, and functionally linked one or more nucleic acids to be transcribed, into the microorganism.

The invention further relates to a genetically modified microorganism having elevated or caused transcription rate of at least one gene compared with the wild type, where ah) the specific promoter activity in the microorganism of endogenous nucleic acids having promoter activity as set forth in claim 1, which regulate the transcription of endogenous genes, is increased compared with the wild type, or bh) the transcription of genes in the microorganism is regulated by nucleic acids having promoter activity as set forth in claim 1 or by nucleic acids having increased specific promoter activity as set forth in embodiment ah), where the genes are heterologous in relation to the nucleic acids having promoter activity.

As described above for the methods, the regulation of the transcription of genes in the microorganism by nucleic acids having promoter activity as set forth in claim 1 or by nucleic acids having promoter activity as set forth in claim 1 with increased specific promoter activity as set forth in embodiment a), is achieved by bh1) introducing one or more nucleic acids having promoter activity as set forth in claim 1, where appropriate with increased specific promoter activity, into the genome of the microorganism so that transcription of one or more endogenous genes takes place under the control of the introduced nucleic acid having promoter activity, where appropriate with increased specific promoter activity, or bh2) introducing one or more genes into the genome of the microorganism so that transcription of one or more of the introduced genes takes place under the control of the endogenous nucleic acids having promoter activity as set forth in claim 1, where appropriate with increased specific promoter activity, or bh3) introducing one or more nucleic acid constructs comprising a nucleic acid having promoter activity as set forth in claim 1, where appropriate with increased specific promoter activity, and functionally linked one or more nucleic acids to be transcribed, into the microorganism.

The invention further relates to a genetically modified microorganism with reduced transcription rate of at least one gene compared with the wild type, where ar) the specific promoter activity in the microorganism of at least one endogenous nucleic acid having promoter activity as set forth in claim 1, which regulates the transcription of at least one endogenous gene, is reduced compared with the wild type, or br) one or more nucleic acids having reduced promoter activity as set forth in embodiment a) are introduced into the genome of the microorganism so that the transcription of at least one endogenous gene takes place under the control of the introduced nucleic acid having reduced promoter activity.

The invention further relates to a genetically modified microorganism, where the genetic modification leads to an alteration or causing of the expression rate of at least one gene compared with the wild type, and is dependent on c) altering the specific expression activity in the microorganism of at least one endogenous expression unit as set forth in claim 2 or 3, which regulates the expression of at least one endogenous gene, compared with the wild type or d) regulating the expression of genes in the microorganism by expression units as set forth in claim 2 or 3 or by expression units as set forth in claim 2 or 3 with altered specific expression activity as set forth in embodiment a), where the genes are heterologous in relation to the expression units.

As described above for the methods, the regulation of the expression of genes in the microorganism by expression units as set forth in claim 2 or 3 or by expression units as set forth in claim 2 or 3 with altered specific expression activity as set forth in embodiment a) is achieved by d1) introducing one or more expression units as set forth in claim 2 or 3, where appropriate with altered specific expression activity, into the genome of the microorganism so that expression of one or more endogenous genes takes place under the control of the introduced expression units according to claim 2 or 3, where appropriate with altered specific expression activity, or d2) introducing one or more genes into the genome of the microorganism so that expression of one or more of the introduced genes takes place under the control of the endogenous expression units as set forth in claim 2 or 3, where appropriate with altered specific expression activity, or d3) introducing one or more nucleic acid constructs comprising an expression unit as set forth in claim 2 or 3, where appropriate with altered specific expression activity, and functionally linked one or more nucleic acids to be expressed, into the microorganism.

The invention further relates to a genetically modified microorganism with increased or caused expression rate of at least one gene compared with the wild type, where ch) the specific expression activity in the microorganism of at least one endogenous expression unit as set forth in claim 2 or 3, which regulates the expression of the endogenous genes, is increased compared with the wild type, or dh) the expression of genes in the microorganism is regulated by expression units as set forth in claim 2 or 3 or by expression units as set forth in claim 2 or 3 with increased specific expression activity as set forth in embodiment a), where the genes are heterologous in relation to the expression units.

As described above for the methods, the regulation of the expression of genes in the microorganism by expression units as set forth in claim 2 or 3 or by expression units as set forth in claim 2 or 3 with increased specific expression activity as set forth in embodiment a) is achieved by dh1) introducing one or more expression units as set forth in claim 2 or 3, where appropriate with increased specific expression activity, into the genome of the microorganism so that expression of one or more endogenous genes takes place under the control of the introduced expression units according to claim 2 or 3, where appropriate with increased specific expression activity, or dh2) introducing one or more genes into the genome of the microorganism so that expression of one or more of the introduced genes takes place under the control of the endogenous expression units as set forth in claim 2 or 3, where appropriate with increased specific expression activity, or dh3) introducing one or more nucleic acid constructs comprising an expression unit as set forth in claim 2 or 3, where appropriate with increased specific expression activity, and functionally linked one or more nucleic acids to be expressed, into the microorganism.

The invention further relates to a genetically modified microorganism with reduced expression rate of at least one gene compared with the wild type, where cr) the specific expression activity in the microorganism of at least one endogenous expression unit as set forth in claim 2 or 3, which regulates the expression of at least one endogenous gene, is reduced compared with the wild type, or dr) one or more expression units according to claim 2 or 3 with reduced expression activity are introduced into the genome of the microorganism so that expression of at least one endogenous gene takes place under the control of the introduced expression unit according to claim 2 or 3 with reduced expression activity.

The invention further relates to a genetically modified microorganism comprising an expression unit as set forth in claim 2 or 3 and functionally linked a gene to be expressed, where the gene is heterologous in relation to the expression unit.

This genetically modified microorganism particularly preferably comprises an expression cassette of the invention.

The present invention particularly preferably relates to genetically modified microorganisms, in particular coryneform bacteria, which comprise a vector, in particular shuttle vector or plasmid vector, which harbors at least one recombinant nucleic acid construct as defined according to the invention.

In a preferred embodiment of the genetically modified microorganisms, the genes described above are at least one nucleic acid encoding a protein from the biosynthetic pathway of fine chemicals.

In a particularly preferred embodiment of the genetically modified microorganisms, the genes described above are selected from the group of nucleic acids encoding a protein from the biosynthetic pathway of proteinogenic and non-proteinogenic amino acids, nucleic acids encoding a protein from the biosynthetic pathway of nucleotides and nucleosides, nucleic acids encoding a protein from the biosynthetic pathway of organic acids, nucleic acids encoding a protein from the biosynthetic pathway of lipids and fatty acids, nucleic acids encoding a protein from the biosynthetic pathway of diols, nucleic acids encoding a protein from the biosynthetic pathway of carbohydrates, nucleic acids encoding a protein from the biosynthetic pathway of aromatic compounds, nucleic acids encoding a protein from the biosynthetic pathway of vitamins, nucleic acids encoding a protein from the biosynthetic pathway of cofactors and nucleic acids encoding a protein from the biosynthetic pathway of enzymes, where the genes may optionally comprise further regulatory elements.

Preferred proteins from the biosynthetic pathway of amino acids are selected from the group of aspartate kinase, aspartate-semialdehyde dehydrogenase, diaminopimelate dehydrogenase, diaminopimelate decarboxylase, dihydrodipicolinate synthetase, dihydrodipicolinate reductase, glyceraldehyde-3-phosphate dehydrogenase, 3-phosphoglycerate kinase, pyruvate carboxylase, triosephosphate isomerase, transcriptional regulator LuxR, transcriptional regulator LysR1, transcriptional regulator LysR2, malate-quinone oxidoreductase, glucose-6-phosphate deydrogenase, 6-phosphogluconate dehydrogenase, transketolase, transaldolase, homoserine O-acetyltransferase, cystathionine gamma-synthase, cystathionine beta-lyase, serine hydroxymethyltransferase, O-acetylhomoserine sulfhydrylase, methylenetetrahydrofolate reductase, phosphoserine aminotransferase, phosphoserine phosphatase, serine acetyltransferase, homoserine dehydrogenase, homoserine kinase, threonine synthase, threonine exporter carrier, threonine dehydratase, pyruvate oxidase, lysine exporter, biotin ligase, cysteine synthase 1, cysteine synthase II, coenzyme B12-dependent methionine synthase, coenzyme B12-independent methionine synthase activity, sulfate adenylyltransferase subunit 1 and 2, phosphoadenosine-phosphosulfate reductase, ferredoxin-sulfite reductase, ferredoxin NADP reductase, 3-phosphoglycerate dehydrogenase, RXA00655 regulator, RXN2910 regulator, arginyl-tRNA synthetase, phosphoenolpyruvate carboxylase, threonine efflux protein, serine hydroxymethyltransferase, fructose-1,6-bisphosphatase, protein of sulfate reduction RXA077, protein of sulfate reduction RXA248, protein of sulfate reduction RXA247, protein OpcA, 1-phosphofructokinase and 6-phosphofructokinase.

Particularly preferred examples of the proteins and genes from the biosynthetic pathway of amino acids are described above in Table 1 and Table 2.

Preferred microorganisms or genetically modified microorganisms are bacteria, algae, fungi or yeasts.

Particularly preferred microorganisms are, in particular, coryneform bacteria. Preferred coryneform bacteria are bacteria of the genus *Corynebacterium*, in particular of the species *Corynebacterium glutamicum, Corynebacterium acetoglutamicum, Corynebacterium acetoacidophilum, Corynebacterium thermoaminogenes, Corynebacterium melassecola* and *Corynebacterium efficiens* or of the genus *Brevibacterium*, in particular of the species *Brevibacterium flavum, Brevibacterium lactofermentum* and *Brevibacterium divaricatum*.

Particularly preferred bacteria of the genera *Corynebacterium* and *Brevibacterium* are selected from the group of *Corynebacterium glutamicum* ATCC 13032, *Corynebacterium acetoglutamicum* ATCC 15806, *Corynebacterium acetoacidophilum* ATCC 13870, *Corynebacterium thermoaminogenes* FERM BP-1539, *Corynebacterium melassecola* ATCC 17965, *Corynebacterium efficiens* DSM 44547, *Corynebacterium efficiens* DSM 44548, *Corynebacterium efficiens* DSM 44549, *Brevibacterium flavum* ATCC 14067, *Brevibacterium lactofermentum* ATCC 13869, *Brevibacterium divaricatum* ATCC 14020, *Corynebacterium glutamicum* KFCC10065 and *Corynebacterium glutamicum* ATCC21608.

The abbreviation KFCC means the Korean Federation of Culture Collection, the abbreviation ATCC the American type strain culture collection and the abbreviation DSM the Deutsche Sammlung von Mikroorganismen.

Further particularly preferred bacteria of the genera *Corynebacterium* and *Brevibacterium* are listed in Table 3:

| Bacterium | | Deposition number | | | | | | | |
|---|---|---|---|---|---|---|---|---|---|
| Genus | species | ATCC | FERM | NRRL | CECT | NCIMB | CBS | NCTC | DSMZ |
| Brevibacterium | ammoniagenes | 21054 | | | | | | | |
| Brevibacterium | ammoniagenes | 19350 | | | | | | | |
| Brevibacterium | ammoniagenes | 19351 | | | | | | | |
| Brevibacterium | ammoniagenes | 19352 | | | | | | | |
| Brevibacterium | ammoniagenes | 19353 | | | | | | | |
| Brevibacterium | ammoniagenes | 19354 | | | | | | | |
| Brevibacterium | ammoniagenes | 19355 | | | | | | | |
| Brevibacterium | ammoniagenes | 19356 | | | | | | | |
| Brevibacterium | ammoniagenes | 21055 | | | | | | | |
| Brevibacterium | ammoniagenes | 21077 | | | | | | | |
| Brevibacterium | ammoniagenes | 21553 | | | | | | | |
| Brevibacterium | ammoniagenes | 21580 | | | | | | | |
| Brevibacterium | ammoniagenes | 39101 | | | | | | | |
| Brevibacterium | butanicum | 21196 | | | | | | | |
| Brevibacterium | divaricatum | 21792 | P928 | | | | | | |
| Brevibacterium | flavum | 21474 | | | | | | | |
| Brevibacterium | flavum | 21129 | | | | | | | |
| Brevibacterium | flavum | 21518 | | | | | | | |
| Brevibacterium | flavum | | | B11474 | | | | | |
| Brevibacterium | flavum | | | B11472 | | | | | |
| Brevibacterium | flavum | 21127 | | | | | | | |
| Brevibacterium | flavum | 21128 | | | | | | | |
| Brevibacterium | flavum | 21427 | | | | | | | |
| Brevibacterium | flavum | 21475 | | | | | | | |
| Brevibacterium | flavum | 21517 | | | | | | | |
| Brevibacterium | flavum | 21528 | | | | | | | |
| Brevibacterium | flavum | 21529 | | | | | | | |
| Brevibacterium | flavum | | | B11477 | | | | | |
| Brevibacterium | flavum | | | B11478 | | | | | |
| Brevibacterium | flavum | 21127 | | | | | | | |
| Brevibacterium | flavum | | | B11474 | | | | | |
| Brevibacterium | healii | 15527 | | | | | | | |
| Brevibacterium | ketoglutamicum | 21004 | | | | | | | |
| Brevibacterium | ketoglutamicum | 21089 | | | | | | | |
| Brevibacterium | ketosoreductum | 21914 | | | | | | | |
| Brevibacterium | lactofermentum | | | | | | | 70 | |
| Brevibacterium | lactofermentum | | | | | | | 74 | |
| Brevibacterium | lactofermentum | | | | | | | 77 | |
| Brevibacterium | lactofermentum | 21798 | | | | | | | |
| Brevibacterium | lactofermentum | 21799 | | | | | | | |
| Brevibacterium | lactofermentum | 21800 | | | | | | | |
| Brevibacterium | lactofermentum | 21801 | | | | | | | |
| Brevibacterium | lactofermentum | | | B11470 | | | | | |
| Brevibacterium | lactofermentum | | | B11471 | | | | | |
| Brevibacterium | lactofermentum | 21086 | | | | | | | |
| Brevibacterium | lactofermentum | 21420 | | | | | | | |
| Brevibacterium | lactofermentum | 21086 | | | | | | | |
| Brevibacterium | lactofermentum | 31269 | | | | | | | |
| Brevibacterium | linens | 9174 | | | | | | | |
| Brevibacterium | linens | 19391 | | | | | | | |
| Brevibacterium | linens | 8377 | | | | | | | |
| Brevibacterium | paraffinolyticum | | | | | 11160 | | | |

-continued

| Bacterium | | Deposition number | | | | | | | |
|---|---|---|---|---|---|---|---|---|---|
| Genus | species | ATCC | FERM | NRRL | CECT | NCIMB | CBS | NCTC | DSMZ |
| *Brevibacterium* | spec. | | | | | | 717.73 | | |
| *Brevibacterium* | spec. | | | | | | 717.73 | | |
| *Brevibacterium* | spec. | 14604 | | | | | | | |
| *Brevibacterium* | spec. | 21860 | | | | | | | |
| *Brevibacterium* | spec. | 21864 | | | | | | | |
| *Brevibacterium* | spec. | 21865 | | | | | | | |
| *Brevibacterium* | spec. | 21866 | | | | | | | |
| *Brevibacterium* | spec. | 19240 | | | | | | | |
| *Corynebacterium* | *acetoacidophilum* | 21476 | | | | | | | |
| *Corynebacterium* | *acetoacidophilum* | 13870 | | | | | | | |
| *Corynebacterium* | *acetoglutamicum* | | | B11473 | | | | | |
| *Corynebacterium* | *acetoglutamicum* | | | B11475 | | | | | |
| *Corynebacterium* | *acetoglutamicum* | 15806 | | | | | | | |
| *Corynebacterium* | *acetoglutamicum* | 21491 | | | | | | | |
| *Corynebacterium* | *acetoglutamicum* | 31270 | | | | | | | |
| *Corynebacterium* | *acetophilum* | | | B3671 | | | | | |
| *Corynebacterium* | *ammoniagenes* | 6872 | | | | | | 2399 | |
| *Corynebacterium* | *ammoniagenes* | 15511 | | | | | | | |
| *Corynebacterium* | *fujiokense* | 21496 | | | | | | | |
| *Corynebacterium* | *glutamicum* | 14067 | | | | | | | |
| *Corynebacterium* | *glutamicum* | 39137 | | | | | | | |
| *Corynebacterium* | *glutamicum* | 21254 | | | | | | | |
| *Corynebacterium* | *glutamicum* | 21255 | | | | | | | |
| *Corynebacterium* | *glutamicum* | 31830 | | | | | | | |
| *Corynebacterium* | *glutamicum* | 13032 | | | | | | | |
| *Corynebacterium* | *glutamicum* | 14305 | | | | | | | |
| *Corynebacterium* | *glutamicum* | 15455 | | | | | | | |
| *Corynebacterium* | *glutamicum* | 13058 | | | | | | | |
| *Corynebacterium* | *glutamicum* | 13059 | | | | | | | |
| *Corynebacterium* | *glutamicum* | 13060 | | | | | | | |
| *Corynebacterium* | *glutamicum* | 21492 | | | | | | | |
| *Corynebacterium* | *glutamicum* | 21513 | | | | | | | |
| *Corynebacterium* | *glutamicum* | 21526 | | | | | | | |
| *Corynebacterium* | *glutamicum* | 21543 | | | | | | | |
| *Corynebacterium* | *glutamicum* | 13287 | | | | | | | |
| *Corynebacterium* | *glutamicum* | 21851 | | | | | | | |
| *Corynebacterium* | *glutamicum* | 21253 | | | | | | | |
| *Corynebacterium* | *glutamicum* | 21514 | | | | | | | |
| *Corynebacterium* | *glutamicum* | 21516 | | | | | | | |
| *Corynebacterium* | *glutamicum* | 21299 | | | | | | | |
| *Corynebacterium* | *glutamicum* | 21300 | | | | | | | |
| *Corynebacterium* | *glutamicum* | 39684 | | | | | | | |
| *Corynebacterium* | *glutamicum* | 21488 | | | | | | | |
| *Corynebacterium* | *glutamicum* | 21649 | | | | | | | |
| *Corynebacterium* | *glutamicum* | 21650 | | | | | | | |
| *Corynebacterium* | *glutamicum* | 19223 | | | | | | | |
| *Corynebacterium* | *glutamicum* | 13869 | | | | | | | |
| *Corynebacterium* | *glutamicum* | 21157 | | | | | | | |
| *Corynebacterium* | *glutamicum* | 21158 | | | | | | | |
| *Corynebacterium* | *glutamicum* | 21159 | | | | | | | |
| *Corynebacterium* | *glutamicum* | 21355 | | | | | | | |
| *Corynebacterium* | *glutamicum* | 31808 | | | | | | | |
| *Corynebacterium* | *glutamicum* | 21674 | | | | | | | |
| *Corynebacterium* | *glutamicum* | 21562 | | | | | | | |
| *Corynebacterium* | *glutamicum* | 21563 | | | | | | | |
| *Corynebacterium* | *glutamicum* | 21564 | | | | | | | |
| *Corynebacterium* | *glutamicum* | 21565 | | | | | | | |
| *Corynebacterium* | *glutamicum* | 21566 | | | | | | | |
| *Corynebacterium* | *glutamicum* | 21567 | | | | | | | |
| *Corynebacterium* | *glutamicum* | 21568 | | | | | | | |
| *Corynebacterium* | *glutamicum* | 21569 | | | | | | | |
| *Corynebacterium* | *glutamicum* | 21570 | | | | | | | |
| *Corynebacterium* | *glutamicum* | 21571 | | | | | | | |
| *Corynebacterium* | *glutamicum* | 21572 | | | | | | | |
| *Corynebacterium* | *glutamicum* | 21573 | | | | | | | |
| *Corynebacterium* | *glutamicum* | 21579 | | | | | | | |
| *Corynebacterium* | *glutamicum* | 19049 | | | | | | | |
| *Corynebacterium* | *glutamicum* | 19050 | | | | | | | |
| *Corynebacterium* | *glutamicum* | 19051 | | | | | | | |
| *Corynebacterium* | *glutamicum* | 19052 | | | | | | | |
| *Corynebacterium* | *glutamicum* | 19053 | | | | | | | |
| *Corynebacterium* | *glutamicum* | 19054 | | | | | | | |
| *Corynebacterium* | *glutamicum* | 19055 | | | | | | | |
| *Corynebacterium* | *glutamicum* | 19056 | | | | | | | |
| *Corynebacterium* | *glutamicum* | 19057 | | | | | | | |
| *Corynebacterium* | *glutamicum* | 19058 | | | | | | | |

-continued

| Bacterium | | Deposition number | | | | | | | |
|---|---|---|---|---|---|---|---|---|---|
| Genus | species | ATCC | FERM | NRRL | CECT | NCIMB | CBS | NCTC | DSMZ |
| Corynebacterium | glutamicum | 19059 | | | | | | | |
| Corynebacterium | glutamicum | 19060 | | | | | | | |
| Corynebacterium | glutamicum | 19185 | | | | | | | |
| Corynebacterium | glutamicum | 13286 | | | | | | | |
| Corynebacterium | glutamicum | 21515 | | | | | | | |
| Corynebacterium | glutamicum | 21527 | | | | | | | |
| Corynebacterium | glutamicum | 21544 | | | | | | | |
| Corynebacterium | glutamicum | 21492 | | | | | | | |
| Corynebacterium | glutamicum | | | B8183 | | | | | |
| Corynebacterium | glutamicum | | | B8182 | | | | | |
| Corynebacterium | glutamicum | | | B12416 | | | | | |
| Corynebacterium | glutamicum | | | B12417 | | | | | |
| Corynebacterium | glutamicum | | | B12418 | | | | | |
| Corynebacterium | glutamicum | | | B11476 | | | | | |
| Corynebacterium | glutamicum | 21608 | | | | | | | |
| Corynebacterium | lilium | | P973 | | | | | | |
| Corynebacterium | nitrilophilus | 21419 | | | | 11594 | | | |
| Corynebacterium | spec. | | P4445 | | | | | | |
| Corynebacterium | spec. | | P4446 | | | | | | |
| Corynebacterium | spec. | 31088 | | | | | | | |
| Corynebacterium | spec. | 31089 | | | | | | | |
| Corynebacterium | spec. | 31090 | | | | | | | |
| Corynebacterium | spec. | 31090 | | | | | | | |
| Corynebacterium | spec. | 31090 | | | | | | | |
| Corynebacterium | spec. | 15954 | | | | | | | 20145 |
| Corynebacterium | spec. | 21857 | | | | | | | |
| Corynebacterium | spec. | 21862 | | | | | | | |
| Corynebacterium | spec. | 21863 | | | | | | | |

The abbreviations have the following meaning:
ATCC: American Type Culture Collection, Rockville, MD, USA
FERM: Fermentation Research Institute, Chiba, Japan
NRRL: ARS Culture Collection, Northern Regional Research Laboratory, Peoria, IL, USA
CECT: Coleccion Espanola de Cultivos Tipo, Valencia, Spain
NCIMB: National Collection of Industrial and Marine Bacteria Ltd., Aberdeen, UK
CBS: Centraalbureau voor Schimmelcultures, Baarn, NL
NCTC: National Collection of Type Cultures, London, UK
DSMZ: Deutsche Sammlung von Mikroorganismen und Zellkulturen, Braunschweig, Germany Through the nucleic acids of the invention having promoter activity and the expression units of the invention it is possible with the aid of the methods of the invention described above to regulate the metabolic pathways in the genetically modified microorganisms of the invention described above to specific biosynthetic products.

For this purpose, for example, metabolic pathways which lead to a specific biosynthetic product are enhanced by causing or increasing the transcription rate or expression rate of genes of this biosynthetic pathway in which the increased quantity of protein leads to an increased total activity of these proteins of the desired biosynthetic pathway and thus to an enhanced metabolic flux toward the desired biosynthetic product.

In addition, metabolic pathways which diverge from a specific biosynthetic product can be diminished by reducing the transcription rate or expression rate of genes of this divergent biosynthetic pathway in which the reduced quantity of protein leads to a reduced total activity of these proteins of the unwanted biosynthetic pathway and thus additionally to an enhanced metabolic flux toward the desired biosynthetic product.

The genetically modified microorganisms of the invention are able for example to produce biosynthetic products from glucose, sucrose, lactose, fructose, maltose, molasses, starch, cellulose or from glycerol and ethanol.

The invention therefore relates to a method for producing biosynthetic products by cultivating genetically modified microorganisms of the invention.

Depending on the desired biosynthetic product, the transcription rate or expression rate of various genes must be increased or reduced. Ordinarily, it is advantageous to alter the transcription rate or expression rate of a plurality of genes, i.e. to increase the transcription rate or expression rate of a combination of genes and/or to reduce the transcription rate or expression rate of a combination of genes.

In the genetically modified microorganisms of the invention, at least one altered, i.e. increased or reduced, transcription rate or expression rate of a gene is attributable to a nucleic acid of the invention having promoter activity or expression unit of the invention.

Further, additionally altered, i.e. additionally increased or additionally reduced, transcription rates or expression rates of further genes in the genetically modified microorganism may, but need not, derive from the nucleic acids of the invention having promoter activity or the expression units of the invention.

The invention therefore further relates to a method for producing biosynthetic products by cultivating genetically modified microorganisms of the invention.

Preferred biosynthetic products are fine chemicals.

The term "fine chemical" is known in the art and includes compounds which are produced by an organism and are used in various branches of industry such as, for example but not restricted to, the pharmaceutical industry, the agriculture, cosmetics, food and feed industries. These compounds include organic acids such as, for example, tartaric acid, itaconic acid and diaminopimelic acid, and proteinogenic and non-proteinogenic amino acids, purine bases and pyrimidine bases, nucleosides and nucleotides (as described for example in Kuninaka, A. (1996) Nucleotides and related compounds, pp. 561-612, in Biotechnology vol. 6, Rehm et al., editors, VCH: Weinheim and the references present therein), lipids, saturated and unsaturated fatty acids (e.g. arachidonic acid), diols (e.g. propanediol and butanediol), carbohydrates (e.g. hyaluronic acid and trehalose), aromatic compounds (e.g. aromatic amines, vanillin and indigo), vitamins and cofactors (as described in Ullmann's Encyclopedia of Industrial Chemistry, vol. A27, "Vitamins", pp. 443-613 (1996) VCH: Weinheim and the references present therein; and Ong, A. S., Niki, E. and Packer, L. (1995) "Nutrition, Lipids, Health and Disease" Proceedings of the UNESCO/Confederation of Scientific and Technological Associations in Malaysia and the Society for Free Radical Research—Asia, held on Sep. 1-3, 1994 in Penang, Malaysia, AOCS Press (1995)), enzymes and all other chemicals described by Gutcho (1983) in Chemicals by Fermentation, Noyes Data Corporation, ISBN: 0818805086 and the references indicated therein. The metabolism and the uses of certain fine chemicals are explained further below.

I. Amino Acid Metabolism and Uses

The amino acids comprise the fundamental structural units of all proteins and are thus essential for normal cell functions. The term "amino acid" is known in the art. The proteinogenic amino acids, of which there are 20 types, serve as structural units for proteins, in which they are linked together by peptide bonds, whereas the non-proteinogenic amino acids (of which hundreds are known) usually do not occur in proteins (see Ullmann's Encyclopedia of Industrial Chemistry, vol. A2, pp. 57-97 VCH: Weinheim (1985)). The amino acids may be in the D or L configuration, although L-amino acids are usually the only type found in naturally occurring proteins. Biosynthetic and degradation pathways of each of the 20 proteinogenic amino acids are well characterized both in prokaryotic and in eukaryotic cells (see, for example, Stryer, L. Biochemistry, 3rd edition, pp. 578-590 (1988)). The "essential" amino acids (histidine, isoleucine, leucine, lysine, methionine, phenylalanine, threonine, tryptophan and valine), so-called because they must, owing to the complexity of their biosynthesis, be taken in with the diet, are converted by simple biosynthetic pathways into the other 11 "nonessential" amino acids (alanine, arginine, asparagine, aspartate, cysteine, glutamate, glutamine, glycine, proline, serine and tyrosine). Higher animals have the ability to synthesize some of these amino acids, but the essential amino acids must be taken in with the food in order for normal protein synthesis to take place.

Apart from their function in protein biosynthesis, these amino acids are chemicals of interest per se, and it has been found that many have uses in various applications in the food, feed, chemicals, cosmetics, agriculture and pharmaceutical industries. Lysine is an important amino acid not only for human nutrition but also for monogastric species such as poultry and pigs. Glutamate is used most frequently as flavor additive (monosodium glutamate, MSG) and widely in the food industry, as well as aspartate, phenylalanine, glycine and cysteine. Glycine, L-methionine and tryptophan are all used in the pharmaceutical industry. Glutamine, valine, leucine, isoleucine, histidine, arginine, proline, serine and alanine are used in the pharmaceutical industry and the cosmetics industry. Threonine, tryptophan and D-/L-methionine are widely used feed additives (Leuchtenberger, W. (1996) Amino acids—technical production and use, pp. 466-502 in Rehm et al., (editors) Biotechnology vol. 6, chapter 14a, VCH: Weinheim). It has been found that these amino acids are additionally suitable as precursors for synthesizing synthetic amino acids and proteins such as N-acetylcysteine, S-carboxymethyl-L-cysteine, (S)-5-hydroxytryptophan and other substances described in Ullmann's Encyclopedia of Industrial Chemistry, vol. A2, pp. 57-97, VCH, Weinheim, 1985.

The biosynthesis of these natural amino acids in organisms able to produce them, for example bacteria, has been well characterized (for a review of bacterial amino acid biosynthesis and its regulation, see Umbarger, H. E. (1978) Ann. Rev. Biochem. 47: 533-606). Glutamate is synthesized by reductive amination of α-ketoglutarate, an intermediate in the citric acid cycle. Glutamine, proline and arginine are each generated successively from glutamate. Biosynthesis of serine takes place in a three-step method and starts with 3-phosphoglycerate (an intermediate of glycolysis) and yields this amino acid after oxidation, transamination and hydrolysis steps. Cysteine and glycine are each produced from serine, the former by condensation of homocysteine with serine, and the latter by transfer of the side-chain β-carbon atom to tetrahydrofolate in a reaction catalyzed by serine transhydroxymethylase. Phenylalanine and tyrosine are synthesized from the precursors of the glycolysis and pentose phosphate pathways, erythrose 4-phosphate and phosphenolpyruvate in a 9-step biosynthetic pathway which differs only in the last two steps after the synthesis of prephenate. Tryptophan is likewise produced from these two starting molecules, but its synthesis takes place in an 11-step pathway. Tyrosine can also be produced from phenylalanine in a reaction catalyzed by phenylalanine hydroxylase. Alanine, valine and leucine are each biosynthetic products of pyruvate, the final product of glycolysis. Aspartate is formed from oxalacetate, an intermediate of the citrate cycle. Asparagine, methionine, threonine and lysine are each produced by conversion of aspartate. Isoleucine is formed from threonine. Histidine is formed in a complex 9-step pathway from 5-phosphoribosyl 1-pyrophosphate, an activated sugar.

Amino acids whose quantity exceeds the protein biosynthesis requirement of the cell cannot be stored and are instead degraded, so that intermediates are provided for the main metabolic pathways of the cell (for a review, see Stryer, L., Biochemistry, 3rd edition, chapter 21 "Amino Acid Degradation and the Urea Cycle"; pp. 495-516 (1988)). Although the cell is able to convert unwanted amino acids into useful metabolic intermediates, amino acid production is costly in terms of the energy, the precursor molecules and the enzymes required for their synthesis. It is therefore not surprising that amino acid biosynthesis is regulated by feedback inhibition, where the presence of a particular amino acid slows down or entirely terminates its own production (for a review of the feedback mechanism in amino acid biosynthetic pathways, see Stryer, L., Biochemistry, 3rd edition, chapter 24, "Biosynthesis of Amino Acids and Heme", pp. 575-600 (1988)). The output of a particular amino acid is therefore restricted by the quantity of this amino acid in the cell.

II. Vitamins, Cofactors and Nutraceutical Metabolism, and Uses

Vitamins, cofactors and nutraceuticals comprise a further group of molecules. Higher animals have lost the ability to synthesize these and therefore need to take them in, although they are easily synthesized by other organisms such as bacteria. These molecules are either biologically active molecules per se or precursors of biologically active substances which serve as electron carriers or intermediates in a number of metabolic pathways. These compounds have, besides their nutritional value, also a significant industrial value as coloring agents, antioxidants and catalysts or other processing aids. (For a review of the structure, activity and industrial applications of these compounds, see, for example, Ullmann's Encyclopedia of Industrial Chemistry, "Vitamins", vol. A27, pp. 443-613, VCH: Weinheim, 1996). The term "vitamin" is known in the art and includes nutrients which are required by an organism for normal functioning, but cannot be synthesized by this organism itself. The group of vitamins may include cofactors and nutraceutical compounds. The term "cofactor" includes non-protein compounds which are necessary for the occurrence of normal enzymic activity. These compounds may be organic or inorganic; the cofactor molecules of the invention are preferably organic. The term "nutraceutical" includes food additives which promote health in plants and animals, especially in humans. Examples of such molecules are vitamins, antioxidants and likewise certain lipids (e.g. polyunsaturated fatty acids).

Biosynthesis of these molecules in organisms able to produce them, such as bacteria, has been characterized in detail (Ullmann's Encyclopedia of Industrial Chemistry, "Vitamins", vol. A27, pp. 443-613, VCH: Weinheim, 1996, Michal, G. (1999) Biochemical Pathways An Atlas of Biochemistry and Molecular Biology, John Wiley & Sons; Ong, A. S., Niki, E. and Packer, L. (1995) "Nutrition, Lipids, Health and Disease" Proceedings of the UNESCO/Confederation of Scientific and Technological Associations in Malaysia and the Society for free Radical Research—Asia, held on Sep. 1-3, 1994, in Penang, Malaysia, AOCS Press, Champaign, Ill. X, 374 S).

Thiamine (vitamin $B_1$) is formed by chemical coupling of pyrimidine and thiazole units. Riboflavin (vitamin $B_2$) is synthesized from guanosine 5'-triphosphate (GTP) and ribose 5-phosphate. Riboflavin in turn is employed for the synthesis of flavin mononucleotide (FMN) and flavin-adenine dinucleotide (FAD). The family of compounds referred to jointly as "vitamin B6" (e.g. pyridoxine, pyridoxamine, pyridoxal 5-phosphate and the commercially used pyridoxine hydrochloride) are all derivatives of the common structural unit 5-hydroxy-6-methylpyridine. Pantothenate (pantothenic acid, R-(+)-N-(2,4-dihydroxy-3,3-dimethyl-1-oxobutyl)-β-alanine) can be produced either by chemical synthesis or by fermentation. The last steps in pantothenate biosynthesis consist of ATP-driven condensation of β-alanine and pantoic acid. The enzymes responsible for the biosynthetic steps for conversion into pantoic acid, into β-alanine and for condensation to pantothenic acid are known. The metabolically active form of pantothenate is coenzyme A, whose biosynthesis proceeds through 5 enzymatic steps. Pantothenate, pyridoxal 5-phosphate, cysteine and ATP are the precursors of coenzyme A. These enzymes catalyze not only the formation of pantothenate but also the production of (R)-pantoic acid, (R)-pantolactone, (R)-panthenol (provitamin $B_5$), pantethein (and its derivatives) and coenzyme A.

The biosynthesis of biotin from the precursor molecule pimeloyl-CoA in microorganisms has been investigated in detail, and several of the genes involved have been identified. It has emerged that many of the corresponding proteins are involved in Fe cluster synthesis and belong to the class of nifS proteins. Lipoic acid is derived from octanoic acid and serves as coenzyme in energy metabolism, where it becomes a constituent of the pyruvate dehydrogenase complex and of the α-ketoglutarate dehydrogenase complex. The folates are a group of substances which are all derived from folic acid, which in turn is derived from L-glutamic acid, p-aminobenzoic acid and 6-methylpterin. The biosynthesis of folic acid and its derivatives starting from the metabolic intermediates guanosine 5'-triphosphate (GTP), L-glutamic acid and p-aminobenzoic acid has been investigated in detail in certain microorganisms.

Corrinoids (such as the cobalamins and in particular vitamin $B_{12}$) and the porphyrins belong to a group of chemicals which are distinguished by a tetrapyrrole ring system. The biosynthesis of vitamin $B_{12}$ is so complex that it has not yet been completely characterized, but most of the enzymes and substrates involved are now known. Nicotinic acid (nicotinate) and nicotinamide are pyridine derivatives, which are also referred to as "niacin". Niacin is the precursor of the important coenzymes NAD (nicotinamide-adenine dinucleotide) and NADP (nicotinamide-adenine dinucleotide phosphate) and their reduced forms.

The production of these compounds on the industrial scale is based for the most part on cell-free chemical syntheses, although some of these chemicals have likewise been produced by large-scale culturing of microorganisms, such as riboflavin, vitamin $B_6$, pantothenate and biotin. Only vitamin $B_{12}$ is produced solely by fermentation, because of the complexity of its synthesis. In vitro methods require a considerable expenditure of materials and time and frequently of high costs.

III. Purine, Pyrimidine, Nucleoside and Nucleotide Metabolism and Uses

Genes for purine and pyrimidine metabolism and their corresponding proteins are important targets for the therapy of neoplastic diseases and viral infections. The term "purine" or "pyrimidine" comprises nitrogenous bases which are a constituent of nucleic acids, coenzymes and nucleotides. The term "nucleotide" comprises the fundamental structural units of nucleic acid molecules, which include a nitrogenous base, a pentose sugar (the sugar in RNA is ribose, and the sugar in DNA is D-deoxyribose) and phosphoric acid. The term "nucleoside" comprises molecules which serve as precursors of nucleotides but which, in contrast to nucleotides, have no phosphoric acid unit. It is possible by inhibiting the biosynthesis of these molecules or their mobilization for formation of nucleic acid molecules to inhibit RNA and DNA synthesis; targeted inhibition of this activity in carcinogenic cells allows the ability of tumor cells to divide and replicate to be inhibited.

There are also nucleotides which do not form nucleic acid molecules but serve as energy stores (i.e. AMP) or as coenzymes (i.e. FAD and NAD).

Several publications have described the use of these chemicals for these medical indications, where purine and/or pyrimidine metabolism is influenced (e.g. Christopherson, R. I. and Lyons, S.D. (1990) "Potent inhibitors of de novo pyrimidine and purine biosynthesis as chemotherapeutic agents", Med. Res. Reviews 10: 505-548). Investigations on enzymes involved in purine and pyrimidine metabolism have concentrated on the development of novel medicaments which can be used for example as immunosuppressants or antiproliferatives (Smith, J. L. "Enzymes in Nucleotide Synthesis" Curr. Opin. Struct. Biol. 5 (1995) 752-757; Biochem. Soc. Transact. 23 (1995) 877-902). Purine and pyrimidine bases, nucleosides and nucleotides have, however, also other possible uses: as intermediates in the biosynthesis of various fine chemicals (e.g. thiamine, S-adenosylmethionine, folates or riboflavin), as energy carriers for the cell (e.g. ATP or GTP) and for chemicals themselves, are commonly used as flavor enhancers (e.g. IMP or GMP) or for many medical applicatons (see, for example, Kuninaka, A., (1996) "Nucleotides and Related Compounds" in Biotechnology, vol. 6, Rehm et al., editors VCH: Weinheim, pp. 561-612). Enzymes involved in purine, pyridine, nucleoside or nucleotide metabolism are also increasingly serving as targets for the development of chemicals for crop protection, including fungicides, herbicides and insecticides.

The metabolism of these compounds in bacteria has been characterized (for reviews, see, for example, Zalkin, H. and Dixon, J. E. (1992) "De novo purine nucleotide biosynthesis" in Progress in Nucleic Acids Research and Molecular biology, vol. 42, Academic Press, pp. 259-287; and Michal, G. (1999) "Nucleotides and Nucleosides"; chapter 8 in: Biochemical Pathways: An Atlas of Biochemistry and Molecular Biology, Wiley, New York). Purine metabolism, which is the subject of intensive research, is essential for normal functioning of the cell. Impaired purine metabolism in higher animals may cause severe disorders, e.g. gout. The purine nucleotides are synthesized over a number of steps via the intermediate compound inosine 5'-phosphate (IMP) from ribose 5-phosphate, leading to production of guanosine 5'-monophosphate (GMP) or adenosine 5'-monophosphate (AMP), from which the triphosphate forms, which are used as nucleotides, can easily be prepared. These compounds are also used as energy stores, so that their degradation provides energy for many different biochemical processes in the cell. Pyrimidine biosynthesis takes place via the formation of uridine 5'-monophosphate (UMP) from ribose 5-phosphate. UMP in turn is converted into cytidine 5'-triphosphate (CTP). The deoxy forms of all nucleotides are prepared in a one-step reduction reaction from the diphosphate ribose form of the nucleotide to give the diphosphate deoxyribose form of the nucleotide. After phosphorylation, these molecules are able to take part in DNA synthesis.

IV. Trehalose Metabolism and Uses

Trehalose consists of two glucose molecules which are linked together via an α,α-1,1 linkage. It is commonly used in the food industry as sweetener, as additive to dried or frozen foods and in beverages. However, it is also used in the pharmaceutical industry, the cosmetics and biotechnology industry (see, for example, Nishimoto et al., (1998) U.S. Pat. No. 5,759,610; Singer, M. A. and Lindquist, S. Trends Biotech. 16 (1998) 460-467; Paiva, C. L. A. and Panek, A. D. Biotech Ann. Rev. 2 (1996) 293-314; and Shiosaka, M. FFIJ. Japan 172 (1997) 97-102). Trehalose is produced by enzymes of many microorganisms and is released in a natural way into the surrounding medium, from which it can be isolated by methods known in the art.

Particularly preferred biosynthetic products are selected from the group of organic acids, proteins, nucleotides and nucleosides, both proteinogenic and non-proteinogenic amino acids, lipids and fatty acids, diols, carbohydrates, aromatic compounds, vitamins and cofactors, enzymes and proteins.

Preferred organic acids are tartaric acid, itaconic acid and diaminopimelic acid.

Preferred nucleosides and nucleotides are described for example in Kuninaka, A. (1996) Nucleotides and related compounds, pp. 561-612, in Biotechnology, vol. 6, Rehm et al., editors VCH: Weinheim and references present therein.

Preferred biosynthetic products are additionally lipids, saturated and unsaturated fatty acids such as, for example, arachidonic acid, diols such as, for example, propanediol and butanediol, carbohydrates such as, for example, hyaluronic acid and trehalose, aromatic compounds such as, for example, aromatic amines, vanillin and indigo, vitamins and cofactors as described for example in Ullmann's Encyclopedia of Industrial Chemistry, vol. A27, "Vitamins", pp. 443-613 (1996) VCH: Weinheim and the references present therein; and Ong, A. S., Niki, E. and Packer, L. (1995) "Nutrition, Lipids, Health and Disease" Proceedings of the UNESCO/Confederation of Scientific and Technological Associations in Malaysia and the Society for Free Radical Research—Asia, held on Sep. 1-3, 1994 in Penang, Malaysia, AOCS Press (1995)), enzymes, polyketides (Cane et al. (1998) Science 282: 63-68) and all other chemicals described by Gutcho (1983) in Chemicals by Fermentation, Noyes Data Corporation, ISBN: 0818805086 and the references indicated therein.

Particularly preferred biosynthetic products are amino acids, particularly preferably essential amino acids, in particular L-glycine, L-alanine, L-leucine, L-methionine, L-phenylalanine, L-tryptophan, L-lysine, L-glutamine, L-glutamic acid, L-serine, L-proline, L-valine, L-isoleucine, L-cysteine, L-tyrosine, L-histidine, L-arginine, L-asparagine, L-aspartic acid and L-threonine, L-homoserine, especially L-lysine, L-methionine and L-threonine. An amino acid such as, for example, lysine, methionine and threonine means hereinafter both in each case the L and the D form of the amino acid, preferably the L form, i.e. for example L-lysine, L-methionine and L-threonine.

The invention relates in particular to a method for producing lysine by cultivating genetically modified microorganisms with increased or caused expression rate of at least one gene compared with the wild type, where ch) the specific expression activity in the microorganism of at least one endogenous expression unit of the invention, which regulates the expression of the endogenous genes, is increased compared with the wild type, or dh) the expression of genes in the microorganism is regulated by expression units of the invention or by expression units with increased specific expression activity as set forth in embodiment a), where the genes are heterologous in relation to the expression units, and where the genes are selected from the group of nucleic acids encoding an aspartate kinase, nucleic acids encoding an aspartate-semialdehyde dehydrogenase, nucleic acids encoding a diaminopimelate dehydrogenase, nucleic acids encoding a diaminopimelate decarboxylase, nucleic acids encoding a dihydrodipicolinate synthetase, nucleic acids encoding a dihydrodipicolinate reductase, nucleic acids encoding a glyceraldehyde-3-phosphate dehydrogenase, nucleic acids encoding a 3-phosphoglycerate kinase, nucleic acids encoding a pyruvate carboxylase, nucleic acids encoding a triosephosphate isomerase, nucleic acids encoding a transcriptional regulator LuxR, nucleic acids encoding a transcriptional regulator LysR1, nucleic acids encoding a transcriptional regulator LysR2, nucleic acids encoding a malate-quinone oxidoreductase, nucleic acids encoding a glucose-6-phosphate dehydrogenase, nucleic acids encoding a 6-phosphogluconate dehydrogenase, nucleic acids encoding a transketolase, nucleic acids encoding a transaldolase, nucleic acids encoding a lysine exporter, nucleic acids encoding a biotin ligase, nucleic acids encoding an arginyl-tRNA synthetase, nucleic acids encoding a phosphoenolpyruvate carboxylase, nucleic acids encoding a fructose-1,6-bisphosphatase, nucleic acids encoding a protein OpcA, nucleic acids encoding a 1-phosphofructokinase and nucleic acids encoding a 6-phosphofructokinase.

As described above for the methods, the regulation of the expression of these genes in the microorganism by expression units of the invention or by expression units of the invention with increased specific expression activity in accordance with embodiment ch) is achieved by dh1) introducing one or more expression units of the invention, where appropriate with increased specific expression activity, into the genome of the microorganism so that expression of one or more endogenous genes takes place under the control of the introduced expression units of the invention, where appropriate with increased specific expression activity, or dh2) introducing one or more of these genes into the genome of the microorganism so that expression of one or more of the introduced genes takes place under the control of the endogenous expression units of the invention, where appropriate with increased specific expression activity, or dh3) introducing one or more nucleic acid constructs comprising an expression unit of the invention, where appropriate with increased specific expression activity, and functionally linked one or more nucleic acids to be expressed, into the microorganism.

A further preferred embodiment of the method described above for preparing lysine comprises the genetically modified microorganisms, compared with the wild type, having additionally an increased activity, of at least one of the activities selected from the group of aspartate kinase activity, aspartate-semialdehyde dehydrogenase activity, diaminopimelate dehydrogenase activity, diaminopimelate decarboxylase activity, dihydrodipicolinate synthetase activity, dihydrodipicolinate reductase activity, glyceraldehyde-3-phosphate dehydrogenase activity, 3-phosphoglycerate kinase activity, pyruvate carboxylase activity, triosephosphate isomerase activity, activity of the transcriptional regulator LuxR, activity of the transcriptional regulator LysR1, activity of the transcriptional regulator LysR2, malate-quinone oxidoreductase activity, glucose-6-phosphate dehydrogenase activity, 6-phosphogluconate dehydrogenase activity, transketolase activity, transaldolase activity, lysine exporter activity, arginyl-tRNA synthetase activity, phosphoenolpyruvate carboxylase activity, fructose-1,6-bisphosphatase activity, protein OpcA activity, 1-phosphofructokinase activity, 6-phosphofructokinase activity and biotin ligase activity.

A further particularly preferred embodiment of the method described above for preparing lysine comprises the genetically modified microorganisms having, compared with the wild type, additionally a reduced activity, of at least one of the activities selected from the group of threonine dehydratase activity, homoserine O-acetyl-transferase activity, O-acetylhomoserine sulfhydrylase activity, phosphoenolpyruvate carboxykinase activity, pyruvate oxidase activity, homoserine kinase activity, homoserine dehydrogenase activity, threonine exporter activity, threonine efflux protein activity, asparaginase activity, aspartate decarboxylase activity and threonine synthase activity.

These additional increased or reduced activities of at least one of the activities described above may, but need not, be caused by a nucleic acid of the invention having promoter activity and/or an expression unit of the invention.

The invention further relates to a method for producing methionine by cultivating genetically modified microorganisms with increased or caused expression rate of at least one gene compared with the wild type, where ch) the specific expression activity in the microorganism of at least one endogenous expression unit of the invention, which regulates the expression of the endogenous genes, is increased compared with the wild type, or dh) the expression of genes in the microorganism is regulated by expression units of the invention or by expression units of the invention with increased specific expression activity as set forth in embodiment a), where the genes are heterologous in relation to the expression units, and where the genes are selected from the group of nucleic acids encodng an aspartate kinase, nucleic acids encoding an aspartate-semialdehyde dehydrogenase, nucleic acids encoding a homoserine dehydrogenase, nucleic acids encoding a glyceraldehyde-3-phosphate dehydrogenase, nucleic acids encoding a 3-phosphoglycerate kinase, nucleic acids encoding a pyruvate carboxylase, nucleic acids encoding a triosephosphate isomerase, nucleic acids encoding a homoserine O-acetyltransferase, nucleic acids encoding a cystathionine gamma-synthase, nucleic acids encoding a cystathionine beta-lyase, nucleic acids encoding a serine hydroxymethyltransferase, nucleic acids encoding an O-acetylhomoserine sulfhydrylase, nucleic acids encoding a methylenetetrahydrofolate reductase, nucleic acids encoding a phosphoserine aminotransferase, nucleic acids encoding a phosphoserine phosphatase, nucleic acids encoding a serine acetyltransferase, nucleic acids encoding a cysteine synthase 1, nucleic acids encoding a cysteine synthase II activity, nucleic acids encoding a coenzyme B12-dependent methionine synthase activity, nucleic acids encoding a coenzyme B12-independent methionine synthase activity, nucleic acids encoding a sulfate adenylyltransferase activity, nucleic acids encoding a phosphoadenosine phosphosulfate reductase activity, nucleic acids encoding a ferredoxin-sulfite reductase activity, nucleic acids encoding a ferredoxin NADPH-reductase activity, nucleic acids encoding a ferredoxin activity, nucleic acids encoding a protein of sulfate reduction RXA077, nucleic acids encoding a protein of sulfate reduction RXA248, nucleic acids encoding a protein of sulfate reduction RXA247, nucleic acids encoding an RXA0655 regulator and nucleic acids encoding an RXN2910 regulator.

As described above for the methods, the regulation of the expression of these genes in the microorganism by expression units of the invention or by expression units of the invention with increased specific expression activity according to embodiment ch) is achieved by dh1) introducing one or more expression units of the invention, where appropriate with increased specific expression activity, into the genome of the microorganism so that expression of one or more of these endogenous genes takes place under the control of the introduced expression units of the invention, where appropriate with increased specific expression activity, or dh2) introducing one or more genes into the genome of the microorganism so that expression of one or more of the introduced genes takes place under the control of the endogenous expression units of the invention, where appropriate with increased specific expression activity, or dh3) introducing one or more nucleic acid constructs comprising an expression unit of the invention, where appropriate with increased specific expression activity, and functionally linked one or more nucleic acids to be expressed, into the microorganism.

A further preferred embodiment of the method described above for preparing methionine comprises the genetically modified microorganisms having, compared with the wild type, additionally an increased activity, of at least one of the activities selected from the group of aspartate kinase activity, aspartate-semialdehyde dehydrogenase activity, homoserine dehydrogenase activity, glyceraldehyde-3-phosphate dehydrogenase activity, 3-phosphoglycerate kinase activity; pyruvate carboxylase activity, triosephosphate isomerase activity, homoserine O-acetyltransferase activity, cystathionine gamma-synthase activity, cystathionine beta-lyase activity, serine hydroxymethyltransferase activity, O-acetylhomoserine sulfhydrylase activity, methylenetetrahydrofolate reductase activity, phosphoserine aminotransferase activity, phosphoserine phosphatase activity, serine acetyltransferase activity, cysteine synthase I activity, cysteine synthase II activity, coenzyme B12-dependent methionine synthase activity, coenzyme B12-independent methionine synthase activity, sulfate adenylyltransferase activity, phosphoadenosine-phosphosulfate reductase activity, ferredoxin-sulfite reductase activity, ferredoxin NADPH-reductase activity, ferredoxin activity, activity of a protein of sulfate reduction RXA077, activity of a protein of sulfate reduction RXA248, activity of a protein of sulfate reduction RXA247, activity of an RXA655 regulator and activity of an RXN2910 regulator.

A further particularly preferred embodiment of the method described above for preparing methionine comprises the genetically modified microorganisms having, compared with the wild type, additionally a reduced activity, of at least one of the activities selected from the group of homoserine kinase activity, threonine dehydratase activity, threonine synthase activity, meso-diaminopimelate D-dehydrogenase activity, phosphoenolpyruvate carboxykinase activity, pyruvate oxidase activity, dihydrodipicolinate synthase activity, dihydrodipicolinate reductase activity and diaminopicolinate decarboxylase activity.

These additional increased or reduced activities of at least one of the activities described above may, but need not, be caused by a nucleic acid of the invention having promoter activity and/or an expression unit of the invention.

The invention further relates to a method for preparing threonine by cultivating genetically modified microorganisms with increased or caused expression rate of at least one gene compared with the wild type, where ch) the specific expression activity in the microorganism of at least one endogenous expression unit of the invention, which regulates the expression of the endogenous genes, is increased compared with the wild type, or dh) the expression of genes in the microorganism is regulated by expression units of the invention or by expression units of the invention with increased specific expression activity as set forth in embodiment a), where the genes are heterologous in relation to the expression units, and where the genes are selected from the group of nucleic acids encoding an aspartate kinase, nucleic acids encoding an aspartate-semialdehyde dehydrogenase, nucleic acids encoding a glyceraldehyde-3-phosphate dehydrogenase, nucleic acids encoding a 3-phosphoglycerate kinase, nucleic acids encoding a pyruvate carboxylase, nucleic acids encoding a triosephosphate isomerase, nucleic acids encoding a homoserine kinase, nucleic acids encoding a threonine synthase, nucleic acids encoding a threonine exporter carrier, nucleic acids encoding a glucose-6-phosphate dehydrogenase, nucleic acids encoding a transaldolase, nucleic acids encoding a transketolase, nucleic acids encoding a malate-quinone oxidoreductase, nucleic acids encoding a 6-phosphogluconate dehydrogenase, nucleic acids encoding a lysine exporter, nucleic acids encoding a biotin ligase, nucleic acids encoding a phosphoenolpyruvate carboxylase, nucleic acids encoding a threonine efflux protein, nucleic acids encoding a fructose-1,6-bisphosphatase, nucleic acids encoding an OpcA protein, nucleic acids encoding a 1-phosphofructokinase, nucleic acids encoding a 6-phosphofructokinase, and nucleic acids encoding a homoserine dehydrogenase.

As described above for the methods, the regulation of the expression of these genes in the microorganism by expression units of the invention or by expression units of the invention with increased specific expression activity according to embodiment ch) is achieved by dh1) introducing one or more expression units of the invention, where appropriate with increased specific expression activity, into the genome of the microorganism so that expression of one or more of these endogenous genes takes place under the control of the introduced expression units of the invention, where appropriate with increased specific expression activity, or dh2) introducing one or more of these genes into the genome of the microorganism so that expression of one or more of the introduced genes takes place under the control of the endogenous expression units of the invention, where appropriate with increased specific expression activity, or dh3) introducing one or more nucleic acid constructs comprising an expression unit of the invention, where appropriate with increased specific expression activity, and functionally linked one or more nucleic acids to be expressed, into the microorganism.

A further preferred embodiment of the method described above for preparing threonine comprises the genetically modified microorganisms having, compared with the wild type, additionally an increased activity, of at least one of the activities selected from the group of aspartate kinase activity, aspartate-semialdehyde dehydrogenase activity, glyceraldehyde-3-phosphate dehydrogenase activity, 3-phosphoglycerate kinase activity, pyruvate carboxylase activity, triosephosphate isomerase activity, threonine synthase activity, activity of a threonine export carrier, transaldolase activity, transketolase activity, glucose-6-phosphate dehydrogenase activity, malate-quinone oxidoreductase activity, homoserine kinase activity, biotin ligase activity, phosphoenolpyruvate carboxylase activity, threonine efflux protein activity, protein OpcA activity, 1-phosphofructokinase activity, 6-phosphofructokinase activity, fructose-1,6-bisphosphatase activity, 6-phosphogluconate dehydrogenase and homoserine dehydrogenase activity.

A further particularly preferred embodiment of the method described above for preparing threonine comprises the genetically modified microorganisms having, compared with the wild type, additionally a reduced activity, of at least one of the activities selected from the group of threonine dehydratase activity, homoserine O-acetyltransferase activity, serine hydroxymethyltransferase activity, O-acetylhomoserine sulfhydrylase activity, meso-diaminopimelate D-dehydrogenase activity, phosphoenolpyruvate carboxykinase activity, pyruvate oxidase activity, dihydrodipicolinate synthetase activity, dihydrodipicolinate reductase activity, asparaginase activity, aspartate decarboxylase activity, lysine exporter activity, acetolactate synthase activity, ketol-acid reductoisomerase activity, branched chain aminotransferase activity, coenzyme B12-dependent methionine synthase activity, coenzyme B12-independent methionine synthase activity, dihydroxy-acid dehydratase activity and diaminopicolinate decarboxylase activity.

These additional increased or reduced activities of at least one of the activities described above may, but need not, be caused by a nucleic acid of the invention having promoter activity and/or an expression unit of the invention.

The term "activity" of a protein means in the case of enzymes the enzymic activity of the corresponding protein, and in the case of other proteins, for example structural or transport proteins, the physiological activity of the proteins.

The enzymes are ordinarily able to convert a substrate into a product or catalyze this conversion step.

Accordingly, the "activity" of an enzyme means the quantity of substrate converted by the enzyme, or the quantity of product formed, in a particular time.

Thus, where an activity is increased compared with the wild type, the quantity of the substrate converted by the enzyme, or the quantity of product formed, in a particular time is increased compared with the wild type.

This increase in the "activity" preferably amounts, for all activities described hereinbefore and hereinafter, to at least 5%, further preferably at least 20%, further preferably at least 50%, further preferably at least 100%, more preferably at least 300%, even more preferably at least 500%, especially at least 600% of the "activity of the wild type".

Thus, where an activity is reduced compared with the wild type, the quantity of substrate converted by the enzyme, or the quantity of product formed, in a particular time is reduced compared with the wild type.

A reduced activity preferably means the partial or substantially complete suppression or blocking, based on various cell biological mechanisms, of the functionality of this enzyme in a microorganism.

A reduction in the activity comprises a quantitative decrease in an enzyme as far as substantially complete absence of the enzyme (i.e. lack of detectability of the corresponding activity or lack of immunological detectability of the enzyme). The activity in the microorganism is preferably reduced, compared with the wild type, by at least 5%, further preferably by at least 20%, further preferably by at least 50%, further preferably by 100%. "Reduction" also means in particular the complete absence of the corresponding activity.

The activity of particular enzymes in genetically modified microorganisms and in the wild type, and thus the increase or reduction in the enzymic activity, can be measured by known methods such as, for example, enzyme assays.

For example, a pyruvate carboxylase means a protein which exhibits the enzymatic activity of converting pyruvate into oxaloacetate.

Correspondingly, a pyruvate carboxylase activity means the quantity of pyruvate converted by the pyruvate carboxlyase protein, or quantity of oxaloacetate formed, in a particular time.

Thus, where a pyruvate carboxylase activity is increased compared with the wild type, the quantity of pyruvate converted by the pyruvate carboxylase protein, or the quantity of oxaloacetate formed, in a particular time is increased compared with the wild type.

This increase in the pyruvate carboxylase activity is preferably at least 5%, further preferably at least 20%, further preferably at least 50%, further preferably at least 100%, more preferably at least 300%, even more preferably at least 500%, in particular at least 600%, of the pyruvate carboxylase activity of the wild type.

In addition, for example a phosphoenolpyruvate carboxykinase activity means the enzymic activity of a phosphoenolpyruvate carboxykinase.

A phosphoenolpyruvate carboxykinase means a protein which exhibits the enzymatic activity of converting oxaloacetate into phosphoenolpyruvate.

Correspondingly, phosphoenolpyruvate carboxykinase activity means the quantity of oxaloacetate converted by the phosphoenolpyruvate carboxykinase protein, or quantity of phosphoenolpyruvate formed, in a particular time.

When the phosphoenolpyruvate carboxykinase activity is reduced compared with the wild type, therefore, the quantity of oxaloacetate converted by the phosphoenolpyruvate carboxykinase protein, or the quantity of phosphoenolpyruvate formed, in a particular time, is reduced compared with the wild type.

A reduction in phosphoenolpyruvate carboxykinase activity comprises a quantitative decrease in a phosphoenolpyruvate carboxykinase as far as a substantially complete absence of phosphoenolpyruvate carboxykinase (i.e. lack of detectability of phosphoenolpyruvate carboxykinase activity or lack of immunological detectability of phosphoenolpyruvate carboxykinase). The phosphoenolpyruvate carboxykinase activity is preferably reduced, compared with the wild type, by at least 5%, further preferably by at least 20%, further preferably by at least 50%, further preferably by 100%. In particular, "reduction" also means the complete absence of phosphoenolpyruvate carboxykinase activity.

The additional increasing of activities can take place in various ways, for example by switching off inhibitory regulatory mechanisms at the expression and protein level or by increasing gene expression of nucleic acids encoding the proteins described above compared with the wild type.

Increasing the gene expression of the nucleic acids encoding the proteins described above compared with the wild type can likewise take place in various ways, for example by inducing the gene by activators or, as described above, by increasing the promoter activity or increasing the expression activity or by introducing one or more gene copies into the microorganism.

Increasing the gene expression of a nucleic acid encoding a protein also means according to the invention manipulation of the expression of endogenous proteins intrinsic to the microorganism.

This can be achieved for example, as described above, by altering the promoter and/or expression unit sequences of the genes. Such an alteration, which results in an increased expression rate of the gene, can take place for example by deletion or insertion of DNA sequences.

It is possible, as described above, to alter the expression of endogenous proteins by applying exogenous stimuli. This can take place through particular physiological conditions, i.e. through the application of foreign substances.

The skilled worker may have recourse to further different procedures, singly or in combination, to achieve an increase in gene expression. Thus, for example, the copy number of the appropriate genes can be increased, or the promoter and regulatory region or the ribosome binding site located upstream of the structural gene can be mutated. It is additionally possible to increase the expression during fermentative production through inducible promoters. Procedures to prolong the lifespan of the mRNA likewise improve expression. Enzymic activity is likewise enhanced also by preventing degradation of enzyme protein. The genes or gene constructs may be either present in plasmids with varying copy number or integrated and amplified in the chromosome. It is also possible as an alternative to achieve overexpression of the relevant genes by altering the composition of the media and management of the culture.

The skilled worker can find guidance on this inter alia in Martin et al. (Biotechnology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in European patent 0472869, in U.S. Pat. No. 4,601,893, in Schwarzer and Pühler (Biotechnology 9, 84-87 (1991)), in Reinscheid et al. (Applied and Environmental Microbiology 60, 126-132 (1994), in LaBarre et al. (Journal of Bacteriology 175, 1001-1007 (1993)), in the patent application WO 96/15246, in Malumbres et al. (Gene 134, 15-24 (1993)), in the Japanese published specification JP-A-10-229891, in Jensen and Hammer (Biotechnology and Bioengineering 58, 191-195 (1998)), in Makrides (Microbiological Reviews 60: 512-538 (1996) and in well-known textbooks of genetics and molecular biology.

It may additionally be advantageous for the production of biosynthetic products, especially L-lysine, L-methionine and L-threonine, besides the expression or enhancement of a gene, to eliminate unwanted side reactions (Nakayama: "Breeding of Amino Acid Producing Microorganisms", in: Overproduction of Microbial Products, Krumphanzl, Sikyta, Vanek (eds.), Academic Press, London, UK, 1982).

In a preferred embodiment, gene expression of a nucleic acid encoding one of the proteins described above is increased by introducing at least one nucleic acid encoding a corresponding protein into the microorganism. The introduction of the nucleic acid can take place chromosomally or extrachromosomally, i.e. through increasing the copy number on the chromosome and/or a copy of the gene on a plasmid which replicates in the host microorganism.

The introduction of the nucleic acid, for example in the form of an expression cassette comprising the nucleic acid, preferably takes place chromosomally, in particular by the SacB method described above.

It is possible in principle to use for this purpose any gene which encodes one of the proteins described above.

In the case of genomic nucleic acid sequences from eukaryotic sources which comprise introns, if the host microorganism is unable or cannot be made able to express the corresponding proteins it is preferred to use nucleic acid sequences which have already been processed, such as the corresponding cDNAs.

Examples of the corresponding genes are listed in Table 1 and 2.

The activities described above in microorganisms are preferably reduced by at least one of the following methods:
- introduction of at least one sense ribonucleic acid sequence for inducing cosuppression or of an expression cassette ensuring expression thereof
- introduction of at least one DNA- or protein-binding factor against the corresponding gene, RNA or protein or of an expression cassette ensuring expression thereof
- introduction of at least one viral nucleic acid sequence which causes RNA degradation, or of an expression cassette ensuring expression thereof
- introduction of at least one construct to produce a loss of function, such as, for example, generation of stop codons or a shift in the reading frame, of a gene, for example by producing an insertion, deletion, inversion or mutation in a gene. It is possible and preferred to generate knockout mutants by targeted insertion into the desired target gene through homologous recombination or introduction of sequence-specific nucleases against the target gene.
- introduction of a promoter with reduced promoter activity or of an expression unit with reduced expression activity.

The skilled worker is aware that further methods can also be employed within the scope of the present invention for reducing its activity or function. For example, the introduction of a dominant negative variant of a protein or of an expression cassette ensuring expression thereof may also be advantageous.

It is moreover possible for each single one of these methods to bring about a reduction in the quantity of protein, quantity of mRNA and/or activity of a protein. A combined use is also conceivable. Further methods are known to the skilled worker and may comprise impeding or suppressing the processing of the protein, of the transport of the protein or its mRNA, inhibition of ribosome attachment, inhibition of RNA splicing, induction of an RNA-degrading enzyme and/or inhibition of translation elongation or termination.

In the method of the invention for producing biosynthetic products, the step of cultivation of the genetically modified microorganisms is preferably followed by an isolation of biosynthetic products from the microorganisms or/or from the fermentation broth. These steps may take place at the same time and/or preferably after the cultivation step.

The genetically modified microorganisms of the invention can be cultivated to produce biosynthetic products, in particular L-lysine, L-methionine and L-threonine, continuously or discontinuously in a batch method (batch cultivation) or in the fed batch or repeated fed batch method. A summary of known cultivation methods is to be found in the textbook by Chmiel (Bioprozeβechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must satisfy in a suitable manner the demands of the respective strains. There are descriptions of culture media for various microorganisms in the handbook "Manual of Methods for General Bacteriology" of the American Society for Bacteriology (Washington D.C., USA, 1981).

These media which can be employed according to the invention usually comprise one or more carbon sources, nitrogen sources, inorganic salts, vitamins and/or trace elements.

Preferred carbon sources are sugars such as mono-, di- or polysaccharides. Examples of very good carbon sources are glucose, fructose, mannose, galactose, ribose, ribose, sorbose, ribulose, lactose, maltose, sucrose, raffinose, starch or cellulose. Sugars can be put in the media also via complex compounds such as molasses, or other by-products of sugar refining. It may also be advantageous to add mixtures of various carbon sources. Other possible carbon sources are oils and fats such as, for example, soybean oil, sunflower oil, peanut oil and coconut fat, fatty acids such as, for example, palmitic acid, stearic acid or linoleic acid, alcohols such as, for example, glycerol, methanol or ethanol and organic acids such as, for example, acetic acid or lactic acid.

Nitrogen sources are usually organic or inorganic nitrogen compounds or materials containing these compounds. Examples of nitrogen sources include ammonia gas or ammonium salts such as ammonium sulfate, ammonium chloride, ammonium phosphate, ammonium carbonate or ammonium nitrate, nitrates, urea, amino acids or complex nitrogen sources such as corn steep liquor, soybean flour, soybean protein, yeast extract, meat extract and others. The nitrogen sources may be used singly or as mixtures.

Inorganic salt compounds which may be present in the media comprise the chloride, phosphoric or sulfate salts of calcium, magnesium, sodium, cobalt, molybdenum, potassium, manganese, zinc, copper and iron.

For producing fine chemicals, especially methionine, it is possible to use as sulfur source inorganic compounds such as, for example, sulfates, sulfites, dithionites, tetrathionates, thiosulfates, sulfides, but also organic sulfur compounds such as mercaptans and thiols.

It is possible to use as phosphorus source phosphoric acid, potassium dihydrogenphosphate or dipotassium hydrogenphosphate or the corresponding sodium-containing salts.

Chelating agents can be added to the medium in order to keep the metal ions in solution. Particularly suitable chelating agents comprise dihydroxyphenols such as catechol or protocatechuate, or organic acids such as citric acid.

The fermentation media employed according to the invention normally also comprise other growth factors such as vitamins or growth promoters, which include for example biotin, riboflavin, thiamine, folic acid, nicotinic acid, pantothenate and pyridoxine.

Growth factors and salts are frequently derived from complex components of the media, such as yeast extract; molasses, corn steep liquor and the like. Suitable precursors may also be added to the culture medium. The exact composition of the compounds in the media depends greatly on the particular experiment and will be decided individually for each specific case. Information on optimization of media is obtainable from the textbook "Applied Microbiol. Physiology, A Practical Approach" (editors P. M. Rhodes, P. F. Stanbury, IRL Press (1997) pp. 53-73, ISBN 0 19 963577 3). Growth media can also be purchased from commercial suppliers, such as Standard 1 (Merck) or BHI (Brain heart infusion, DIFCO) and the like.

All the components of the media are sterilized either by heat (20 min at 1.5 bar and 121° C.) or by sterilizing filtration. The components can be sterilized either together or, if necessary, separately. All the components of the media may be present at the start of culturing or optionally be added continuously or batchwise.

The temperature of the culture is normally between 15° C. and 45° C., preferably at 25° C. to 40° C. and can be kept constant or changed during the experiment. The pH of the medium should be in the range from 5 to 8.5, preferably around 7.0. The pH for the culturing can be controlled during the culturing by adding basic compounds such as sodium hydroxide, potassium hydroxide, ammonia or aqueous ammonia or acidic compounds such as phosphoric acid or sulfuric acid. The development of foam can be controlled by employing antifoams such as, for example, fatty acid polyglycol esters. The stability of plasmids can be maintained by adding to the medium suitable substances with a selective action, such as, for example, antibiotics. Aerobic conditions are maintained by introducing oxygen or oxygen-containing gas mixtures such as, for example, ambient air into the culture. The temperature of the culture is normally 20° C. to 45° C. The culture is continued until formation of the desired product is at a maximum. This aim is normally reached within 10 hours to 160 hours.

The dry matter content of the fermentation broths obtained in this way is normally from 7.5 to 25% by weight.

It is additionally advantageous also to run the fermentation with sugar limitation at least at the end, but in particular over at least 30% of the fermentation time. This means that the concentration of utilizable sugar in the fermentation medium is kept at 0 to 3 g/l, or is reduced, during this time.

Biosynthetic products are isolated from the fermentation broth and/or the microorganisms in a manner known per se in accordance with the physical/chemical properties of the required biosynthetic product and the biosynthetic by-products.

The fermentation broth can then be processed further for example. Depending on the requirement, the biomass can be removed wholly or partly from the fermentation broth by separation methods such as, for example, centrifugation, filtration, decantation or a combination of these methods, or left completely in it.

The fermentation broth can then be concentrated by known methods such as, for example, with the aid of a rotary evaporator, thin-film evaporator, falling-film evaporator, by reverse osmosis or by nanofiltration. This concentrated fermentation broth can then be worked up by freeze drying, spray drying, spray granulation or by other methods.

However, it is also possible to purify the biosynthetic products, especially L-lysine, L-methionine and L-threonine, further. For this purpose, the product-containing broth is subjected, after removal of the biomass, to a chromatography using a suitable resin, with the desired product or the impurities being retained wholly or partly on the chromatography resin. These chromatographic steps can be repeated if required, using the same or different chromatography resins. The skilled worker is proficient in the selection of suitable chromatography resins and their most effective use. The purified product can be concentrated by filtration or ultrafiltration and be stored at a temperature at which the stability of the product is a maximum.

The biosynthetic products may result in various forms, for example in the form of their salts or esters.

The identity and purity of the isolated compound(s) can be determined by prior art techniques. These comprise high performance liquid chromatography (HPLC), spectroscopic methods, staining methods, thin-layer chromatography, NIRS, enzyme assay or microbiological assays. These analytical methods are summarized in: Patek et al. (1994) Appl. Environ. Microbiol. 60:133-140; Malakhova et al. (1996) Biotekhnologiya 11 27-32; and Schmidt et al. (1998) Bioprocess Engineer. 19:67-70. Ulmann's Encyclopedia of Industrial Chemistry (1996) vol. A27, VCH: Weinheim, pp. 89-90, pp. 521-540, pp. 540-547, pp. 559-566, 575-581 and pp. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

The invention is now described in more detail by means of the following nonlimiting examples:

EXAMPLE 1

Construction of Plasmid pCIS lysC

In the first step of strain construction, an allelic exchange of the lysC wild-type gene in *Corynebacterium glutamicum* ATCC13032 was carried out. In this case, a nucleotide exchange was carried out in the lysC gene so that in the resulting protein the amino acid Thr at position 311 was replaced by an Ile. Starting from the chromosomal DNA from ATCC13032 as template for a PCR reaction, lysC was amplified with the oligonucleotide primers SEQ ID NO:5 and SEQ ID NO:6 with the aid of the Pfu-Turbo PCR system (Stratagene USA) in accordance with the manufacturer's instructions.

SEQ ID NO: 5
5'-GAGAGAGAGACGCGTCCCAGTGGCTGAGACGCATC-3'

SEQ ID NO: 6
5'-CTCTCTCTGTCGACGAATTCAATCTTACGGCCTG-3'

Chromosomal DNA was prepared from *C. glutamicum* ATCC 13032 as described by Tauch et al. (1995) Plasmid 33:168-179 or Eikmanns et al. (1994) Microbiology 140: 1817-1828. The amplified fragment is flanked at its 5' end by a SalI restriction site and at its 3' end by a MluI restriction site. Before the cloning, the amplified fragment was digested with these two restriction enzymes and purified using GFX™PCR, DNA and Gel Band purification kit (Amersham Pharmacia, Freiburg).

The resulting polynucleotide was cloned via the SalI and MluI restriction sites into pCLIK5 MCS integrative SacB called pCIS hereinafter (SEQ ID NO: 7) and transformed into *E. coli* XL-1 blue. Selection for plasmid-harboring cells was achieved by plating out on LB agar (Lennox, 1955, Virology, 1:190) containing kanamycin (20 µg/ml). The plasmid was isolated and the expected nucleotide sequence was confirmed by sequencing. Preparation of the plasmid DNA was carried out by methods and with materials from Qiagen. Sequencing reactions were carried out as described by Sanger et al. (1977) Proceedings of the National Academy of Sciences USA 74:5463-5467. The sequencing reactions were fractionated and evaluated using an ABI prism 377 (PE Applied Biosystems, Weiterstadt). The resulting plasmid pCIS lysC is listed as SEQ ID NO:8.

EXAMPLE 2

Mutagenesis of the lysC Gene from *C. glutamicum*

Directed mutagenesis of the lysC gene from *C. glutamicum* was carried out with the Quickchange kit (from Stratagene/USA) in accordance with the manufacturer's instructions. The mutagenesis was carried out in the plasmid pCIS lysC, SEQ ID NO:8. For the exchange from thr 311 to 311 ile by means of the Quickchange method (Stratagene), the following oligonucleotide primers were synthesized:

SEQ ID NO: 9
5'-CGGCACCACCGACATCATCTTCACCTGCCCTCGTTCCG-3'

SEQ ID NO: 10
5'-CGGAACGAGGGCAGGTGAAGATGATGTCGGTGGTGCCG-3'

Use of these oligonucleotide primers in the Quickchange reaction leads to an exchange of the nucleotide in position 932 (from C to T) in the lysC gene SEQ ID NO: 11. The resulting amino acid exchange Thr311Ile in the lysC gene was confirmed after transformation into *E. coli* XL1-blue and plasmid preparation by a sequencing reaction. The plasmid received the designation pCIS lysC thr311 ile and is listed as SEQ ID NO:12.

The plasmid pCIS lysC thr311 ile was transformed into *C. glutamicum* ATCC13032 by electroporation as described by Liebl et al. (1989) FEMS Microbiology Letters 53:299-303. Modifications of the protocol are described in DE 10046870. The chromosomal arrangement of the lysC locus of individual transformants was checked by Southern blotting and hybridization using standard methods as described in Sambrook et al. (1989), Molecular Cloning. A Laboratory Manual, Cold Spring Harbor. This ensured that the transformants have integrated the transformed plasmid by homologous recombination at the lysC locus. After such colonies had grown overnight in media containing no antibody, the cells were plated out on a sucrose CM agar medium (10% sucrose, 10 g/l glucose; 2.5 g/l NaCl; 2 g/l urea, 10 g/l Bacto peptone (from Difco); 10 g/l yeast extract, 22.0 g/L agar (Difco)) and incubated at 30° C. for 24 hours.

Since the sacB gene present in the vector pCIS lysC thr311ile converts sucrose into a toxic product, the only colonies able to grow are those which have deleted the sacB gene by a second homologous recombination step between the wild-type lysC gene and the mutated lysC thr311ile gene. During the homologous recombination there may be deletion either of the wild-type gene or of the mutated gene together with the sacB gene. Deletion of the SacB gene together with the wild-type gene results in a mutated transformant.

Grown colonies were picked and investigated for a kanamycin-sensitive phenotype. Clones with deleted SacB gene must simultaneously show kanamycin-sensitive growth behavior. Such Kan-sensitive clones were investigated in a shaken flask for their lysine productivity (see example 6). The untreated *C. glutamicum* ATCC13032 was cultured for comparison. Clones with lysine production increased compared with the control were selected, chromosomal DNA isolated and the corresponding region of the lysC gene amplified by a PCR reaction and sequenced. Such a clone with the property of increased lysine synthesis and demonstrated mutation in lysC at position 932 was referred to as ATCC13032 lysC$^{fbr}$.

EXAMPLE 3

Preparation of an Integrated Plasmid for Overexpression of the lysC Gene with the Aid of the Heterologous Expression Unit Psod (SEQ. ID. NO. 2)

The following oligonucleotides were defined for amplification of the expression unit of the gene which codes for superoxide dismutase.

SEQ ID 13:
sod8: 5'-accctggcggaaaccctgagtcg-3'

SEQ ID 14:
sod1: 5'-tacgaccagggccacgggtaaaaaatcctttcgtaggtttc
cgcaccgagcatatacatcttttg-3'

The primers were employed in a PCR reaction with chromosomal DNA from *C. glutamicum* ATCC 13032. It was possible with this approach to amplify a DNA fragment which corresponded to the expected size of 657 bp.

The following oligonucleotides were defined for amplification of the gene which codes for aspartokinase.

SEQ ID 15
lysC2: 5'-cctacgaaaggattttttacccgtggccctggtcgtaca
g-3'

SEQ ID 16:
lysC6: 5'-gattagtggaacctcgtcgtc-3'

The primers were employed in a PCR reaction with chromosomal DNA from *C. glutamicum* ATCC13032 lysC$^{fbr}$. It was possible with this approach to amplify a DNA fragment which corresponded to the expected size of 1638 bp.

The primers sod1 and ask2 contain an overlapping sequence and are homologous to one another at their 5' ends.

The PCR products obtained above were employed as template for a further PCR in which the following primers were used.

SEQ ID 17:
sod4: 5'-gcggcgcaggattttctaa-3'

SEQ ID 18:
lysC4: 5'-tcggttgcctgagtaatgtctt-3'

It was possible with this approach to amplify a DNA fragment which corresponded to the expected size of 1811 bp. This Psod/lysC fusion was then cloned into the vector pCR2.1 (from Invitrogen GmbH, Karlsruhe, Germany). In a further step, the Psod/lysC fusion was cloned from the plasmid pCR2.1 (from Invitrogen GmbH, Karlsruhe, Germany) as 1773 bp EcoRI fragment into the integration vector pK19 mob sacB SEQ ID NO 19, which had previously been cut with the restriction endonuclease EcoRI. The resulting plasmid was referred to as pk19 mob sacB Psod lysC.

The following oligonucleotides were defined for amplification of a 5' region of the lysC gene:

SEQ ID 20:
lysC23: 5'-caccgcggctttggacatcactgctac-3'

SEQ ID 21:
lysC24: 5'-cctggggctttagcggatgcgtctca-3'

The primers were employed in a PCR reaction with chromosomal DNA from *C. glutamicum*. It was possible with this approach to amplify a DNA fragment which corresponded to the expected size of 674 bp. This DNA fragment was cloned into the vector pCR2.1 (from Invitrogen GmbH, Karlsruhe, Germany). A 787 bp SpeI/XbaI fragment was then subsequently cloned into the vector pK19 mob sacB Psod lysC, which had previously been digested with the restriction enzyme NheI. The resulting plasmid was referred to as pK19 mob sacB Psod lysC+US (SEQ ID 22). Up to this step, all clonings were carried out in *Escherichia coli* XL-1 Blue (from Stratagene, Amsterdam, Netherlands).

The transformation plasmid pK19 mob sacB Psod lysC+US was then used to transform *E. coli* Mn522 (from Stratagene, Amsterdam, Netherlands) together with the plasmid pTc15AcgIM as described by Liebl et al. (1989) FEMS Microbiology Letters 53:299-303. The plasmid pTc15AcgIM enables DNA to be methylated according to the methylation pattern of *Corynebacterium glutamicum* (DE 10046870). This step enables *Corynebacterium glutamicum* subsequently to undergo electroporation with the integration plasmid pK19 mob sacB Psod lysC+US. This electroporation and the subsequent selection on CM plates with kanamycin (25 μg/ml) resulted in a plurality of transconjugants. To select for the second recombination event, which should lead to excision of the vector together with the lysC promoter and the lysC gene, these transconjugants were cultured in CM medium without kanamycin overnight and then plated out on CM plates with 10% sucrose for selection. The sacB gene present on the vector pK19 mob sacB codes for the enzyme levansucrase and leads to the synthesis of levan on growth on sucrose. Since levan is toxic for *C. glutamicum*, the only *C. glutamicum* cells able to grow on sucrose-containing medium are those which have lost the integration plasmid through the second recombination step (Jäger et al., Journal of Bacteriology 174 (1992) 5462-5466). 100 sucrose-resistant clones were examined for their kanamycin sensitivity. It was possible to demonstrate for 57 of the tested clones not only resistance to sucrose but also sensitivity to kanamycin. A polymerase chain reaction (PCR) was used to check whether the desired replacement of the natural expression unit by the Psod expression unit had also taken place. Chromosomal DNA was isolated from the initial strain and 20 clones for this analysis. For this purpose, the respective clones were removed from the agar plate with a toothpick and suspended in 100 μl of $H_2O$ and boiled at 95° C. for 10 min. 10 μl portions of the resulting solution were employed as template in the PCR. The primers used were oligonucleotides which are homologous to the Psod expression unit and the lysC gene. The PCR conditions were chosen as follows: predenaturation: 5 min at 95° C.; denaturation 30 sec at 95° C.; hybridization 30 sec at 55° C.; amplification 2 min at 72° C.; 30 cycles; final extension 5 min at 72° C. In the mixture with the DNA of the initial strain it was not possible for a PCR product to result owing to the choice of the oligonucleotides. Only with clones in which the second recombination effected replacement of the natural promoter (PlysC) by Psod was a band with a size of 340 bp expected. In total, 2 of the tested 20 clones were positive.

EXAMPLE 4

Aspartokinase (lysC) Assay

*C. glutamicum* strains which contained either a chromosomal copy of the $lysC^{fbr}$ gene with the natural promoter or a chromosomal copy of the Psod $lysC^{fbr}$ construct were cultured in MMA medium (20 g/l glucose, 10 g/l $(NH_4)_2SO_4$*0.5 g $KH_2PO_4$*0.5 g $K_2HPO_4$*2.5 g urea, 5 g NaCl, 400 mg $MgSO_4.7H_2O$, 10 mg $FeSO_4$*$7H_2O$, $MnSO_4$*$6H_2O$, 100 mg L-leucine, 100 mg L-cysteine, 250 mg pantothenic acid, 5 mg nicotinamide, 100 μg biotin, 200 μg thiamine, 15 g MOPS, pH 6.8) at 30° C. until the $OD_{600}$ was 8. The cells were spun down at 4° C. and then washed twice with cold tris-HCl buffer (0.1%, pH 8.0). After renewed centrifugation, the cells were taken up in cold tris-HCl buffer (0.1%, pH 8.0) and adjusted to an $OD_{600}$ of 160. For cell disruption, 1 ml of this cell suspension was transferred into 2 ml Ribolyser tubes from Hybaid and lysed in a Ribolyser from Hybaid at a rotation setting of 6.0 three times for 30 sec each time. The lysate was clarified by centrifugation at 15 000 rpm and 4° C. in an Eppendorf centrifuge for 30 minutes, and the supernatant was transferred into a new Eppendorf cup. The protein content was determined as described by Bradford, M. M. (1976) Anal. Biochem. 72:248-254.

The aspartokinase enzymatic activity was determined as follows. 1 ml reaction mixtures with 100 mM Tris-HCl (pH 8.0), 10 mM $MgCl_2$, 600 mM hydroxylamine HCl (pH 7.0 with 10N KOH), 4 mM ATP, 200 mM aspartate (sodium salt) and $H_2O$ ad 1 ml were incubated at 30° C. for 10 min. The assay was started by adding the respective protein lysate and inubating at 30° C. for 30 min. The reaction was stopped by adding 1 ml of the stop solution (10% iron chloride, 3.3% trichloroacetic acid, 0.7N NaCl) to the reaction mixture. After a centrifugation step, the $OD_{540}$ of the supernatant was measured. 1 unit in this case is equivalent to 1 nmol of aspartate hydroxamate formed per mg of protein and per minute.

The results are shown in Table 1a.

TABLE 1a

| Strain | Specific activity [nmol/mg/min] |
| --- | --- |
| ATCC 13032 $lysC^{fbr}$ | 19.35 |
| ATCC 13032 Psod $lysC^{fbr}$ | 41.22 |

It was possible to double the aspartokinase activity by integrating the Psod lysC contruct into the chromosome.

EXAMPLE 5

Production of Lysine

To investigate the effect of the Psod lysC construct on lysine production, the strain ATCC13032, ATCC13032 $lysC^{fbr}$ or ATCC13032 Psod $lySC^{fbr}$ was cultured on CM plates (10.0 g/l D-glucose, 2.5 g/l NaCl, 2.0 g/l urea, 10.0 g/l Bacto peptone (Difco), 5.0 g/l yeast extract (Difco), 5.0 g/l beef extract (Difco), 22.0 g/l agar (Difco), autoclaved (20 min. 121° C.)) at 30° C. for 2 days. The cells were then scraped off the plate and resuspended in saline. For the main culture, 10 ml of medium 1 and 0.5 g of autoclaved $CaCO_3$ (Riedel de Haen) in a 100 ml Erlenmeyer flask were inoculated with the cell suspension until the $OD_{600}$ was 1.5 and incubated on a shaker of the type Infors AJ118 (from Infors, Bottmingen, Switzerland) at 220 rpm for 39 h. The concentration of the lysine secreted into the medium was then determined.

| Medium I: | |
| --- | --- |
| 40 g/l | sucrose |
| 60 g/l | molasses (calculated for 100% sugar content) |

-continued

Medium I:

| | |
|---|---|
| 10 g/l | (NH$_4$)$_2$SO$_4$ |
| 0.4 g/l | MgSO$_4$*7H$_2$O |
| 0.6 g/l | KH$_2$PO$_4$ |
| 0.3 mg/l | thiamin * HCl |
| 1 mg/l | biotin (from a 1 mg/ml stock solution which had been sterilized by filtration and adjusted to pH 8.0 with NH$_4$OH) |
| 2 mg/l | FeSO$_4$ |
| 2 mg/l | MnSO$_4$ adjusted to pH 7.8 with NH$_4$OH, autoclaved (121° C., 20 min). |

In addition, vitamin B12 (hydroxycobalamin Sigma Chemicals) from a stock solution (200 µg/ml, sterilized by filtration) is added to a final concentration of 100 µg/l.

The amino acid concentration was determined by Agilent high pressure liquid chromatography on an Agilent 1100 series LC system HPLC. Precolumn derivatization with ortho-phthalaldehyde permits quantification of the amino acids formed, and the amino acid mixture is fractionated on a Hypersil AA column (Agilent).

The result of the investigation is shown in Table 2a.

TABLE 2a

| Strain | L-lysine (g/l) |
|---|---|
| ATCC13032 | 0 |
| ATCC13032 lysC$^{fbr}$ | 10.15 |
| ATCC13032 PsodlysC$^{fbr}$ | 12.67 |

EXAMPLE 6

Preparation of the Vector pCLiK5MCS

Firstly, the ampicillin resistance and origin of replication of the vector pBR322 were amplified by the polymerase chain reaction (PCR) using the oligonucleotide primers SEQ ID NO: 23 and SEQ ID NO: 24.

SEQ ID NO: 23
5'-CCCGGGATCCGCTAGCGGCGCGCCGGCCGGCCCGGTGTGAAATACCG

CACAG-3'

SEQ ID NO: 24
5'-TCTAGACTCGAGCGGCCGCGGCCGGCCTTTAAATTGAAGACGAAAGG

GCCTCG-3'

Besides the sequences complementary to pBR322, the oligonucleotide primer SEQ ID NO: 23 contains in the 5'-3' direction the cleavage sites for the restriction endonucleases SmaI, BamHI, NheI and AscI and the oligonucleotide primer SEQ ID NO: 24 contains in the 5'-3' direction the cleavage sites for the restriction endonucleases XbaI, XhoI, NotI and DraI. The PCR reaction was carried out with PfuTurbo polymerase (Stratagene, La Jolla, USA) by a standard method such as Innis et al. (PCR Protocols. A Guide to Methods and Applications, Academic Press (1990)). The resulting DNA fragment with a size of approximately 2.1 kb as purified using the GFX™PCR, DNA and Gel Band purification kit (Amersham Pharmacia, Freiburg) in accordance with the manufacturer's instructions. The blunt ends of the DNA fragment were ligated together using the rapid DNA ligation kit (Roche Diagnostics, Mannheim) in accordance with the manufacturer's instructions, and the ligation mixture was transformed into competent E. coli XL-1 Blue (Stratagene, La Jolla, USA) by standard methods as described in Sambrook et al. (Molecular Cloning. A Laboratory Manual, Cold Spring Harbor (1989)). Plasmid-harboring cells were selected by plating out on LB agar (Lennox, 1955, Virology, 1:190) containing ampicillin (50 µg/ml).

The plasmid DNA of an individual clone was isolated using the Qiaprep spin miniprep kit (Qiagen, Hilden) in accordance with the manufacturer's instructions and checked by restriction digestions. The plasmid obtained in this way is called pCLiK1.

Starting from the plasmid pWLT1 (Liebl et al., 1992) as template for a PCR reaction, a kanamycin resistance cassette was amplified using the oligonucleotide primers SEQ ID NO: 25 and SEQ ID NO: 26.

SEQ ID NO: 25:
5'-GAGATCTAGACCCGGGGATCCGCTAGCGGGCTGCTAAAGGAAGCGG

A-3'

SEQ ID NO: 26
5'-GAGAGGCGCGCCGCTAGCGTGGGCGAAGAACTCCAGCA-3'

Besides the sequences complementary to pWLT1, the oligonucleotide primer SEQ ID NO: 25 contains in the 5'-3' direction the cleavage sites for the restriction endonucleases XbaI, SmaI, BamHI, NheI and the oligonucleotide primer SEQ ID NO: 26 contains in the 5'-3' direction the cleavage sites for the restriction endonucleases AscI and NheI. The PCR reaction was carried out with PfuTurbo polymerase (Stratagene, La Jolla, USA) by standard methods such as Innis et al. (PCR Protocols. A Guide to Methods and Applications, Academic Press (1990)). The resulting DNA fragment with a size of approximately 1.3 kb was purified using the GFX™PCR, DNA and Gel Band purification kit (Amersham Pharmacia, Freiburg) in accordance with the manufacturer's instructions. The DNA fragment was cut with the restriction endonucleases XbaI and AscI (New England Biolabs, Beverly, USA) and subsequently again purified using the GFX™PCR, DNA and Gel Band purification kit (Amersham Pharmacia, Freiburg) in accordance with the manufacturer's instructions. The vector pCLiK1 was likewise cut with the restriction endonucleases XbaI and AscI and dephosphorylated with alkaline phosphatase (I (Roche Diagnostics, Mannheim)) in accordance with the manufacturer's instructions. After electrophoresis in a 0.8% agarose gel, the linearized vector (approx. 2.1 kb) was isolated using the GFX™PCR, DNA and Gel Band purification kit (Amersham Pharmacia, Freiburg) in accordance with the manufacturer's instructions. This vector fragment was ligated with the cut PCR fragment using the rapid DNA ligation kit (Roche Diagnostics, Mannheim) in accordance with the manufacturer's instructions, and the ligation mixture was transformed into competent E. coli XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing ampicillin (50 µg/ml) and kanamycin (20 µg/ml).

The plasmid DNA of an individual clone was isolated using the Qiaprep spin miniprep kit (Qiagen, Hilden) in accordance with the manufacturer's instructions and checked by restriction digestions. The plasmid obtained in this way is called pCLiK2.

The vector pCLiK2 was cut with the restriction endonuclease DraI (New England Biolabs, Beverly, USA). After electrophoresis in a 0.8% agarose gel, a vector fragment approx. 2.3 kb in size was isolated using the GFX™PCR, DNA and Gel Band purification kit (Amersham Pharmacia, Freiburg) in accordance with the manufacturer's instructions. This vector fragment was religated using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing kanamycin (20 µg/ml).

The plasmid DNA of an individual clone was isolated using the Qiaprep spin miniprep kit (Qiagen, Hilden) in accordance with the manufacturer's instructions and checked by restriction digestions. The plasmid obtained in this way is called pCLiK3.

Starting from the plasmid pWLQ2 (Liebl et al., 1992) as template for a PCR reaction, the origin of replication pHM1519 was amplified using the oligonucleotide primers SEQ ID NO: 27 and SEQ ID NO: 28.

```
                                     SEQ ID NO: 27:
   5'-GAGAGGGCGGCCGCGCAAAGTCCCGCTTCGTGAA-3'

SEQ ID NO: 28:
   5'-GAGAGGGCGGCCGCTCAAGTCGGTCAAGCCACGC-3'
```

Besides the sequences complementary to pWLQ2, the oligonucleotide primers SEQ ID NO: 27 and SEQ ID NO: 28 contain cleavage sites for the restriction endonuclease NotI. The PCR reaction was carried out with PfuTurbo polymerase (Stratagene, La Jolla, USA) by a standard method such as Innis et al. (PCR Protocols. A Guide to Methods and Applications, Academic Press (1990)). The resulting DNA fragment with a size of approximately 2.7 kb was purified using the GFX™PCR, DNA and Gel Band purification kit (Amersham Pharmacia, Freiburg) in accordance with the manufacturer's instructions. The DNA fragment was cut with the restriction endonuclease NotI (New England Biolabs, Beverly, USA) and then again purified with the GFX™PCR, DNA and Gel Band purification kit (Amersham Pharmacia, Freiburg) in accordance with the manufacturer's instructions. The vector pCLiK3 was likewise cut with the restriction endonuclease NotI and dephosphorylated with alkaline phosphatase (I (Roche Diagnostics, Mannheim)) in accordance with the manufacturer's instructions. After electrophoresis in a 0.8% agarose gel, the linearized vector (approx. 2.3 kb) was isolated with the GFX™PCR, DNA and Gel Band purification kit (Amersham Pharmacia, Freiburg) in accordance with the manufacturer's instructions. This vector fragment was ligated with the cut PCR fragment using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing kanamycin (20 µg/ml).

The plasmid DNA of an individual clone was isolated using the Qiaprep spin miniprep kit (Qiagen, Hilden) in accordance with the manufacturer's instructions and checked by restriction digestions. The plasmid obtained in this way is called pCLiK5. To extend pCLiK5 by a multiple cloning site (MCS), the two synthetic, very substantially complementary oligonucleotides SEQ ID NO: 29 and SEQ ID NO: 30, which contain cleavage sites for the restriction endonucleases SwaI, XhoI, AatI, ApaI, Asp718, MluI, NdeI, SpeI, EcoRV, SalI, ClaI, BamHI, XbaI and SmaI, were combined by heating together at 95° C. and slow cooling to give a double-stranded DNA fragment.

```
                                     SEQ ID NO: 29:
   5'-TCGAATTTAAATCTCGAGAGGCCTGACGTCGGGCCCGGTACCACGCG

TCATATGACTAGTTCGGACCTAGGGATATCGTCGACATCGATGCTCTTCT

GCGTTAATTAACAATTGGGATCCTCTAGACCCGGGATTTAAAT-3'

SEQ ID NO: 30:
   5'-GATCATTTAAATCCCGGGTCTAGAGGATCCCAATTGTTAATTAACGC

AGAAGAGCATCGATGTCGACGATATCCCTAGGTCCGAACTAGTCATATGA

CGCGTGGTACCGGGCCCGACGTCAGGCCTCTCGAGATTTAAAT-3'
```

The vector pCLiK5 was cut with the restriction endonucleases XhoI and BamHI (New England Biolabs, Beverly, USA) and dephosphorylated with alkaline phosphatase (I (Roche Diagnostics, Mannheim)) in accordance with the manufacturer's instructions. After electrophoresis in a 0.8% agarose gel, the linearized vector (approx. 5.0 kb) was isolated with the GFX™PCR, DNA and Gel Band purification kit (Amersham Pharmacia, Freiburg) in accordance with the manufacturer's instructions. This vector fragment was ligated to the synthetic double-stranded DNA fragment using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing kanamycin (20 µg/ml).

The plasmid DNA of an individual clone was isolated using the Qiaprep spin miniprep kit (Qiagen, Hilden) in accordance with the manufacturer's instructions and checked by restriction digestions. The plasmid obtained in this way is called pCLiK5MCS.

Sequencing reactions were carried out as described by Sanger et al. (1977) Proceedings of the National Academy of Sciences USA 74:5463-5467. The sequencing reactions were fractionated and evaluated using an ABI prism 377 (PE Applied Biosystems, Weiterstadt).

The resulting plasmid pCLiK5MCS is listed as SEQ ID NO: 31.

EXAMPLE 7

Preparation of the Plasmid PmetA metA

Chromosomal DNA was prepared from *C. glutamicum* ATCC 13032 as described by Tauch et al. (1995) Plasmid 33:168-179 or Eikmanns et al. (1994) Microbiology 140: 1817-1828. The meta gene including the noncoding 5' region was amplified by the polymerase chain reaction (PCR) by standard methods as described in Innis et al. (1990) PCR Protocols. A Guide to Methods and Applications, Academic Press, using the oligonucleotide primers SEQ ID NO: 32 and SEQ ID NO: 33, the chromosomal DNA as template and Pfu Turbo polymerase (from Stratagene).

SEQ ID NO: 32
5'-GCGCGGTACCTAGACTCACCCCAGTGCT-3'
and

SEQ ID NO: 33
5'-CTCTACTAGTTTAGATGTAGAACTCGATGT-3'

The resulting DNA fragment with a size of approx. 1.3 kb was purified using the GFX™PCR, DNA and Gel Band purification kit (Amersham Pharmacia, Freiburg) in accordance with the manufacturer's instructions. It was then cleaved with the restriction enzymes Asp718 and SpeI (Roche Diagnostics, Mannheim) and the DNA fragment was purified with the GFX™PCR, DNA and Gel Band purification kit.

The vector pClik5MCS SEQ ID NO: 31 was cut with the restriction enzymes Asp718 and SpeI and, after fractionation by electrophoresis, a fragment 5 kb in size was isolated using the GFX™PCR, DNA and Gel Band purification kit.

The vector fragment was ligated together with the PCR fragment using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing kanamycin (20 µg/ml).

The plasmid DNA was prepared by methods and using materials from Qiagen. Sequencing reactions were carried out as described by Sanger et al. (1977) Proceedings of the National Academy of Sciences USA 74:5463-5467. The sequencing reactions were fractionated and evaluated using an ABI prism 377 (PE Applied Biosystems, Weiterstadt).

The resulting plasmid pCLiK5MCS PmetA meta is listed as SEQ ID NO: 34.

EXAMPLE 8

Preparation of the Plasmid pCLiK5MCS Psod metA

Chromosomal DNA was prepared from *C. glutamicum* ATCC 13032 as described by Tauch et al. (1995) Plasmid 33:168-179 or Eikmanns et al. (1994) Microbiology 140: 1817-1828. A DNA fragment of approx. 200 base pairs from the noncoding 5' region (region of the expression unit) of superoxide dismutase (Psod) was amplified by the polymerase chain reaction (PCR) by standard methods such as Innis et al. (1990) PCR Protocols. A Guide to Methods and Applications, Academic Press, using the oligonucleotide primers SEQ ID NO: 35 and SEQ ID NO: 36, the chromosomal DNA as template and Pfu Turbo polymerase (from Stratagene).

SEQ ID NO: 35
5'-GAGACTCGAGAGCTGCCAATTATTCCGGG-3'
and

SEQ ID NO: 36
5'-CCTGAAGGCGCGAGGGTGGGCATGGGTAAAAAATCCTTTCG-3'

The resulting DNA fragment was purified with the GFX™PCR, DNA and Gel Band purification kit (Amersham Pharmacia, Freiburg) in accordance with the manufacturer's instructions.

Starting from plasmid PmetA meta SEQ ID 34 as template for a PCR reaction, a part of meta was amplified using the oligonucleotide primers SEQ ID NO: 37: and SEQ ID NO: 38.

SEQ ID NO: 37   5'-CCCACCCTCGCGCCTTCAG-3'
and

SEQ ID NO: 38   5'-CTGGGTACATTGCGGCCC-3'

The resulting DNA fragment of approximately 470 base pairs was purified with the GFX™PCR, DNA and Gel Band purification kit in accordance with the manufacturer's instructions.

In a further PCR reaction, the two fragments obtained above were employed together as template. Owing to the sequences which have been introduced with the oligonucleotide primer SEQ ID NO: 36 and are homologous to meta, during the PCR reaction the two fragments are attached to one another and extended to give a continuous DNA strand by the polymerase employed. The standard method was modified by adding the oligonucleotide primers used SEQ ID NO: 35 and SEQ ID NO: 38, to the reaction mixture only at the start of the second cycle.

The amplified DNA fragment of approximately 675 base pairs was purified using the GFX™PCR, DNA and Gel Band purification kit in accordance with the manufacturer's instructions. It was then cleaved with the restriction enzymes XhoI and NcoI (Roche Diagnostics, Mannheim) and fractionated by gel electrophoresis. Subsequently, the DNA fragment approximately 620 base pairs in size was purified from the agarose using the GFX™PCR, DNA and Gel Band purification kit (Amersham Pharmacia, Freiburg). The plasmid PmetA meta SEQ ID NO: 34 was cleaved with the restriction enzymes NcoI and SpeI (Roche Diagnostics, Mannheim). After fractionation by gel electrophoresis, a meta fragment approximately 0.7 kb in size was purified from the agarose using the GFX™PCR, DNA and Gel Band purification kit.

The vector pClik5MCS SEQ ID NO: 31 was cut with the restriction enzymes XhoI and SpeI (Roche Diagnostics, Mannheim) and, after fractionation by electrophoresis, a fragment 5 kb in size was isolated using the GFX™PCR, DNA and Gel Band purification kit.

The vector fragment was ligated together with the PCR fragment and the meta fragment using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing kanamycin (20 µg/ml).

The plasmid DNA was prepared by methods and using materials from Qiagen. Sequencing reactions were carried out as described by Sanger et al. (1977) Proceedings of the National Academy of Sciences USA 74:5463-5467. The sequencing reactions were fractionated and evaluated using an ABI prism 377 (PE Applied Biosystems, Weiterstadt).

The resulting plasmid pCLiK5MCS PSODmetA is listed as SEQ ID NO: 39.

EXAMPLE 9

MetA Activities

The strain *Corynebacterium glutamicum* ATCC13032 was transformed with each of the plasmids pClik5 MCS, pClik MCS PmetA meta, pCLiK5MCS Psod meta by the method described (Liebl, et al. (1989) FEMS Microbiology Letters 53:299-303). The transformation mixture was plated on CM plates which additionally contained 20 mg/l kanamycin in order to select for plasmid-containing cells. Resulting Kan-resistant clones were picked and isolated. *C. glutamicum* strains which contained one of these plasmid constructs were cultured in MMA medium (40 g/l sucrose, 20 g/l $(NH_4)_2SO_4$, 1 g/l $KH_2PO_4$, 1 g/l $K_2HPO_4$, 0.25 g/l $MgSO_4 \times 7H_2O$, 54 g Aces, 1 ml $CaCl_2$ (10 g/l), 1 ml protocatechuate (300 mg/10 ml), 1 ml trace element solution (10 g/l $FeSO_4 \times 7H_2O$, 10 g/l $MnSO_4 \times H_2O$, 2 g/l $ZnSO_4 \times 7H_2O$, 0.2 g/l $CuSO_4$, 0.02 g/l $NiCl_2 \times 6H_2O$), 100 µg/l vitamin $B_{12}$, 0.3 mg/l thiamine, 1 mM leucine, 1 mg/l pyridoxal HCl, 1 ml biotin (100 mg/l), pH 7.0) at 30° C. overnight. The cells were spun down at 4° C. and then washed twice with cold Tris-HCl buffer (0.1%, pH 8.0). After renewed centrifugation, the cells were taken up in cold Tris-HCl buffer (0.1%, pH 8.0) and adjusted to an $OD_{600}$ of 160. For cell disruption, 1 ml of this cell suspension was transferred into 2 ml Ribolyser tubes from Hybaid and lysed in a Ribolyser from Hybaid with a rotation setting of 6.0 three times for 30 sec each time. The lysate was clarified by centrifugation at 15 000 rpm and 4° C. in an Eppendorf centrifuge for 30 minutes, and the supernatant was transferred into a new Eppendororf cup. The protein content was determined as described by Bradford, M. M. (1976) Anal. Biochem. 72:248-254.

The measurement of the enzymatic activity of meta was carried out as follows. The 1 ml reaction mixtures contained 100 mM potassium phosphate buffer (pH 7.5), 5 mM $MgCl_2$, 100 µM acetyl-CoA, 5 mM L-homoserine, 500 µM DTNB (Ellman's reagent) and cell extract. The assay was started by adding the respective protein lysate and incubated at room temperature. Kinetics were then recorded at 412 nm for 10 min.

The results are shown in Table 3a.

TABLE 3a

| Strain | Specific activity [nmol/mg/min] |
| --- | --- |
| ATCC 13032 pClik5MCS | 12.6 |
| ATCC 13032 pClik5MCS PmetA metA | 50.7 |
| ATCC 13032 pClik5MCS Psod metA | 100.7 |

It was possible to increase MetA activity considerably by using the heterologous expression unit Psod.

We claim:

1. A genetically modified microorganism, wherein the microorganism comprises a construct comprising
   (1) a nucleic acid having promoter activity selected from the group consisting of
      a) the nucleotide sequence of SEQ ID NO: 1; and
      b) a nucleotide sequence having at least 98% identity to the entire nucleotide sequence of SEQ ID NO: 1; and
   (2) one or more nucleic acids to be transcribed in the microorganism, wherein the one or more nucleic acids is heterologous and functionally linked to the nucleic acid having promoter activity;
   where the microorganism is *Corynebacterium glutamicum*, and
   where transcription of the one or more nucleic acids results in increasing the transcription rate or causes transcription of the one or more nucleic acids in the modified microorganism compared with a corresponding wild type microorganism.

2. The genetically modified microorganisms of claim 1, wherein the microorganism has an increased transcription rate of at least one of the one or more nucleic acids compared with the corresponding wild type microorganism.

3. The genetically modified microorganism of claim 1, wherein the one or more nucleic acids is selected from the group consisting of nucleic acids encoding a protein from the biosynthetic pathway of proteinogenic and non-proteinogenic amino acids, nucleic acids encoding a protein from the biosynthetic pathway of nucleotides and nucleosides, nucleic acid encoding a protein from the biosynthetic pathway of organic acids, nucleic acids encoding a protein from the biosynthetic pathway of lipids and fatty acids, nucleic acids encoding a protein from the biosynthetic pathway of diols, nucleic acids encoding a protein from the biosynthetic pathway of carbohydrates, nucleic acids encoding a protein from the biosynthetic pathway of aromatic compounds, nucleic acids encoding a protein from the biosynthetic pathway of vitamins, nucleic acids encoding a protein from the biosynthetic pathway of cofactors, and nucleic acids encoding a protein from the biosynthetic pathway of enzymes, where the gene may comprise further regulatory elements.

4. The genetically modified microorganism of claim 3, wherein the protein is selected from the group consisting of aspartate kinase, aspartate-semialdehyde dehydrogenase, diaminopimelate dehydrogenase, diaminopimelate decarboxylase, dihydrodipicolinate synthetase, dihydrodipicolinate reductase, glyceraldehyde-3-phosphate dehydrogenase, 3-phosphoglycerate kinase, pyruvate carboxylase, triose-phosphate isomerase, transcriptional regulator LuxR, transcriptional regulator LysR1, transcriptional regulator LysR2, malate-quinone oxidoreductase, glucose-6-phosphate dehydrogenase, 6-phosphogluconate dehydrogenase, transketolase, transaldolase, homoserine O-acetyltransferase, cystathionine gamma-synthase, cystathionine beta-lyase, serine hydroxymethyltransferase, O-acetylhomoserine sulfhydrylase, methylenetetrahydrofolate reductase, phosphoserine aminotransferase, phosphoserine phosphatase, serine acetyltransferase, homoserine dehydrogenase, homoserine kinase, threonine synthase, threonine exporter carrier, threonine dehydratase, pyruvate oxidase, lysine exporter, biotin ligase, cysteine synthase I, cysteine synthase II, coenzyme B12-dependent methionine synthase, coenzyme B12-independent methionine synthase, sulfate adenylyltransferase subunit 1 and 2, phosphoadenosine-phosphosulfate reductase, ferredoxin-sulfite reductase, ferredoxin NADP reductase, 3-phosphoglycerate dehydrogenase, RXA00655 regulator, RXN2910 regulator, arginyl-tRNA synthetase, phosphoenolpyruvate carboxylase, threonine efflux protein, serine hydroxymethyltransferase, fructose-1,6-bisphosphatase, protein of sulfate reduction RXA077, protein of sulfate reduction RXA248, protein of sulfate reduction RXA247, protein OpcA, 1-phosphofructokinase, and 6-phosphofructokinase.

5. A method for producing the microorganism of claim 1, comprising introducing one or more nucleic acids having promoter activity into a microorganism,
   wherein the nucleic acid having promoter selected from the group consisting of
   a) a nucleic acid molecule comprising the nucleotide sequence of SEQ ID NO: 1; and
   b) a nucleic acid molecule comprising a nucleotide sequence having at least 98% identity to the entire nucleotide sequence of SEQ ID NO: 1.

6. A method for increasing the transcription rate or causing the transcription of a gene in a microorganism compared with the corresponding wild type microorganism comprising regulating transcription of a gene by cultivating the genetically modified microorganism of claim 1.

7. A method for increasing the transcription rate or causing the transcription of a gene in a microorganism compared with the corresponding wild type microorganism comprising
   increasing the transcription rate or causing the transcription of a gene in a microorganism by a nucleic acid having promoter activity,
   where the gene is heterologous and functionally linked to the nucleic acid having promoter activity and wherein the nucleic acid having promoter activity is selected from the group consisting of
   a) a nucleic acid molecule comprising the nucleotide sequence of SEQ ID NO: 1; and
   b) a nucleic acid molecule comprising a nucleotide sequence having at least 98% identity to the entire nucleotide sequence of SEQ ID NO: 1; and
   where the microorganism is *Corynebacterium glutamicum*.

8. The method of claim 7, wherein the increasing the transcription rate or causing the transcription of the gene comprises introducing one or more of the nucleic acids having promoter activity into the microorganism.

9. The method of claim 8, where the one or more of the nucleic acids having promoter activity is introduced into the genome of the microorganism so that transcription of one or more endogenous genes takes place under the control of the introduced nucleic acid having promoter activity.

10. The method of claim 8, wherein the one or more nucleic acids having promoter activity is introduced in a construct comprising the nucleic acid having promoter activity functionally linked to one or more nucleic acids to be transcribed into the microorganism.

11. The method of claim 7, wherein the gene is selected from the group consisting of nucleic acids encoding a protein from the biosynthetic pathway of proteinogenic and non-proteinogenic amino acids, nucleic acids encoding a protein from the biosynthetic pathway of nucleotides and nucleosides, nucleic acids encoding a protein from the biosynthetic pathway of organic acids, nucleic acids encoding a protein from the biosynthetic pathway of lipids and fatty acids, nucleic acids encoding a protein from the biosynthetic pathway of diols, nucleic acids encoding a protein from the biosynthetic pathway of carbohydrates, nucleic acids encoding a protein from the biosynthetic pathway of aromatic compounds, nucleic acids encoding a protein from the biosynthetic pathway of vitamins, nucleic acids encoding a protein from the biosynthetic pathway of cofactors, and nucleic acids encoding a protein from the biosynthetic pathway of enzymes, where the genes may comprise further regulatory elements.

12. The method of claim 11, wherein the protein is selected from the group consisting of aspartate kinase, aspartate-semialdehyde dehydrogenase, diaminopimelate dehydrogenase, diaminopimelate decarboxylase, dihydrodipicolinate synthetase, dihydrodipicolinate reductase, glyceraldehyde-3-phosphate dehydrogenase, 3-phosphoglycerate kinase, pyruvate carboxylase, triosephosphate isomerase, transcriptional regulator LuxR, transcriptional regulator LysR1, transcriptional regulator LysR2, malate-quinone oxidoreductase, glucose-6-phosphate dehydrogenase, 6-phosphogluconate dehydrogenase, transketolase, transaldolase, homoserine O-acetyltransferase, cystathionine gamma-synthase, cystathionine beta-lyase, serine hydroxymethyltransferase, O-acetylhomoserine sulfhydrylase, methylenetetrahydrofolate reductase, phosphoserine aminotransferase, phosphoserine phosphatase, serine acetyltransferase, homoserine dehydrogenase, homoserine kinase, threonine synthase, threonine exporter carrier, threonine dehydratase, pyruvate oxidase, lysine exporter, biotin ligase, cysteine synthase I, cysteine synthase II, coenzyme B12-dependent methionine synthase, coenzyme B12-independent methionine synthase, sulfate adenylyltransferase subunit 1 and 2, phosphoadenosine-phosphosulfate reductase, ferredoxin-sulfite reductase, ferredoxin NADP reductase, 3-phosphoglycerate dehydrogenase, RXA00655 regulator, RXN2910 regulator, arginyl-tRNA synthetase, phosphoenolpyruvate carboxylase, threonine efflux protein, serine hydroxymethyltransferase, fructose-1,6-bisphosphatase, protein of sulfate reduction RXA077, protein of sulfate reduction RXA248, protein of sulfate reduction RXA247, protein OpcA, 1-phosphofructokinase, and 6-phosphofructokinase.

\* \* \* \* \*

UNITED STATES PATENT AND TRADEMARK OFFICE
CERTIFICATE OF CORRECTION

PATENT NO.          : 8,071,365 B2
APPLICATION NO.     : 12/030575
DATED               : December 6, 2011
INVENTOR(S)         : Burkhard Kroger et al.

Page 1 of 1

It is certified that error appears in the above-identified patent and that said Letters Patent is hereby corrected as shown below:

In claim 5, at column 127, line number 27, "wherein the nucleic acid having promoter selected from the" should read -- wherein the nucleic acid having promoter activity is selected from the --

Signed and Sealed this
Thirteenth Day of March, 2012

David J. Kappos
*Director of the United States Patent and Trademark Office*